(12) United States Patent
Bencherif et al.

(10) Patent No.: US 7,067,261 B2
(45) Date of Patent: Jun. 27, 2006

(54) METHODS AND COMPOSITIONS FOR TREATMENT OF CENTRAL NERVOUS SYSTEM DISORDERS

(75) Inventors: Merouane Bencherif, Winston-Salem, NC (US); Mario B. Marrero, Evans, GA (US)

(73) Assignees: Targacept, Inc., Winston-Salem, NC (US); Medical College of Georgia Research Institute, Inc., Augusta, GA (US)

( * ) Notice: Subject to any disclaimer, the term of this patent is extended or adjusted under 35 U.S.C. 154(b) by 167 days.

(21) Appl. No.: 10/318,842

(22) Filed: Dec. 13, 2002

(65) Prior Publication Data

US 2003/0158211 A1 Aug. 21, 2003

Related U.S. Application Data

(60) Provisional application No. 60/369,934, filed on Apr. 4, 2002, provisional application No. 60/340,582, filed on Dec. 14, 2001.

(51) Int. Cl.
*G01N 33/53* (2006.01)
*A61K 49/00* (2006.01)
*C12P 1/00* (2006.01)
*C12P 19/40* (2006.01)

(52) U.S. Cl. .......................... 435/7.1; 424/9.1; 435/41; 435/88

(58) Field of Classification Search ................ 435/7.1, 435/41, 88, 7.93; 424/9.1
See application file for complete search history.

(56) References Cited

U.S. PATENT DOCUMENTS

| | | | |
|---|---|---|---|
| 4,922,901 A | 5/1990 | Brooks et al. | 128/203.26 |
| 5,583,140 A | 12/1996 | Bencherif et al. | 514/299 |
| 5,597,919 A | 1/1997 | Dull et al. | 544/242 |
| 5,604,231 A | 2/1997 | Smith et al. | 514/256 |
| 5,712,270 A | 1/1998 | Sabb | 514/212 |
| 5,837,815 A | 11/1998 | Lev et al. | 530/350 |
| 5,952,339 A | 9/1999 | Bencherif et al. | 514/294 |
| 5,977,144 A * | 11/1999 | Meyer et al. | 514/334 |
| 5,986,100 A | 11/1999 | Crooks et al. | 546/101 |
| 6,057,446 A | 5/2000 | Crooks et al. | 546/97 |
| 6,211,372 B1 | 4/2001 | Crooks et al. | 546/94 |
| 6,218,383 B1 | 4/2001 | Bencherif | 514/214.01 |
| 6,232,316 B1 | 5/2001 | Dull et al. | 514/256 |
| 6,310,102 B1 | 10/2001 | Dull et al. | 514/649 |
| 6,376,242 B1 | 4/2002 | Hanson | 435/334 |
| 6,440,681 B1 | 8/2002 | Elliott et al. | 435/7.2 |
| 6,475,753 B1 | 11/2002 | Ruben et al. | 435/69.1 |
| 2002/0052311 A1 | 5/2002 | Solomon et al. | 514/2 |

FOREIGN PATENT DOCUMENTS

| | | |
|---|---|---|
| EP | WO 02/16357 | 2/2002 |
| EP | 1300407 | 4/2003 |
| WO | WO 94/08992 | 4/1994 |
| WO | WO 96/31475 | 10/1996 |
| WO | WO 97/30998 | 8/1997 |
| WO | WO 99/03859 | 1/1999 |
| WO | WO 99/62505 | 12/1999 |
| WO | WO 99/65876 | 12/1999 |
| WO | WO 00/07600 | 2/2000 |
| WO | WO 00/71520 | 11/2000 |
| WO | WO 01/36417 | 5/2001 |
| WO | WO 01/82978 | 11/2001 |
| WO | WO 01/90109 | 11/2001 |
| WO | WO 02/15662 | 2/2002 |
| WO | WO 02/16355 | 2/2002 |
| WO | WO 02/16356 | 2/2002 |
| WO | WO 02/16358 | 2/2002 |
| WO | WO 02/17358 | 2/2002 |
| WO | WO 02/051841 | 7/2002 |

OTHER PUBLICATIONS

McGreer and McGreer, Brain Research Rev. 21: 195-218, 1995.*
Gattu et al., Brain Res. 771: 89-103, 1997.*
Kajstura et al.b, J. Mol. Cell. Card. 29: 859-870, 1997.*
Latchman, D., "Cardiotrophin-1: a novel cytokine and its effects in the heart and other tissues," *Pharmacology & Therapeutics*, 85: 29-37 (2000).
Dineley, K., et al., "β-Amyloid Activates the Mitogen-Activated Protein Kinase Cascade via Hippocampal α7 Nicotinic Acetylcholine Receptors: *In Vitro* and *In Vivo* Mechansims Related to Alzheimer's Disease," *J. Neurosci.* 21(12):4125-4133 (Jun. 15, 2001).
International Search Report for PCT/US02/39952 mailed Jun. 11, 2003.
AbdAlla, S., et al., "The Angiotensin II $AT_2$ Receptor Is an $AT_1$ Receptor Antagonist," *J. Biol. Chem.* 276 (43): 39721-39726 (Oct. 2001).
Akishita, M. et al., "Expression of the AT2 receptor developmentally programs extracellular signal-regulated kinase activity and influences fetal vascular growth," *J. Clin. Invest.* 103(1): 63-71 (1999).

(Continued)

*Primary Examiner*—Janet L. Andres
*Assistant Examiner*—Gyan Chandra
(74) *Attorney, Agent, or Firm*—Womble Carlyle Sandridge & Rice, PLLC

(57) ABSTRACT

The invention provides methods of screening for substances having an effect on a nicotine receptor by contacting a cell having a nicotine receptor with a test substance; and determining any increase or decrease in phosphorylation of Janus-Activated Kinase 2 (JAK2). An increase in phosphorylation of JAK2 indicates that the test substance stimulates the nicotine receptor, and wherein a decrease in phosphorylation of JAK2 indicates that the test substance inhibits the nicotine receptor. The invention also provides screening methods for identification of substances that affect nicotine receptor activity through activity mediated by the AT2 receptor. Related pharmaceutical compositions and methods of treatment are also provided.

11 Claims, 10 Drawing Sheets

OTHER PUBLICATIONS

Ali, M. S., et al., "Angiotensin II Stimulates Tyrosine Phosphorylation and Activation of Insulin Receptor Substrate 1 and Protein-tyrosine Phosphatase 1D in Vascular Smooth Muscle Cells," *J. Biol. Chem.* 272(19):12373-12379 (1997).

Ali, M. S., et al., "Dependence on the Motif YIPP for the Physical Association of Jak2 Kinase with the Intracellular Carboxyl Tail of the Angiotensin II $AT_1$ Receptor," *J. Biol. Chem.* 272(37):23382-23388 (1997).

Amiri, F., et al., "Hyperglycemia Enhances Angiotensin II-induced Janus-activated Kinase/STAT Signaling in Vascular Smooth Muscle Cells," *J. Biol. Chem.* 274(45): 32382-32386 (1999).

Amiri, F. et al., "Angiotensin II activation of the JAK/STAT pathway in mesangial cells is altered by high glucose," *Kidney Int.* 61: 1605-1616 (2002).

Arneric, S., et al., "Preclinical Pharmacology of ABT-418: A Prototypical Cholinergic Channel Activator for the Potential Treatment of Alzheimer's Disease," *CNS Drug Rev.* 1(1): 1-26 (1995).

Arneric, S., et al., "Cholinergic channel modulators as a novel therapeutic strategy for Alzheimer's disease," *Exp. Opin Invest. Drugs* 5(1): 79-100 (1996).

Bannon, A. W., et al., "Broad-Spectrum, Non-Opioid Analgesic Activity by Selective Modulation of Neuronal Nicotinic Acetylcholine Receptors," *Science* 279: 77-80 (1998).

Barnes, N. M., et al., "Angiotensin converting enzyme density is increased in temporal cortex from patients with Alzheimer's disease," *Eur. J. Pharmacol* 200: 289-292 (1991).

Bencherif, M., et al., "RJR-2403: A Nicotinic Agonist with CNS Selectivity I. In Vitro Characterization," *J.P.E.T.* 279(3): 1413-1421 (1996).

Bencherif, M. and J. D. Schmitt, "Targeting Neuronal Nicotinic Receptors: a Path to New Therapies," *Current Drug Targets* 1 (4): 349-357 (2002).

Bencherif, M. and R. J. Lukas, "Vanadate amplifies receptor-mediated accumulation of inositol trisphosphates and inhibits inositol tris-and tetrakis-phosphatase activities," *Neurosci. Lett.* 134: 157-160 (1992).

Bernstein, K. E., and M. B. Marrero, "The Importance of Tyrosine Phosphorylation in Angiotensin II Signaling," *Trends. Cardiovasc. Med.* 6(6): 179-187 (1996).

Bhat, G. J., et al., "Angiotensin II Stimulates sis-Inducing Factor-like DNA Biding Activity" *J. Biol. Chem.* 269(50): 31443-31449 (1994).

Bhat, G. J., et al., "Activation of the STAT Pathway by Angiotensin II in T3CHO/$AT_{1A}$ Cells," *j. Biol. Chem.* 270(32): 19059-19065 (1995).

Breese, C.R. et al. "Comparison of the Regional Expression of Nicotinic Acetylcholine Receptor α7 mRNA and [$^{125}$I]-α-Bungarotoxin Binding in Human Postmortem Brain," *J. Com. Neurol.* 387: 385-398 (1997).

Brown, N.J. and D.E. Vaughan, "Angiotensin-Converting Enzyme Inhibitors," *Circulation* 97: 1411-1420 (1998).

Chamoux, E., et al., "The AT2 receptor of Angiotensin II and Apoptosis in Human Fetal Adrenal Gland," *Endocr. Res.* 26(4): 955-957 (Nov. 2000).

Chini, B. et al., "Molecular Cloning and Chromosomal Localization of the Human $α_7$-Nicotinic Receptor Subunit Gene (CHRNA7)," *Genomics* 19: 379-381 (1994).

Cooper, S. T. and N. S. Millar, "Host Cell-Specific Folding and Assembly of the Neuronal Nicotinic Acetylcholine Receptor α7 Subunit," *J. Neurochem.* 68(5): 2140-2151 (1997).

Court, J., et al., "Nicotinic Receptor Abnormalities in Alzheimer's Disease," *Biol. Psychiatry* 49:175-184 (Feb. 2001).

Cui, T. et al., "Pivotal role of tyrosine phosphatase SHP-1 in AT2 receptor-mediated apoptosis in rat fetal vascular smooth muscle cell," *Cardiovasc. Res.* 49(4):863-871 (Mar. 2001).

Damaj, et al., "Analgesic Activity of Metanicotine, A Selective Nicotinic Agonist," *Society for Neuroscience*, 23: 669 ABSTRACT 266.9 (1997).

Darnell, J. E., Jr., et al., "Jak-STAT Pathways and Transcriptional Activation in Response to IFNs and Other Extracellular Signaling Proteins," *Science* 264:1415-1421 (1994).

De Fiebre, C. M., et al., "Characterization of a Series of Anabaseine-Derived Compounds Reveals That the 3-(4)-Dimethylaminocinnamylidine Derivative is a Selective Agonist at Neuronal Nicotinic α7/$^{125}$ l-α-Bungarotoxin Receptor Subtypes," *Mol. Pharmacol.* 47:164-171 (1995).

Digicaylioglu, M. and S. A. Lipton, "Erythropoietin-mediated neuroprotection involves cross-talk between Jak2 and $NF$-$_κB$ signaling cascades," *Nature* 412:641-647 (Aug. 2001).

Dolle, F., et al., "Synthesis and preliminary evaluation of a carbon-11-labelled agonist of the α7 nicotinic acetylcholine receptor," *J. Labelled Cpd. Radiopharm.* 44: 785-795 (2001).

Donnely-Reoberts, D.L. et al, "In vitro neuroprotective properties of the novel cholinergic channel activator (ChCA), ABT-418," *Brain Res.* 719: 36-44 (1996).

Du, J., et al., "G-Protein and Tyrosine Kinase Receptor Cross-Talk in Rat Aortic Smooth Muscle Cells: Thrombin- and Angiotensin II-Induced Tyrosine Phosphorylation of Insulin Receptor Substrate-1 and Insulin-Like Growth Factor 1 Receptor," *Biochem. Biophys, Res, Commun.* 218(3):934-939 (1996).

Duff, J. L. et al., "Angiotensin II Induces 3CH134, a Protein-tyrosine Phosphatase, in Vascular Smooth Muscle Cells," *J Biol. Chem.* 268(350: 26037-26040 (1993).

Duff, J. L..., et al., "Angiotensin II signal transduction and the mitogen-activated protein kinase pathway," *Cardiovasc. Res.* 30(4): 511-517 (1995).

Esther, Jr., C. R., et al., "Lessons from angiotensin-converting enzyme-deficient mice," *Curr. Opin. Nephrol. Hypertens* 5(6): 463-467 (1996).

Fischer, J. W., et al., "Differential regulation of thrombospondin-1 and fibronectin by angiotensin II receptor subtypes in cultured endothelial cells," *Cardiovasc. Res.* 51(4): 784-791 (Sep. 2001).

Gallinat, S., et al., "AT2 receptor stiulation induces generation of ceramides in PC12W cells," *F.E.B.S. Lett.* 443: 75-79 (1999).

Ge, J., and N. M. Barnes, "Alterations in angiotensin $AT_1$ and $AT_2$ receptor subtype levels in brain regions from patients with neurodegenerative disorders," *Eur. J. Pharmacol.* 297: 299-306 (1996).

Greene, L. A. and A. S. Tischler, "Establishment of a Noradrenergic Clonal Line of Rat Adrenal Pheochromocytoma Cells which Respond to Nerve Growth Factor," *Proc.Natl. Acad. Sci. U.S.A.*, 73(7): 2424-2428 (1976).

Harp, J. B., et al., "Role of Intracellular Calcium in the Angiotensin II-Mediated Tyrosine Phosphorylation and Dephosphorylation of PLC-$\gamma$1," *Biochem. Biophys. Res. Commun*. 232(2): 540-544 (1997).

Holladay, M. W., et al., "Neuronal Nicotinic Acetylcholine Receptors as Targets for Drug Discovery," *J. Med. Chem* 40(26): 4169-4194 (1997).

Horiuchi, M., et al., "Stimulation of Different Subtypes of Angiotensin II Receptors, $AT_1$ and $AT_2$ Receptors Regulate STAT Activation of Negative Crosstalk," *Circ. Res*. 84: 876-882 (1999).

Horiuchi, M., et al., "Molecular and Cellular Mechanism of Angiotensin II-Mediated Apoptosis," *Endocr. Res*. 24: 307-314 (1998).

Ishida, M., et al., "Angiotensin II Activates $pp60^{C\text{-}src}$ in Vascular Smooth Muscle Cells," *Cir. Res*. 77(6): 1053-1059 (1995).

Jiao, H., et al., "Direct Association with and Dephosphorylation of Jak2 Kinase by the SH2-Domain-Containing Protein Tyrosine Phosphatase SHP-1," *Mol. Cell. Biol*. 16(12): 6985-6992 (1996).

Kem, W. R., "The Brain $\alpha7$ nicotinic receptor may be an important therapeutic target for the treatment of Alzheimer's disease: studies with DMXBA (GTS-21)," *Behav. Brain Res*. 113(1-2): 169-181 (Aug. 2000).

Kihara, T., et al., "$\alpha7$ Nicotinic Receptor Transduces Signals to Phosphatidylinositol 3-Kinase to Block a $\beta$-Amyloid-induced Neurotoxicity," *J. Biol. Chem*. 276(17): 13541-13546 (Apr. 27, 2001).

Kumano, K., et al., "Blockade of JAK2 by Tyrphostin AG-490 Inhibits Antigen-Induced Eosinophil Recruitment into the Mouse Airways," *Biochem. Biophys. Res. Commun*. 270: 209-214 (Apr. 2, 2000).

Kunioku, H., et al., "Interleukin-6 protects rat PC12 cells from serum deprivation or chemotherapeutic agents through the phosphatidylinositol 3-kinase and STAT3 pathways," *Neurosci. Lett*. 309: 13-16 (Aug. 2001).

Lea, J. P. et al., "Angiotensin II Stimulates Calcineurin Activity in Proximal Tubule Epithelia through AT-1 Receptpor-Mediated Tyrosine Phosphorylation of the PLC-$\gamma$1 Isoform," *J. Am. Soc. Nephrol*. 13(7): 1750-1756 (2002).

Lehtonen, J. Y., et al., "Analysis of Functional Domains of Angiotensin II Type 2 Receptor Involved in Apotosis," *Mol. Endocrinol*. 13(7): 1051-1060 (1999).

Li, W., et al., "The deletion of AT2 receptor gene antagonizes angiotensin II-induced apoptosis in fibroblasts," *Zhonghua Yi Xue Za Zhi* 78(8): 570-3 (Aug. 1998). English abstract only.

Li, W., et al., "Genetic Deletion of AT2 Receptor Antagonizes Angiotensin II-Induced Apoptosis in Fibroblasts of the Mouse Embryo," *Biochem. Biophys. Res. Commun*. 250(1): 72-76 (1998).

Liang, H., et al., "Regulation of Angiotensin II-induced Phosphorylation of STAT3 in Vascular Smooth Muscle Cells," *J. Biol. Chem*. 274(28): 19846-19851 (1999).

Lippiello, P.M., et al., "RJR-2403: A Nicotinic Agonist with CNS Selectivity II. In Vivo Characterization," *J. P. E. T*. 279(3): 1422-1429 (1996).

Liu, Q., et al., "$\beta$Amyloid peptide blocks the response of $\alpha7$-containing nicotinic receptors on hippocampal neurons," *Proc. Natl. Acad. Sci. U.S.A*. 98(8): 4734-9 (Apr. 10, 2001).

Lucius, R., et al., "The Angiotensin II Type 2 ($AT_2$) Receptor Promotes Axonal Regeneration in the Optic Nerve of Adult Rats," *J. Exp. Med*., 188(4): 661-670 (1998).

Lukas, R. J. and M. Bencherif, "Heterogeneity and Regulation of Nicotinic Acetylcholine Receptors," *Int. Rev. Neurobiol*. 34: 25-131 (1992).

Macor, J. E. et al., "The 5-$HT_3$ Antagonist Tropisetron (ICS 205-930) is a Potent and Selective $\alpha7$ Nicotinic Receptor Partial Agonist," *Bioorg. Med. Chem. Lett*. 11: 319-321 (Feb. 2001).

Marrero, M B., et al., "Angiotensin II-Induced Tyroisne Phosphorlation in Mesangial and Vascular Smooth Muscle Cells," *Clin. Exp. Pharmacol. Physiol*. 23(10: 83-88 (1996).

Marrero, M.B. et al., "Regulation of angiotensin II-induced JAK2 tyrosine phosphorylation: roles of SHP-1 and SHP-2," *Am. J. Physiol*., 275 (*Cell Physiol* 44): C1216-C1223 (1998).

Marrero, M.B., et al., "Role of Janus Kinase/Signal Transducer and Activator of Transcription and Mitogen-activated Protein Kinase Cascades in Angiotensin II- and Platelet-derived Growth Factor-induced Vascular Smooth Muscle Cell Proliferation," *J. Biol. Chem*. 272(39): 24684-24690 (1997).

Marrero, M. B., et al., "Angiotensin II Signalling Events Medicated by Tyrosine Phosphorylation," *Cell Signal* 8(1): 21-26 (1996).

Marrero, M. B., et al., "ANG II-induced tyrosine phosphorylation stimulates phospholipase C-$\gamma$1 and Cl channels in mesangial cells," *Am. J. Physiol*. 270 (*Cell Physiol* 39): C1834-C1842 (1996).

Marrero, M.B., et al., "The role of tyrosine phosphorylation in angiotensin II-mediated intracellular signaling," *Cardiovasc. Res*. 30(40: 530-536 (1995).

Marrero, M.B., et al., "Electroporation of $pp60^{c\text{-}src}$ Antibodies Inhibits the Angiotensin II Activation of Phospholipase C-$\gamma$1 in Rat Aortic Smooth Muscle Cells," *J. Biol. Chem*. 270(26): 15734-15738 (1995).

Marrero, M.B., et al., "Direct stimulation of Jak/STAT pathway by the angiotensin II $AT_1$ receptor," *Nature* 375: 247-250 (1995).

Marrero, M.B., et al., "Angiotensin II Stimulates Tyrosine Phosphorylation of Phospholipase C-$\gamma$1 in Vascular Smooth Muscle Cells," *J. Biol. Chem*. 269 (14): 10935-10939 (1994).

McGhee, D.S., et al., "Nicotine Enhancement of Fast Excitatory Synaptic Transmission in CNS by Presynaptic Receptors," *Science* 269: 1692-1696 (1995).

McWhinney, C. D., et al., "Angiotensin II Activates Stat5 Through Jak2 Kinase in Cardiac Myocytes," *J. Mol. Cell. Cardio*. 30: 751-761 (1998).

Mukoyama, M., et al., "Expression Cloning of Type 2 Angiotensin II Receptor Reveals a Unique Class of Seven-transmembrane Receptors," *J. Biol. Chem*. 268(33): 24539-24542 (1993).

Nakajima, M., et al., "Cloning of cDNA and Analysis of the Gene for Mouse Angiotensin II Type 2 Receptor," *Biochem. Biophys. Res. Commun*. 197(2): 393-399 (1993).

Nakajima, M. et al., "The angiotensin II type 2 ($AT_2$) receptor antagonizes the growth effects of the $AT_1$ receptor: Gain-of-function study using gene transfer," *Proc. Natl. Acad. Sci. U.S.A*. 92(23): 10663-10667 (1995).

Narain, Y., et al., "The ACE gene and Alzheimer's disease susceptibility," *J. Med. Genet*. 37(9): 695-697 (Sep. 2000).

Negoro, S., et al., "Activation of JAK/STAT pathway transduces cytoprotective signal in rat acute myocardial infarction," *Cardiovasc. Res*. 47: 797-805 (Sep. 2000).

Newhouse, P. A., et al., "Nicotinic Treatment of Alzheimer's Disease," *Biol. Psychiatry* 49(3): 268-278 (Feb. 2001).

Nouet, S. and C. Nahmias, "Signal transduction from the Angiotensin II AT2 Receptor," *Trends Endocrinol. Metab.*, 11(1): 1-6 (Jan.-Feb. 2000).

Okuda, M., et al., "Angiotensin II type 1 receptor-mediated activation of Ras in cultured rat vascular smooth muscle cells," *Am. J. Physiol.* 271 (*Heart Circ. Physiol* 40): H595-H601 (1996).

Patrick, J. and W. B. Stallcup, "Immunological disctinction between acetylcholine receptor and the α-bungarotoxin-binding component on sympathetic neurons," *Proc. Natl. Acad. Sci. U.S.A.*, 74(10): 4689-4692 (1977).

Papke, R. L., et al., "An evaluation of neuronal nicotinic acetylcholine receptor activation by quaternary nitrogen compounds indicates that choline is selective for the α7 subtype," *Neurosci. Lett.* 213(3): 201-204 (1996).

Paxton, W. G., et al., "The Angiotensin II $AT_1$ Receptor is Tyrosine and Serine Phosphorylated and Can Serve as a Substrate for the SRC Famliy of Tyrosine Kinases," *Biochem. Biophys. Res. Commun.* 200(1):260-267 (1994).

Picciotto, M. R. and M. Zoli, "Nicotinic Receptors in Aging and Dementia," *J. Neurobiol.* 53: 641-655 (2002).

Prasad, C., et al., "Chronic Nicotine Intake Decelerates Aging of Nigrostriatal Dopaminergic Neurons," *Life Sci.* 54(16): 1169-1184 (1994).

Ryan, R. E., et al., "Dose-related neuroprotective effects of chronic nicotine in 6-hydroxydopamine treated rats, and loss of neuroprotection in α4 nicotinic receptor subunit knockout mice," *Br. J. Pharmacol.* 132: 1650-1656 (Apr. 2001).

Sadoshima, J. and S. Izumo, "Molecular Characterization of Angiotensin II-Induced Hypertrophy of Cardiac Myocytes and Hyperplasia of Cardiac Fibroblasts," *Circ. Res.* 73(3): 413-423 (1993).

Sadoshima, J. and S. Izumo, "Signal Transduction Pathways of Angiotensin II-Induced c-fos Gene Expression in Cardiac Myocytes in Vitro. Roles of Phospholipid-Derived Second Messengers," *Circ. Res.* 73(3): 424-438 (1993).

Sakai, I. And A. S. Kraft, "The Kinase Domain of Jak2 Mediates Induction of Bcl-2 and Delays Cell Death in Hematopoietic Cells," *J. Biol. Chem.* 272(19): 12350-12358 (1997).

Sayeski, P. P. et al., "Angiotensin II signal transduction pathways," *Regulatory Peptides* 78: 19-29 (1998).

Sayeski, P. P., et al., "Phosphorylation of $p130^{Cas}$ by Angiotensin II Is Dependent on C-Src, Intracellular $Ca^{2+}$, and Protein Kinase C," *Circ. Res.* 82(12): 1279-1288 (1998).

Schieffer, B., et al., "Importance of Tyrosine Phosphorylation in Angiotensin II Type 1 Receptor Signaling," *Hypertension* 27 (Part 2): 476-480 (1996).

Schieffer, B., et al., "Angiotensin II Controls $p21^{ras}$ Activity via $pp60^{c-src}$," *J. Biol. Chem.* 271(17): 10329-10333 (1996).

Schieffer, B., et al., "The role of tyrosine phosphorylation in angiotensin II mediated intracellular signaling and cell growth," *J. Mol. Med.* 74(2): 85-91 (1996).

Schindler, C. and J.E. Darnell, Jr., "Transcriptional Responses to Polypeptide Ligands: The JAK-STAT Pathway," *Annu. Rev. Biochem.* 64: 621-651 (1995).

Schmitt, J. and M. Bencherif, "Chapter 5. Targeting Nicotinic Acetylcholine Receptors: Advances in Molecular Design and Therapies," *Ann. Rep. Med. Chem.* 35: 41-51 (2000).

Schmitt, J., "Exploring the Nature of Molecular Recognition in Nicotinic Acetylcholine Receptors," *Curr. Med. Chem.*, 7(8): 749-800 (Aug. 2000).

Seo, J., et al., "Effects of Nicotine on APP Secretion and Aβ- or $CT_{105}$-Induced Toxicity," *Biol. Psychiatry* 49(3): 240-247 (Feb. 2001).

Shaw, S., et al., "Janus Kinase 2, an Early Target of α7 Nicotinic Acetylcholine Receptor-mediated Neuroprotection against Aβ-(1-42) Amyloid," *J. Biol. Chem.* 277(47): 44920-44924 (2002).

Stevens, et al., "Selective $α_7$-nicotinic agonists normalize inhibition of auditory response in DBA mice," *Psychopharm.* 136: 320-327(1998).

Stoll, M. and T. Unger, "Angiotensin and its $AT_2$ receptor: new insights into an old system," *Regul Pept* 99(2-3): 175-182 (Jun. 2001).

Taubman, M. B., et al., "Angiotensin II Induces c-fos mRNA in Aortic Smooth Muscle," *J. Biol. Chem.* 264(1): 526-530 (1989).

Venema, R.C., et al., "Angiotensin II-induced Association of Phospholipase Cyl with the G-protein-coupled $AT_1$ Receptor," *J. Biol. Chem.* 273(13): 7703-7709 (1998).

Venema, R. C., et al., "Angiotensin II-induced Tyrosine Phosphorylation of Signal Transducers and Activators of Transcription 1 Is Regulated by Janus-activated Kinase 2 and Fyn Kinases and Mitogen-activated Protein Kinase Phosphatase 1," *J. Biol. Chem.* 273(46): 30795-30800 (1998).

Vijayaraghavan, S., et al., "Nicotinic Receptors That Bind α-Bungarotoxin on Neurons Raise Intracellular Free $Ca^{2+}$," *Neuron* 8:353-362 (1992).

Wayner, M. J., et al., "Nicotine Blocks Angiotensin II Inhibition of LTP in the Dentate Gyrus," *Peptides* 17(7): 1127-1133 (1996).

Wang, H. Y., et al., "β-$Amyloid_{1-42}$ Binds to α7 Nicotinic Acetylcholine Receptor with High Affinity," *J. Biol. Chem.* 275(8): 5626-5632 (Feb. 2000).

Whiting, P. J., et al., "Functional acetylcholine receptor in PC12 cells reacts with a monoclonal antibody to brain nicotinic receptors," *Nature* 327: 515-518 (1987).

Williams, M., et al., "Neuronal Nicotinic Acetylcholine Receptors," *DN&P* 7(4): 205-223 (1994).

Wolf, G., et al., "Angiotensin II's Antiproliferative Effects Mediated Through AT2-Receptors Depend On Down-Regulation of SM-20," *Lab. Invest.* 82(10): 1305-1317 (2002).

Yamashita, H. and S. Nakamura, "Nicotine rescues PC12 cells from death induced by nerve growth factor deprivation," *Neurosci. Lett.* 213: 145-147 (1996).

* cited by examiner

IP with anti-Aβ (1-42) and blot with anti-alpha7nAChR

Control    AG-490    Nicotine    Nicotine
                                 + AG-490

A. Aβ (1-42) at 0.1 uM

With out AG-490

With AG-490

B. Aβ(1-42) at 1 uM

With out AG-490

With AG-490

0   5   10   30   60   120          0   5   10   30   60   120

Incubation Time (minutes)

1. Control
2. TC-1698
3. ABeta (1-42)
4. AG-490
5. Angiotensin II
6. ABeta (1-42) + TC-1698
7. ABeta (1-42) + TC-1698 + AG-490
8. ABeta (1-42) + TC-1698 + Angiotensin II
9. ABeta (1-42) + TC-1698 + Angiotensin II + Vanadate

METHODS AND COMPOSITIONS FOR TREATMENT OF CENTRAL NERVOUS SYSTEM DISORDERS

This application claims benefit of U.S. Provisional Patent Application No. 60/340,582 filed Dec. 14, 2001, and U.S. Provisional Patent Application No. 60/369,934 filed Apr. 4, 2002.

FIELD OF THE INVENTION

The present invention relates to compounds having pharmaceutical properties, and in particular, to compounds useful for prophylaxis and/or treatment of central nervous system (CNS) disorders, including disease states associated with Alzheimer's disease.

The present invention relates to methods for prophylaxis and/or treatment of patients suffering from or susceptible to such disorders, and in particular, to a method for prophylaxis and/or treatment of patients suffering from those disorders which are associated with neurodegeneration of brain neurons. The present invention also relates to compositions of matter useful as pharmaceutical compositions in the prophylaxis and/or treatment of CNS disorders that have been attributed to neurodegenerative diseases.

BACKGROUND OF THE INVENTION

Nicotinic receptors. Nicotinic acetylcholine receptors (nAChRs) are composed of various combinations of α-subunits (α2–α9) and β-subunits (β2–β4), and are classified into two classes according to their affinity for nicotine or α-bungarotoxin (ABTX) (Vijayaraghavan, S., et al., *Neuron* 8:353–362 (1992)). Of the known αBTX-binding subtypes α7–α9, only α7 receptors are expressed throughout the mammalian brain. Alpha7 receptors form functional homomeric ion channels that promote $Ca^{2+}$ influx, which are rapidly desensitized (Breese, C. R., et al., *J. Com. Neurol.* 387:385–398 (1997); Vijayaraghavan, S., et al., *Neuron* 8:353–362 (1992)) and are thus assumed to be involved in synaptic transmission (McGehee, D. S., et al., *Science* 269:1692–1696 (1995)). Nicotinic agonists selective for the α7 receptor have demonstrated efficacy in improving cognitive functions in rats, primates and AD patients. Due to the multifaceted deficits observed in AD and the limited pharmacopae for management of AD patients, there is an urgent need for new therapies and approaches to optimize existing and emerging therapies.

Nicotine has also been found to inhibit death of PC12 cells cultured in serum-free medium (Yamashita, H. and S. Nakamura, *Neurosci. Lett.* 213:145–147 (1996)). In addition, a selective α7 receptor agonist, anabaseine-derived 3-(4)-dimethylaminocinamylidine (DMAC) (de Fiebre, C. M., et al., *Mol. Pharmacol.* 47:164–171 (1995)), and an activator of nAChR, including the α7 subtype, ABT-418 (Donnelly-Roberts, D. L., et al., *Brain Res.* 719:36–44 (1996)) have also been reported to exert cytoprotective effects.

Nicotine-induced protection in neuronal cells is suppressed by αBTX, a phosphatidylinositol 3-kinase (PI3K) inhibitor (LY294002 and wortmannin), and a Src inhibitor (PP2). In addition, the levels of phosphorylated Akt, an effector of PI3K, are increased by nicotine ((Kihara, T., S. et al., *J. Biol. Chem.* 276:13541–13546 (2001)). These findings suggest that the α7 nicotinic receptor transduces signals to PI3K in a cascade, which ultimately contributes to a neuroprotective effect.

Ang II signaling pathways. The actions of Angiotensin II (Ang II) are mediated through two types of cell surface receptors, (AT1 and AT2). Most of the physiological responses to Ang II in glomerular mesangial cells (GMC) occur via the AR1 receptor subtype (Bernstein, K. E. and M. B. Marrero, *Trends. Cardiovasc. Med.* 6:179–187 (1996); Marrero, M. B., et al., *Cell. Signal.* 8:21–26 (1996)). For AR1 receptors, activation by Ang II results in G protein mediated signaling, including phospholipase C-dependent activation of protein kinase C and release of calcium from intracellular stores (Bernstein, K. E. and M. B. Marrero, *Trends. Cardiovasc. Med.* 6:179–187 (1996)). AT1 receptors also activate signaling pathways traditionally associated with growth factor and cytokine receptors that induce the production of early growth response genes. The signaling cascades whereby Ang II induces early growth response genes, such as c-fos and c-jun proto-oncogenes, does not in general require new protein synthesis and appear to be regulated by post-translational modifications of pre-existing transcription factors (Sadoshima, J. and S. Izumo, *Circ. Res.* 73:413–423 (1993); Okuda, M., Y. Kawahara, and M. Yokoyama, *Am. J. Physiol.* 271: H595–H601, (1996); Sadoshima, J. and S. Izumo, *Circ. Res.* 73:413–423 (1993); Sadoshima, J. and S. Izumo, *Circ. Res.* 73:424–438 (1993); Taubman, M. B., et al., *J. Biol. Chem.* 264:526–530 (1989)). Therefore, the Ang II-induced expression of these early growth response genes is under the direct regulation of intracellular signal transduction pathways. Three intracellular signaling pathways have recently been implicated in the activation of proto-oncogenes: the JAK/STAT, p21ras/Raf-1/MAP kinase, and the PLC-γ1 cascades (Bernstein, K. E. and M. B. Marrero, *Trends. Cardiovasc. Med.* 6:179–187 (1996); Marrero, M. B., et al., *Cell. Signal.* 8:21–26 (1996); Sayeski, P. P., et al. *Regulatory Peptides* 78:19–29 (1998)). From multiple studies focusing on AR1 receptor signal transduction pathways, it has become apparent that the temporal arrangement of agonist-stimulated signaling varies from seconds (i.e., the activation of PLC-γ1 and generation of inositol phosphates) to minutes (e.g., MAP kinase activation) to hours (e.g., JAK/STAT pathway) (Bernstein, K. E. and M. B. Marrero, *Trends. Cardiovasc. Med.* 6:179–187 (1996); Sayeski, P. P., et al., *Regulatory Peptides* 78:19–29 (1998)). The exact mechanism(s) by which the AT1 receptor is able to differentially couple to disparate signal transduction pathways is not clear, but presumably involves a complex series of steps that selectively recruits, activates and then inactivates each signaling system in a time-dependent manner.

Role of the JAK/STAT Pathway in Ang II Signaling. The JAK family of cytosolic tyrosine kinases, traditionally thought to be coupled to cytokine receptors such as those for the interleukins and interferons, have four members (JAK1, JAK2, JAK3 and TYK2) (Darnell, J. E., Jr., et al., *Science* 264:1415–1421 (1994); Taubman, M. B., et al., *J. Biol. Chem.* 264:526–530 (1989)). In response to ligand binding, these JAK tyrosine kinases associate with, tyrosine-phosphorylate, and activate the cytokine receptor itself. Once activated, JAKs tyrosine-phosphorylate and activate other signaling molecules including the STAT family of nuclear transcription factors after binding of the STATs to the receptor (Darnell, J. E., Jr., et al., *Science* 264:1415–1421 (1994); Taubman, M. B., et al., *J. Biol. Chem.* 264:526–530 (1989)). Thus, the JAK/STAT pathway is an important link between cell surface receptors and nuclear transcriptional events leading to cell growth. Recently, Baker and colleagues have shown that STAT1, STAT3, and STAT5 are tyrosine-phosphorylated in response to Ang II in cardiac fibroblasts and AT1 receptor-transfected CHO cells (Bhat, G. J., et al., *J. Biol. Chem.* 269:31443–31449 (1994); Bhat, G. J., et al., *J. Biol. Chem.* 270:19059–19065 (1995); McWhinney, C. D., et al., *J. Mol. Cell. Cardiol.* 30:751–761 (1998)). These investigators also found that Ang II exposure stimulated the phosphorylated monomeric STAT proteins to form homo-($STAT1_2$, $STAT3_2$ or $STAT5_2$) or hetero-(STAT1:STAT3) dimer complexes referred to as SIF (sis-inducing factors). These SIF complexes subsequently translocate to the nucleus and interact with specific DNA motifs called SIE (sis-inducing elements) or PIE (prolactin-inducing element)-like elements within the c-fos promoter, culminating in the activation of this early growth response gene (Bhat, G. J., et al., *J. Biol. Chem.* 269:31443–31449 (1994); Darnell, J. E., Jr., et al., *Science* 264:1415–1421 (1994); McWhinney, C. D., et al., *J. Mol. Cell. Cardiol.* 30:751–761 (1998); Schindler, C. and J. E. Darnell, Jr., *Annu. Rev. Biochem.* 64:621–651 (1995)). The JAK/STAT cascade can be activated by Ang II resulting in tyrosine phosphorylation of JAK2, STAT1 and STAT3, and the translocation of STAT1 and STAT3 to the nucleus (Bhat, G. J., et al., *J. Biol. Chem.* 270:19059–19065 (1995); Marrero, M. B., et al. *Clin. Exp. Pharmacol. Physiol.* 23:83–88 1996; Marrero, M. B., et al., *Nature* 375:247–250 (1995)). Furthermore, the carboxyl-terminal tail of the AT1 receptor binds to JAK2 in an Ang II-dependent manner (Ali, M. S., et al., *J. Biol. Chem.* 272:23382–23388 (1997)). In addition, inhibition of JAK2 tyrosine phosphorylation with the pharmacologic JAK2 inhibitor, AG490, or electroporation of blocking antibodies against STAT1 or STAT3 inhibits Ang II-induced vascular smooth muscle cell (VSMC) proliferation and DNA synthesis (Marrero, M. B., et al., *J. Biol. Chem.* 272:24684–24690 (1997)). These results indicate that G-protein-coupled receptors, in particular the AT1 receptor, can operate via the same intracellular tyrosine phosphorylation pathways previously linked to mitogenic cytokine and growth factor receptors. Finally, the tyrosine phosphatases, SHP-1 and SHP-2, have opposite roles in Ang II-induced JAK2 phosphorylation. SHP-1 appears responsible for JAK2 dephosphorylation and termination of the Ang II-induced JAK/STAT cascade, whereas SHP-2 appears to have an essential role in JAK2 phosphorylation and initiation of the Ang II-induced JAK/STAT cascade leading to cell proliferation (See Jiao, H., et al., Direct association with and dephosphorylation of Jak2 kinase by the SH2-domain-containing protein tyrosine phosphatase SHP-1. *Mol Cell Biol* 16(12):6985–92(1996)).

The motif in the AR1 receptor that is required for association with JAK2 is also required for association with SHP-2 (Marrero, M. B., et al., *Am. J. Physiol.* 275: C1216–C1223 (1998)). Furthermore, SHP-2 is also required for JAK2-Ang II AR1 receptor association (Marrero, M. B., et al., *Am. J. Physiol.* 275:C1216–C1223 (1998)). SHP-2 may thus play a role as an adaptor protein for JAK2 association with the receptor, thereby facilitating JAK2 phosphorylation and activation (Marrero, M. B., et al., *Am. J. Physiol.* 275: C1216–C1223, 1998).

Nicotinic Acetylcholine Receptors and β-Amyloid Toxicity. The cholinergic deficit in Alzheimer's Disease has been clearly established and is the basis for the current symptomatic strategy. There is an early and significant depletion of high affinity nicotinic receptors in Alzheimer's patient's brains (Court, J., et al. *Biol. Psychiatry* 49:175–184 (2001)), and a number of studies have shown cognitive improvement in rodent, primates including humans following administration of ligands targeting nAChRs (Newhouse Pa., et al., *Biol Psychiatry* 49(3):268–78 (2001)). In addition to their known symptomatic effects, neuronal nicotinic ligands have shown neuroprotective activity in vitro (Donnelly-Roberts, D. L., et al. *Brain Res.* 719: 36–44 (1996)) and in vivo (Ryan RE, et al., 132(8):1650–6 (2001)) suggesting an additional potential for disease modification.

The α7 receptor forms functional homomeric ligand-gated ion channels that promote rapidly desensitizing $Ca^{2+}$ influx, is widely expressed throughout the mammalian brain, and has been implicated in sensory gating, cognition, and neuroprotection (Sco, J., et al., *Biol Psychiatry* 49(3):240–7 (2001). Nicotine-induced neuroprotection against β-Amyloid-induced toxicity is suppressed by α-Bgt and a selective α7-nAChR agonist, anabaseine-derived 3-(4)-dimethylaminocinamylidine (DMAC) exerts cytoprotective effects (De Fiebre C. M., et al., *Mol. Pharmacol.* 47:164–171 (1995); Kem W R., *Behav Brain Res.* 113(1–2):169–81 (2000)). The level of phosphorylated Akt, an effector of PI-3-K, is increased by nicotine and cytoprotective effects are suppressed by phosphatidylinositol 3-kinase (PI3K) inhibitors (LY294002 and wortmannin), and Src inhibitor (PP2) (Kihara, T., et al., *J. Biol. Chem.* 276:13541–13546 (2001)). The α7-nAChR transduces signals to PI3K in a cascade, which ultimately contributes to a neuroprotective effect against Aβ.

In contrast to the decrease in α7-nAChR, the angiotensin converting enzyme (ACE—the enzyme that converts Angiotensin I to Angiotensin II) density is increased in the temporal cortex from patients with Alzheimer's disease (Barnes, N. M., et al., *Eur. J. Pharmacol.* 200:289–292 (1991)), and the ACE genotype is associated with AD in some populations (Narain Y et al., *J Med Genet.*, 37(9): 695–7 (2000)). AT2 receptors exert growth inhibitory effects or apoptosis both in cultured cells and in vivo (Horiuchi, M., et al., *Endocr. Res.* 24:307–314 (1998)), are expressed in PC12 cells, and have been shown to inhibit the JAK/STAT signaling cascade (Horiuchi, M., et al., *Circ. Res.* 84:876–882 (1999)).

It would be desirable to further understand any relationships between α7 nAChR-mediated beneficial pathways and the apoptotic effects mediated by AT2, in order to maximize cell survival by modulation of nAChR and/or AT2 activity.

It would also be desirable to further understand any relationship between Aβ-mediated toxicity and signaling pathways affected by nicotinic receptors. For example, further elucidation of these relationships can provide for discovery of therapeutic compositions useful in mitigating the effects of Alzheimer's Disease.

SUMMARY OF THE INVENTION

The present invention provides a method of determining substances that stimulate or inhibit nicotine receptors. The invention also provides for enhancement of effects of substances that stimulate nicotine receptor activity mediated by phosphorylation of the Janus-Activated Kinase 2 (JAK2).

The present inventors have shown that antagonists of the angiotensin II, type 2 (AT2) receptor (or inhibitors of substances that stimulate the AT2 receptor) enhance the effects of nicotinic stimulatory substances by reducing or eliminating AT2-mediated interference with nicotine receptor-induced phosphorylation of JAK2. Further, the inventors have shown that nicotinic protection against the effects of β-amyloid-mediated toxicity operates via JAK2 phosphorylation. Methods and compositions for prophylaxis and/or treatment, and screening assays, including assays adapted for high-throughput screening (HTS), are provided.

Accordingly, in one aspect, the invention relates to a method of screening for a substance or for substances having an effect on a nicotine receptor. The method comprises contacting a cell having a nicotine receptor with a test compound; and determining any increase or decrease in phosphorylation of JAK2.

In another aspect, the invention relates to a method of screening for a substance that increases or decreases an effect of a substance that stimulates a nicotine receptor to The method comprises contacting a cell having a nicotine receptor with the substance that stimulates a nicotine receptor; contacting the cell with a test substance; and determining any increase or decrease in phosphorylation of JAK2 in the presence of the test substance relative to a level of JAK2 phosphorylation measured when the cell is in contact with a substance that stimulates a nicotine receptor in the absence of the test substance.

In yet another aspect, the invention relates to a method of screening for a substance that inhibits or stimulates an AT2 receptor and/or impairs or enhances the effect of a substance that mediates an effect on the AT2 receptor. The method comprises contacting a cell having a nicotine receptor and an AT2 receptor with a substance that stimulates the nicotine receptor; contacting the cell with a test substance; and determining any increase or decrease in phosphorylation of JAK2 in the presence of the test substance relative to a level of JAK2 phosphorylation measured when the cell is in contact with the substance that stimulates the nicotine receptor in the absence of the test substance. An increase in JAK2 phosphorylation indicates that the test substance inhibits the AT2 receptor, impairs the effect of a substance that stimulates the AT2 receptor, or enhances the effect of a substance that inhibits the AT2 receptor. A decrease in JAK2 phosphorylation indicates that the test substance stimulates the AT2 receptor, enhances the effect of a substance that stimulates the AT2 receptor, or impairs the effect of a substance that inhibits the AT2 receptor.

In yet another aspect, the invention relates to a method of decreasing apoptosis in cells comprising a nicotine receptor and an AT2 receptor. The method comprises contacting the cells with a substance that stimulates a nicotine receptor and either or both of an inhibitor of the AT2 receptor or an inhibitor of a substance that stimulates the AT2 receptor.

In yet another aspect, the invention relates to a method of decreasing apoptosis in cells comprising a nicotine receptor and an AT2 receptor. The method comprises contacting the cells with a substance that stimulates the nicotine receptor; and contacting the cell with either or both of an inhibitor of the AT2 receptor or an inhibitor of a substance that stimulates the AT2 receptor.

In yet another aspect, the invention relates to a method of treatment and/or prophylaxis for subjects suffering from a central nervous system disorder mediated by a nicotine receptor. The method comprises administering an effective amount of a pharmaceutical composition including either or both of at least one inhibitor of the AT2 receptor or at least one inhibitor of a substance that stimulates the AT2 receptor; a substance that stimulates a nicotine receptor; and a pharmaceutically acceptable carrier. The amount of the pharmaceutical composition is effective to stimulate the nicotine receptor.

In still another aspect, the invention relates to a pharmaceutical composition for treatment and/or prophylaxis of a central nervous disorder for administration to a subject suffering from the disorder. The composition comprises either or both of at least one inhibitor of the AT2 receptor or at least one inhibitor of a substance that stimulates the AT2 receptor; a substance that stimulates a nicotine receptor; and a pharmaceutically acceptable carrier.

The invention also provides methods and compositions related to the interaction of β-amyloid and nicotinic receptors. Accordingly, in one aspect, the invention relates to a method of screening for substances that have an effect on β-amyloid-associated neurotoxicity mediated by binding of a β-amyloid peptide, polypeptide or protein to a nicotinic receptor. The method comprises contacting a cell having a nicotine receptor with a β-amyloid polypeptide and determining a level of Janus-Activated Kinase 2 (JAK2) phosphorylation; and contacting the cell with a test substance and determining any increase or decrease in phosphorylation of JAK2.

In another aspect, the invention also relates to a method of screening for substances that decrease the neurotoxicity of β-amyloid polypeptides mediated by binding of a β-amyloid polypeptide to a nicotinic receptor. The method comprises contacting a cell having a nicotine receptor with a β-amyloid polypeptide and determining a level of Janus-Activated Kinase 2 (JAK2) phosphorylation; and contacting the cell with a test substance and determining any increase or decrease in phosphorylation of JAK2. Any increase in JAK2 phosphorylation indicates that the test substance decreases the neurotoxicity of β-amyloid peptides.

In another aspect, the invention relates to a method of preventing or decreasing apoptosis in cells having nicotinic receptors comprising contacting the cells with a substance that increases phosphorylation of JAK2. The apoptosis can be that associated with β-amyloid-mediated toxicity.

In another aspect, the invention relates to a method of prophylaxis and/or treatment of neurodegeneration associated with Alzheimer's disease comprising administering a therapeutically effective amount of a substance that increases phosphorylation of JAK2.

In yet another aspect, the invention relates to a composition for rophylaxis and/or treatment of neurodegeneration associated with Alzheimer's disease comprising a therapeutically effective amount of a substance that increases phosphorylation of JAK2.

DETAILED DESCRIPTION OF THE INVENTION

Figure 1:
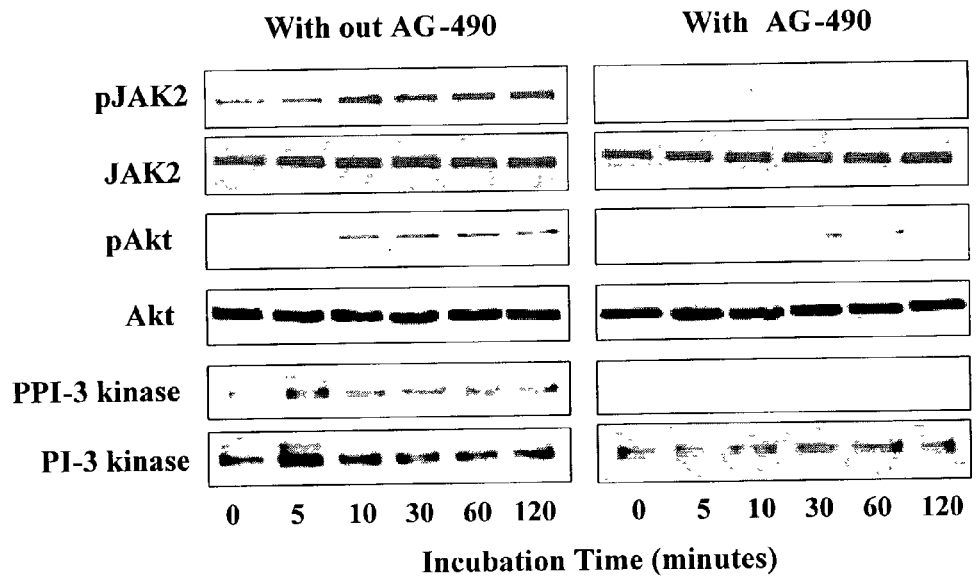
FIG. 1 shows the effects of the JAK2 inhibitor AG-490 on the nicotine-induced tyrosine phosphorylation of JAK2 and PI-3 kinase plus serine phosphorylation of Akt in PC12 cells. PC12 cells, pre-incubated for 1 hour in the presence or absence of the JAK2 inhibitor AG-490 at 10 μM, were stimulated with nicotine (10 μM) for various times (0, 5, 10, 30, 60, and 120 min). Cells were either lysed and immunoblotted with phospho-specific and nonphosphospecific anti-JAK2 and anti-Akt antibodies or lysed and immunoprecipitated with anti-PI-3 kinase antibody. The PI-3 kinase immunoprecipitated proteins were then immunoblotted with anti-phosphotyrosine and anti-PI-3 kinase antibodies. Results shown are representative of three experiments.

The present invention provides screening assays, including high throughput methods, for detecting substances that stimulate or inhibit (directly or indirectly) nicotine receptors. Such factors can be detected and characterized for α7 nicotine receptors. Measuring tyrosine phosphorylation of the Janus Activated Kinase 2 (JAK2) allows detection of stimulation or inhibition of the nicotine receptor. Further, screening assays are provided that allow detection and characterization of substances that stimulate or inhibit (directly or indirectly) the AT2 receptor. Methods are also provided for decreasing apoptosis and increasing the effects of substances that stimulate nicotine receptors.

In some instances, it may be desirable to perform either preliminary or subsequent screening analysis to determine whether a test substance is exerting an inhibitory effect on an apoptotic pathway (e.g., the AT2 or Aβ pathways) or a stimulatory effect on a survival pathway (e.g., the nicotinic pathway). For example, individual ligands may be tested to rule out either pathway through competitive binding assays using selective agonists or antagonists. The screening assays of the invention do not necessarily requires such additional determinations, however, and desired evaluation of a test substance can be accomplished without further screening.

The present invention also demonstrates a direct interaction of the β-amyloid peptide with the α7 nicotinic acetylcholine receptor (α7-nAChR). Further, the molecular mechanisms of nAChR-mediated neuroprotection are demonstrated to involve a JAK2 phosphorylation signal cascade. Nicotine-stimulation of α7-nAChR results in an initial increase in levels of phosphorylated tyrosine kinase Janus-Activated Kinase-2 (JAK2) and subsequent phosphorylation of PI-3 kinase, and Akt. These effects are blocked by preincubation with the JAK2 specific inhibitor AG-490 and by α-Bgt. The α7-nAChR co-precipitates with phosphorylated JAK2 and this effect and the neuroprotective effect of nicotine on Aβ toxicity are reversed by AG-490. In the absence of nicotine, exposure to α-amyloid results in uncoupling to JAK2, induction of caspase-3, and induction of the DNA-repairing enzyme poly-(ADP-ribose)polymerase (PARP). This cascade is inhibited by nicotine through JAK2 phosphorylation. These findings suggest that the α7-nAChR transduces signals to PI3K and Akt via JAK2 in a cascade that results in neuroprotection. A negative feed back regulation between the α7-nAChR and β-amyloid-induced cell death is mediated through JAK2 phosphorylation. Nicotine-stimulated JAK2 and its neuroprotective effects can be prevented through activation of AT2 receptors. Accordingly, the present inventors have identified novel mechanisms of receptor interactions relevant to neuronal viability. Such mechanisms provide novel therapeutic strategies for optimizing neuroprotection.

The methods and compositions of the invention can be selective for the α7nAChR. This aspect of the invention can provide for selective enhancement of α7-mediated activity, thereby allowing the beneficial effects as described herein to be achieved with a low incidence of side effects, e.g. those side effects mediated primarily by non-α7 receptor subtypes. In order to achieve the benefits of this aspect of the invention, the selectively of binding to α7 receptors can be from about 10- to about 100-fold greater than to another receptor subtype. Further, the selectivity can be from about 100- to about 1000-fold greater for α7-nAChR. As will be recognized, selectivity can also be established by evaluating functional stimulation or inhibition, e.g. by measuring JAK2 phosphorylation according to the invention.

Methods for the prophylaxis and/or treatment of central nervous system disorders are also provided, as are pharmaceutical compositions useful in such methods.

As used herein the following terms have the meanings indicated:

An "agonist" is a substance that stimulates its binding partner, typically a receptor. Stimulation is defined in the context of the particular assay, or may be apparent in the literature from a discussion herein that makes a comparison to a factor or substance that is accepted as an "agonist" or "partial agonist" of the particular binding partner by those of skill in the art. Stimulation may be defined with respect to an increase in a particular effect or function that is induced by interaction of the agonist or partial agonist with a binding partner and can include allosteric effects.

An "antagonist" is a substance that inhibits its binding partner, typically a receptor. Inhibition is defined in the context of the particular assay, or may be apparent in the literature from a discussion herein that makes a comparison to a factor or substance that is accepted as an "antagonist" of the particular binding partner by those of skill in the art. Inhibition may be defined with respect to an decrease in a particular effect or function that is induced by interaction of the agonist with a binding partner, and can include allosteric effects.

Herein, the terms Aβ, Aβ peptide(s), β-amyloid, amyloid β, and amyloid refer to any species of peptide, polypeptide, or protein associated with the amyloid characteristic of Alzheimer's Disease. The term "Aβ (1–42)" contemplates the 42 amino acid β-amyloid protein, but also includes fragments thereof that can bind to or mediate an effect through an nicotinic receptor.

The term "α7 nAChR" refers to homopentameric nicotinic acetylcholine receptors reported to be involved in cognition and neuroprotection both in animals and human. These effects are shared by the heteropentamer α4β2 which is also widely expressed in human brain (reviewed in Bencheri, M. and J. D. Schmitt, *Current Drug Targets* Volume 1, number 4, August 2002; pp 349–357—also see entire issue, which is dedicated to nicotinic receptor distribution and effects (e.g., α4β2 and α7)). Accordingly, the terms "nAChR" and "nicotine receptor," as used herein, encompass such receptors comprising these subunits.

As used herein, "PC12" refers to the rat adrenal chromaffin tumor cell line, PC12. This cell line, originally established by Greene and Tischler (Greene, L. A. and A. S. Tischler, Establishment of a noradrenergic clonal line of rat adrenal pheochromocytoma cells which respond to nerve growth factor. *Proc Natl Acad Sci USA*, 73(7):2424–8(1976), has been utilized frequently in the study of neuronal acetylcholine receptors, including α7 nAChR (See, e.g., Patrick, J. and W. B. Stallcup, Immunological distinction between acetylcholine receptor and the alpha-bungarotoxin-binding component on sympathetic neurons. *Proc Natl Acad Sci USA.*, 74(10):4689–92(1977); Whiting, et al., Functional acetylcholine receptor in PC12 cells. *Nature* 327:515–518 (1987); Cooper, S. T. and N. S. Millar, Host cell-specific folding and assembly of the neuronal nicotinic acetylcholine receptor alpha7 subunit. *J Neurochem.* 68(5):2140–51 (1997), all fully incorporated herein by reference). The angiotensin receptor subtype II (AT2) has also been expressed in PC12 cells (see, e.g., Wolf, G., et al., Angiotensin II's antiproliferative effects mediated through AT2-receptors depend on down-regulation of SM-20. *Lab Invest.* 82(10):1305–17 (2002); and Lehtonen, J. Y., et al., Analysis of functional domains of angiotensin II type 2 receptor involved in apoptosis. *Mol Endocrinol.* 13(7):1051–60(1999), all fully incorporated herein by reference). The PC12 cell line is very well-known and has been deposited, for example, with the American Type Culture Collection under ATCC Number: CRL-1721.

Various nucleic acid sequences encoding nAChRs are available, including for α7 (See, e.g., Chini, B., et al., Molecular cloning and chromosomal localization of the human alpha7-nicotinic receptor subunit gene (CHRNA7), *Genomics* 19(2): 379–381 (1994); ACCESSION NM_000746, version NM_000746.2 GI:21536283, fully incorporated herein by reference).

Nucleic acid sequences encoding AT2 receptors are also known, and guidance regarding expression cloning is available in the literature (see, e.g., Mukoyama, M., et al., Expression cloning of type 2 angiotensin II receptor reveals a unique class of seven-transmembrane receptors. *J Biol. Chem.* 268(33):24539–42 (1993); Nakajima, M., et al., Cloning of cDNA and analysis of the gene for mouse angiotensin II type 2 receptor. *Biochem Biophys Res Commun.* 197(2):393–9(1993); and Nakajima, M., et al., The angiotensin II type 2 (AT2) receptor antagonizes the growth effects of the AT1 receptor: gain-of-function study using gene transfer. *Proc Natl Acad Sci USA.* 92(23):10663–7 (1995); Homo sapiens angiotensin receptor 2 (AGTR2), mRNA, ACCESSION XM_030897, version XM_030897.2 GI:22058388, all fully incorporated herein by reference).

Of course, other cells lines exist and may be prepared that are suitable for the methods of the present invention. For example, the human neuroblastoma cell line SH-SY5Y are also "α7-permissive" and may be used with α7-specific methods according to the present invention (see, e.g., Cooper, S. T. and N. S. Millar, *J Neurochem.* 68(5):2140–51 (1997)). Other cells lines may be appropriate, depending on the subtype of nAChR being evaluated.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, INC.), PCR 2: A PRACTICAL APPROACH (M. J. McPherson, B. D. Hames and (G. R. Taylor eds., 1995); ANIMAL CELL CULTURE (R. I. Freshney. Ed., 1987); and ANTIBODIES: A LABORATORY MANUAL (Harlow et al. eds., 1987), all fully incorporated herein by reference.

Accordingly, in one aspect, the present invention relates to a method of screening for substances having an effect on a nicotine receptor by contacting a cell having a nicotine receptor with a test substance; and determining any increase or decrease in phosphorylation of Janus-Activated Kinase 2 (JAK2). An increase in phosphorylation of JAK2 indicates that the test substance stimulates the nicotine receptor, and a decrease in phosphorylation of JAK2 indicates that the test substance inhibits the nicotine receptor. The test substance can be a member of a library of test substances, and the library can be a combinatorial chemical library, a peptide, polypeptide, nonpeptidal peptidominetic, an antibody, or small molecule organic compound library. The library can also be a random combination of compounds. The test substances can be screened by high throughput screening.

In another aspect, the invention relates to a method of screening for a substance that increases or decreases an effect of a substance that stimulates a nicotine receptor by contacting a cell having a nicotine receptor with the substance that stimulates a nicotine receptor; contacting the cell with a test substance; and determining any increase or decrease in phosphorylation of JAK2 in the presence of the test substance relative to a level of JAK2 phosphorylation measured when the cell is in contact with a substance that stimulates a nicotine receptor in the absence of the test substance. An increase in JAK2 phosphorylation indicates that the test substance increases the effect of the substance that stimulates a nicotine receptor on the nicotine receptor; and a decrease in JAK2 phosphorylation indicates that the test substance decreases the effect of the substance that stimulates a nicotine receptor on the nicotine receptor.

In another aspect, the invention relates to a method of screening for substance that inhibits or stimulates an AT2 receptor, by contacting a cell having a nicotine receptor and an AT2 receptor with a substance that stimulates the nicotine receptor; contacting the cell with a test substance; and determining any increase or decrease in phosphorylation of JAK2 in the presence of the test substance relative to a level of JAK2 phosphorylation measured when the cell is in contact with the substance that stimulates the nicotine receptor in the absence of the test substance. An increase in JAK2 phosphorylation indicates that the test substance inhibits the AT2 receptor; and a decrease in JAK2 phosphorylation indicates that the test substance stimulates the AT2 receptor. Any effect of the test substance on the nicotine receptor in the absence of the AT2 receptor is predetermined and any increase or decrease in JAK2 phosphorylation is determined relative to any JAK2 phosphorylation related to such effects. The test substance can be a member of a library of test substances, and the library is a combinatorial chemical library, a peptide, polypeptide, nonpeptidal peptidominetic, an antibody, or small molecule organic compound library. The library can also be a random combination of compounds. The test substance can be screened by high throughput screening.

In another aspect, the invention relates to a method of screening for a substance that impairs or enhances the effect of a substance that stimulates the AT2 receptor by contacting a cell having a nicotine receptor and an AT2 receptor with a substance that stimulates the nicotine receptor and a substance that stimulates the AT2 receptor; contacting the cell with a test substance; and determining any increase or decrease in phosphorylation of JAK2 in the presence of the test substance relative to a level of JAK2 phosphorylation measured when the cell is in contact with the substance that stimulates the nicotine receptor and the substance that stimulates the AT2 receptor in the absence of the test substance. An increase in JAK2 phosphorylation indicates that the test substance impairs the effect of the substance that stimulates the AT2 receptor, or enhances the effect of the substance that inhibits the AT2 receptor; and a decrease in JAK2 phosphorylation indicates that the test substance enhances the effect of the substance that stimulates the AT2 receptor, or impairs the effect of the substance that inhibits the AT2 receptor.

In another aspect, the invention relates to a method of screening for substances that have an effect on β amyloid-associated neurotoxicity mediated by a nicotinic receptor by contacting a cell having a nicotine receptor with a β amyloid peptide and determining a level of Janus-Activated Kinase 2 (JAK2) phosphorylation; and contacting the cell with a test substance and determining any increase or decrease in phosphorylation of JAK2. An increase in JAK2 phosphorylation indicates that the test substance is a candidate substance for further evaluation as a substance capable of decreasing β amyloid-associated neurotoxicity.

In another aspect, the invention relates to a method of screening for substances that decrease the neurotoxicity of β amyloid peptides mediated by a nicotinic receptor by contacting a cell having a nicotine receptor with a β amyloid peptide and determining a level of Janus-Activated Kinase 2 (JAK2) phosphorylation; and contacting the cell with a test substance and determining any increase or decrease in phosphorylation of JAK2. Any increase in JAK2 phosphorylation indicates that the test substance decreases the neurotoxicity of β amyloid peptides.

In another aspect, the invention relates to a method of increasing an effect of a substance that stimulates a nicotine receptor in cells comprising a nicotine receptor and an AT2 receptor by contacting the cells with a substance that stimulates the nicotine receptor; and contacting the cell with a substance selected from the group consisting of an inhibitor of the AT2 receptor and an inhibitor of a substance that stimulates the AT2 receptor.

In another aspect, the invention relates to a method of decreasing apoptosis in cells comprising a nicotine receptor and an AT2 receptor by contacting the cells with a substance that stimulates a nicotine receptor; and contacting the cells with a substance selected from the group consisting of an inhibitor of the AT2 receptor and an inhibitor of a substance that stimulates the AT2 receptor. Increased cell survival can indicate a decrease in apoptosis. A decrease in apoptosis can also be indicated by an observation of decreased poly-(ADP-ribose)polymerase (PARP) activity, decreased caspase 3 activity, or induction of Bcl2.

In another aspect, the invention relates to a method of treatment or prophylaxis for subject suffering from a central nervous system disorder mediated by a nicotine receptor by administering an amount of a pharmaceutical composition comprising a substance that stimulates a nicotine receptor; either or both of at least one inhibitor of the AT2 receptor or at least one inhibitor of a substance that stimulates the AT2 receptor; and a pharmaceutically acceptable carrier. The amount of the pharmaceutical composition is effective to stimulate the receptor.

In another aspect, the invention relates to a method of treating neurodegeneration associated with Alzheimer's disease by administering an therapeutically effective amount of a substance that increases tyrosine phosphorylation of JAK2.

In another aspect, the invention relates to a method of treatment or prophylaxis of neurodegeneration associated with Alzheimer's disease by administering an amount of a pharmaceutical composition comprising a substance that stimulates a nicotine receptor; either or both of at least one inhibitor of the AT2 receptor or at least one inhibitor of a substance that stimulates the AT2 receptor; and a pharmaceutically acceptable carrier. The amount of the pharmaceutical composition is effective to stimulate the receptor.

In another aspect, the invention relates to a pharmaceutical composition for treatment or prophylaxis of a central nervous disorder for administration to a subject suffering from the disorder, comprising a substance that stimulates a nicotine receptor; and either or both of at least one inhibitor of the AT2 receptor or at least one inhibitor of a substance that stimulates the AT2 receptor; and a pharmaceutically acceptable carrier. The substance that stimulates a nicotine receptor can be a cholinergic ligand, nicotinic agonist, or an acetylcholinesterase inhibitor. The substance that stimulates a nicotine receptor can also be selective for α7-nAChR. The substance selective for α7-nAChR can be a substituted quinuclidine compound. The substance can also be represented by a formula selected from the group consisting of I, II, and III:

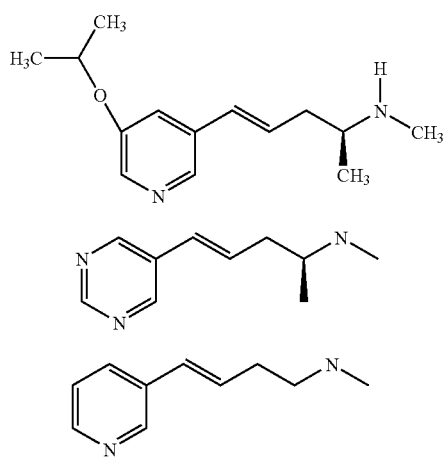

The substance that inhibits the AT2 receptor or that inhibits of a substance that stimulates the AT2 receptor can be a substance that inhibits a substance that stimulates AT2, including, for example, an angiotensin II converting enzyme (ACE) inhibitor.

In another aspect, the invention relates to a pharmaceutical composition for treatment or prophylaxis of a neurodegenerative disorder for administration to a subject suffering from the disorder, comprising a substance that stimulates a nicotine receptor; and either or both of at least one inhibitor of the AT2 receptor or at least one inhibitor of a substance that stimulates the AT2 receptor; and a pharmaceutically acceptable carrier. The substance that stimulates a nicotine receptor can be a cholinergic ligand, nicotinic agonist, or an acetylcholinesterase inhibitor. The substance that stimulates a nicotine receptor can be selective for α7-nAChR. The substance selective for α7-nAChR can be a substituted quinuclidine compound. The substance that stimulates a nicotine receptor can be represented by a formula selected from the group consisting of I, II, and III:

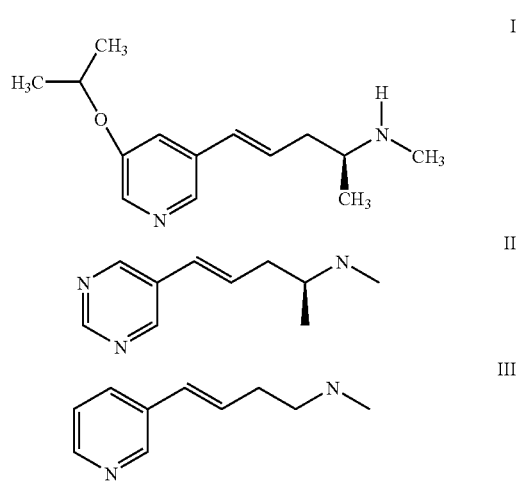

The substance that inhibits the AT2 receptor or that inhibits a substance that stimulates the AT2 receptor can be a substance that inhibits a substance that stimulates AT2, for example, an angiotensin II converting enzyme (ACE) inhibitor. The substance that inhibits the AT2 receptor or that inhibits a substance that stimulates the AT2 receptor is a substance that stimulates AT2. The substance that stimulates AT2 can be PD123177 and/or PD123319.

Figure 2:
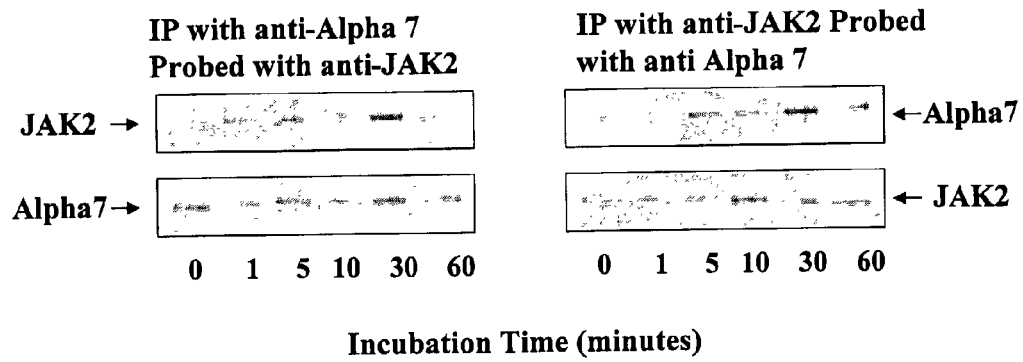
FIG. 2 shows Western blot analysis illustrating the effect of nicotine on the JAK2 complex formation with the α7 receptor in PC12 cells. PC12 cells were stimulated with nicotine (10 μM) for various times (0, 1, 5, 10, 30, and 60 min). Cells were lysed, and JAK2 was immunoprecipitated from lysates (1 mg of protein) with an anti-JAK2 antibody. Immunoprecipitates were then immunoblotted with an anti-α7 antibody. Similar results were obtained in three experiments.

Nicotine and the JAK/STAT pathway in neuronal signaling. Nicotine activates the growth promoting enzyme Janus-Activated Kinase 2 (JAK2) in PC12 cells. Pre-incubation of these cells with the JAK2 specific inhibitor AG490 (see Kumano, K., A. et al., *Biochem. Biophys. Res. Commun.* 270: 209–214 (2000)) blocks the nicotine-induced activation of PI3K and Akt (FIG. 1). Moreover, nicotine also induces a complex between JAK2 and the α7 receptor (FIG. 2). These results provide direct evidence for linkages between JAK2 and the nicotine-induced activation of the PI3K cascade in PC12 cells.

Effects of the JAK2 inhibitor AG-490 on the nicotine-induced tyrosine phosphorylation of JAK2 and PI-3 kinase and serine phosphorylation of Akt in PC12 cells. JAK2 is tyrosine phosphorylated in response to nicotine within 5 to 10 min and this activation remains above basal levels even after longer exposure (120 min) to nicotine (FIG. 1). The JAK2 inhibitor AG-490 inhibits the basal and nicotine-stimulated JAK2 tyrosine phosphorylation, the tyrosine phosphorylation of PI-3K and the serine phosphorylation of Akt (FIG. 1). Similar results are observed in the human cell line SH-SY5Y. These results suggest that JAK2 activation by nicotine precedes the activation of PI-3K and its effector Akt. JAK2 activation is completely prevented by pre-incubation of a-bungarotoxin, indicating a receptor-mediated effect (FIG. 3).

Effects of Nicotine on the JAK2 complex formation with the α7 receptor. To test the hypothesis that JAK2 interacts directly with α7-nAChR, immuno-precipitation studies were conducted using a rabbit polyclonal anti-JAK2 antibody. Cultured PC12 cells were stimulated with nicotine (10 µM) for various times, lysed, and JAK2 was immunoprecipitated with anti-JAK2 antibody. Immunoprecipitated proteins were separated by gel electrophoresis, transferred to nitrocellulose, and immunoblotted with anti-α7 antibodies. As shown in FIG. 2, nicotine induced a rapid association of JAK2 with the α7 receptor within 5 min. This time course of α7-receptor association with JAK2 is similar to that of the nicotine-induced activation of JAK2 (FIG. 1). Identical results were also obtained when the experiments were repeated using anti-α7 receptor antibody to immunoprecipitate the receptor and probing the Western blot with the anti-JAK2 antibody.

Effects of Ang II pretreatment with or without Ang II receptor antagonists on nicotine-induced activation of JAK2. Ang II exerts its biological effects via the activation of two different receptors known as AT1 and AT2 receptors both belonging to the G protein-coupled receptor family (Horiuchi, M., W. et al., *Circ. Res.* 84: 876–882 (1999)). The AT1 receptor stimulates proliferation, whereas the AT2 receptor exerts growth inhibitory effects both in cultured cells, among others PC12 cells, as well as in vivo (Gallinat, S., S., et al., *FEBS Lett.* 443: 75–79 (1999)). In addition, it has also been reported that the angiotensin converting enzyme density is increased in the temporal cortex from patients with Alzheimer's disease (Barnes, N. M., et al., *Eur. J. Pharmacol.* 200:289–292 (1991)). Pre-incubation of PC12 cells with angiotensin II (Ang II) blocks the nicotine-induced activation of JAK2 via the AT2 receptor (FIG. 3).

Figure 3:
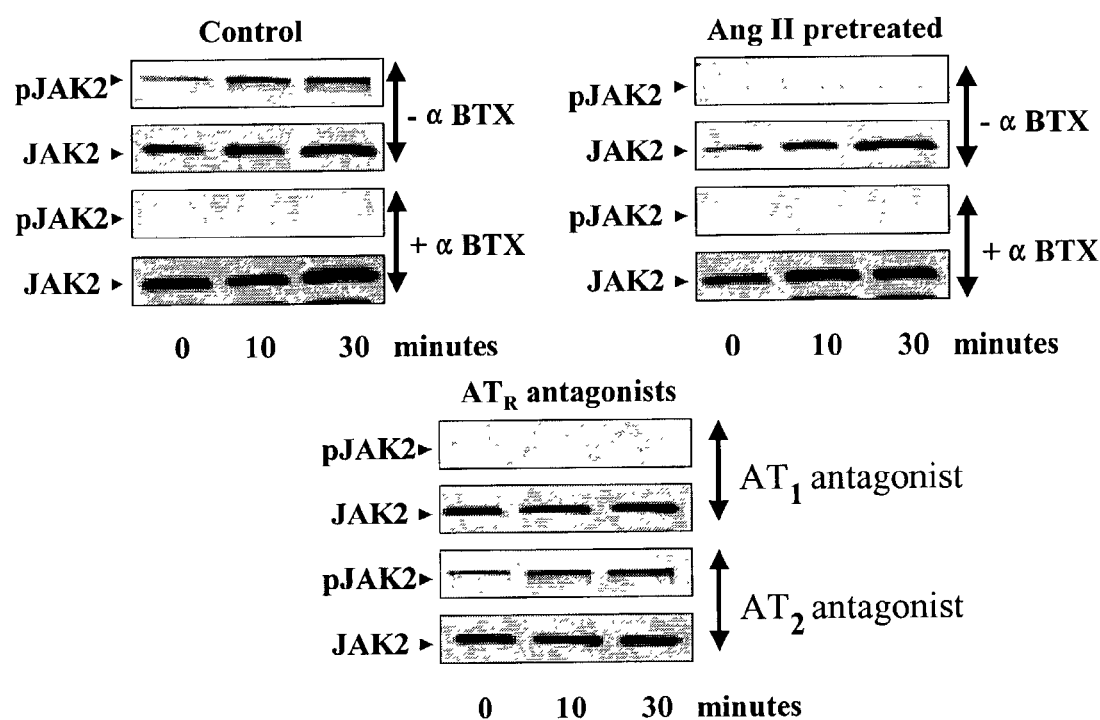
FIG. 3 shows effects of Ang II pretreatment with or without Ang II receptor antagonists on the nicotine-induced activation of JAK2 in PC12 cells. PC12 cells, pre-incubated for 8 hours in the presence or absence of Ang II at 100 nM with or without 100 nM AT1 antagonist (candesartan), or 100 nM AT2 antagonist (PD 123177), were stimulated with nicotine (10 μM) for various times (0, 10, and 30 min). Cells were either lysed and immunoblotted with phospho-specific and nonphospospecific anti-JAK2. Results shown are representative of three experiments.

Preincubation of PC12 cells with Ang II blocks the nicotine-induced tyrosine phosphorylation of JAK2 via the AT2 receptor (FIG. 3). This inhibition is completely prevented by pre-incubation with an AT2 antagonist (PD 123177 at 100 nM), but not by an AT1 antagonist (candesartan at 100 nM), consistent with the receptor phenotype expressed in PC12 cells. This inhibition of nicotine-induced JAK2 phosphorylation was accompanied by a complete reversal of nicotine-induced neuroprotection as shown by cell viability and by a nicotine-insensitive PARP induction.

Figure 8:
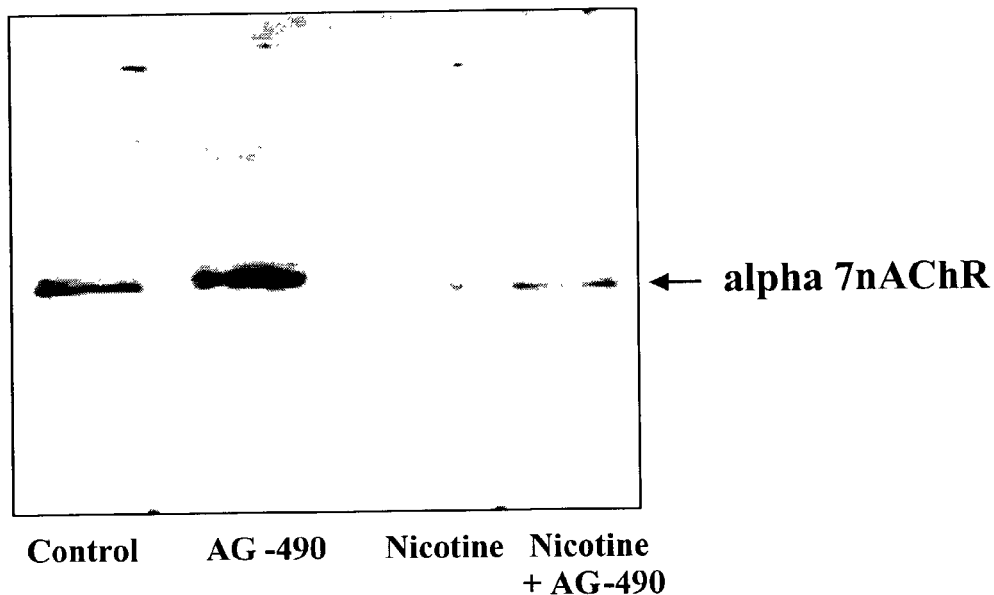
FIG. 8 shows Western blot analysis illustrating the co-immunoprecipitation of α7nAChR with Aβ(1–42) amyloid. Equal amounts of PC12 cells membrane proteins prepared from PC12 cells treated with Aβ(1–42) peptide at 10 μM for 5 minutes were immunoprecipitated with anti-Aβ(1–42) and subjected to Western analysis with anti-α7nAChR. Lane 1 are cells treated with Aβ(1–42) peptide alone, and lane 2 are cells treated with Aβ(1–42) peptide in the presence of AG-490 (10 μM). PC12 cells treated with Aβ(1–42) peptide at 10 μM in the presence of 10 μM nicotine with or with out AG-490 are shown in lanes 3 and 4 respectively.
Figure 9:
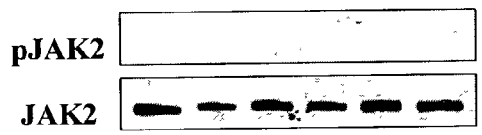
FIG. 9 shows Western blot analysis illustrating the effects of AG-490 on the Aβ(1–42) amyloid-induced phosphorylation of JAK2. PC12 cells, pre-incubated for 1 hour in the presence or absence of the JAK2 inhibitor AG-490 at 10 μM were stimulated with Aβ(1–42) amyloid peptide at 100 μM (A) or 1 μM (B) for various times (0, 5, 10, 30, 60, and 120 min). Cells were either lysed and immunoblotted with phospho-specific and nonphosphospecific anti-JAK2 antibodies. Results shown are representative of three experiments.
Figure 9:
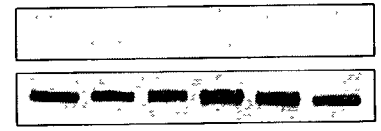
Figure 9:
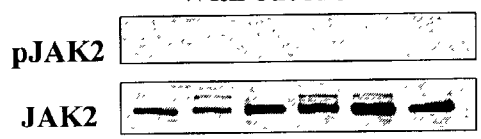
Figure 9:
Figure 10:
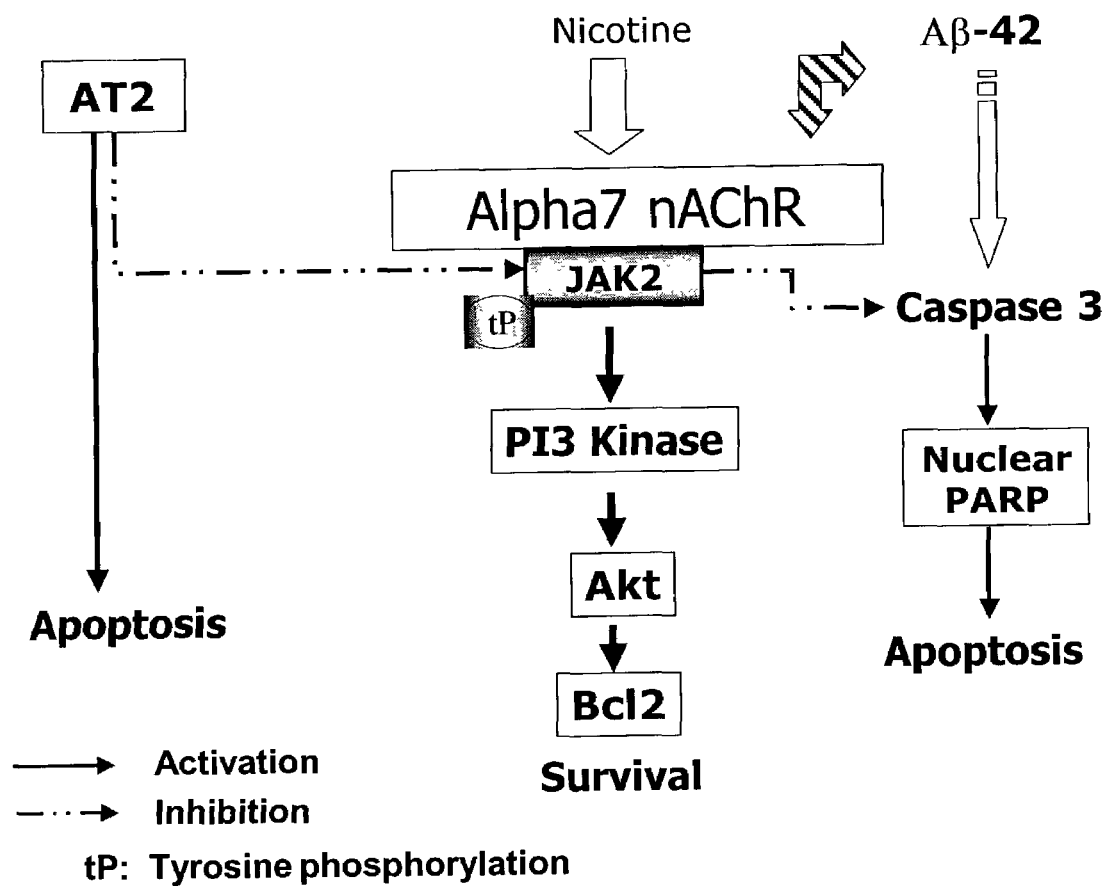
FIG. 10 is a schematic of the nicotine receptor mediated survival pathway, illustrating the relationship of this pathway to AT2- and Aβ-mediated apoptotic pathways.
Figure 11:
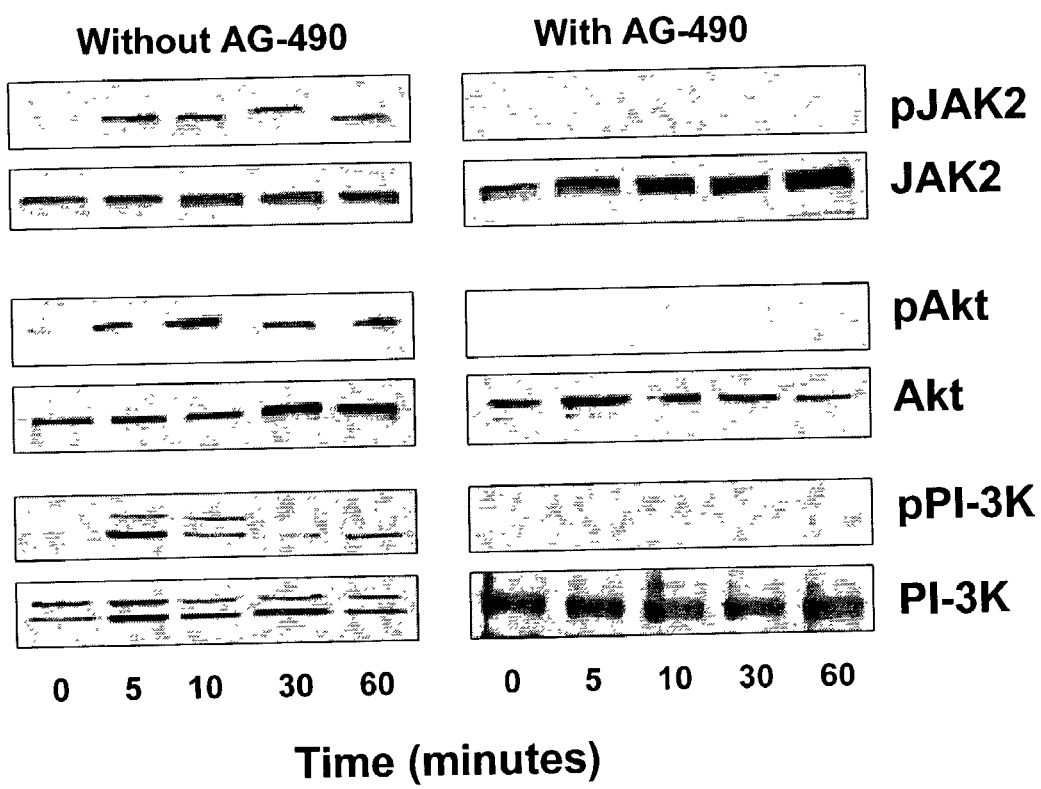
FIG. 11 shows Western blot analyses performed essential as indicated for FIG. 1, using compound TC-1698 and showing activation of JAK2, Akt, and PI-3 Kinase in PC12 cells, with suppression of activation in the presence of the JAK2 inhibitor AG-490.
Figure 12:
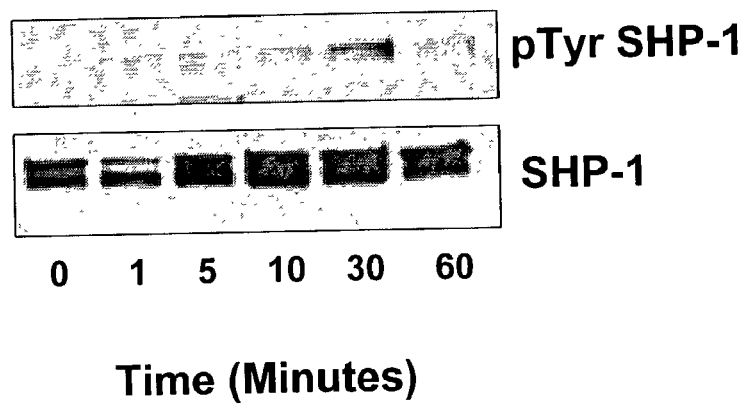
FIG. 12 illustrates angiotensin II-induced phosphorylation of SHP-1 in PC12 cells.
Figure 13:
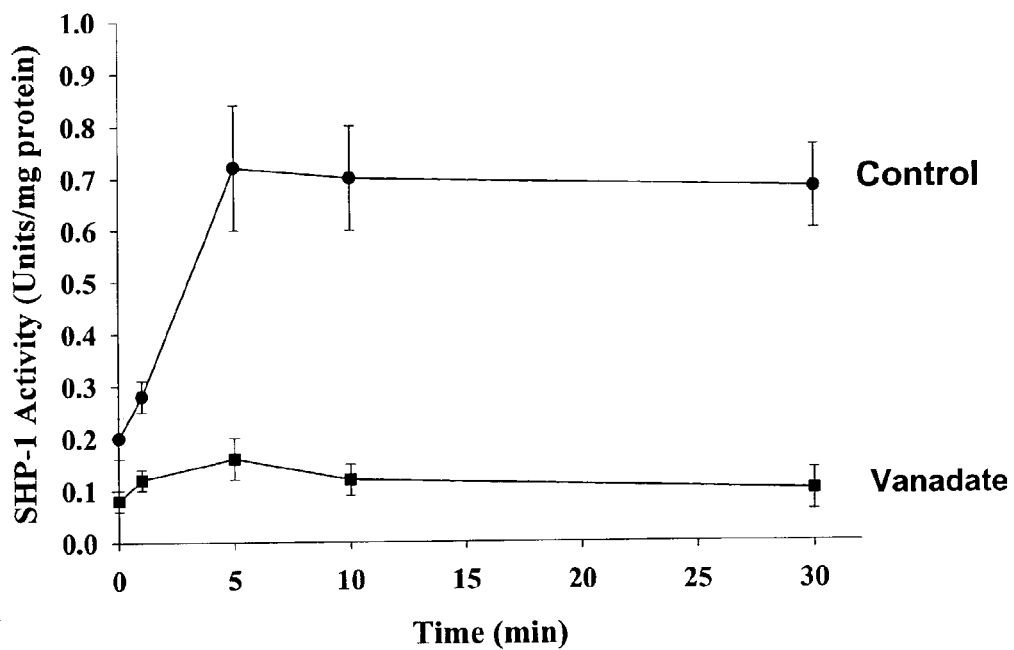
FIG. 13 illustrates the effect of the SHP-1 inhibitor vanadate on the angiotensin II-induced activation of SHP-1 in PC12 cells. (See Jiao, H., et al., *Mol Cell Biol* 16(12): 6985–921996), incorporated fully herein by reference, for unit definition of SHP-1 activity).
Figure 14:
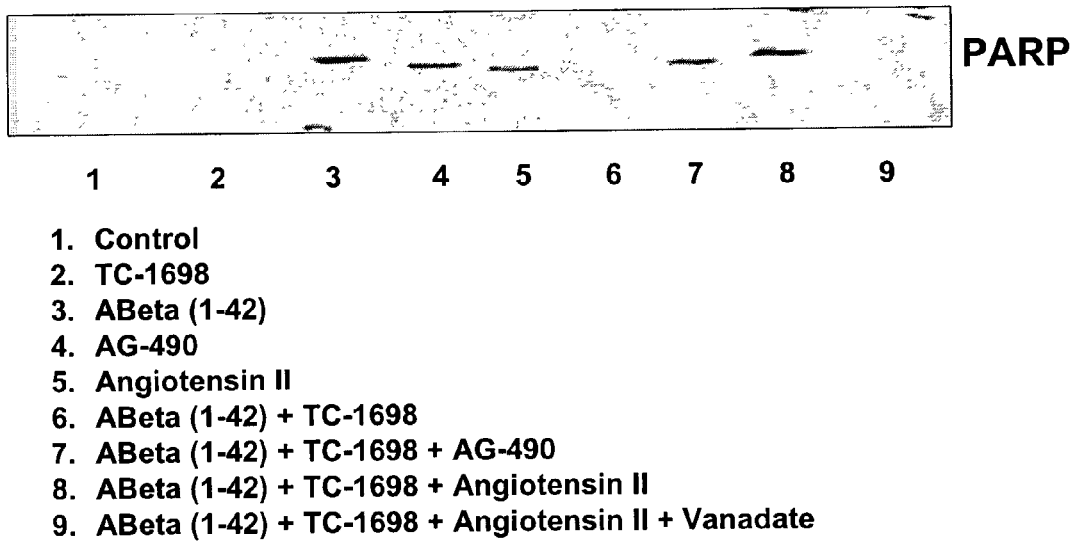
FIG. 14 illustrates the effects of the JAK2 inhibitor AG-490, and the SHP-1 inhibitor vanadate, on TC-1698-induced neuroprotection against Aβ (1–42) and angiotensin II-induced apoptosis (PARP is a marker for apoptosis—absence is, indicative of a neuoprotective effect, as indicated above and discussed herein).
Figure 15:
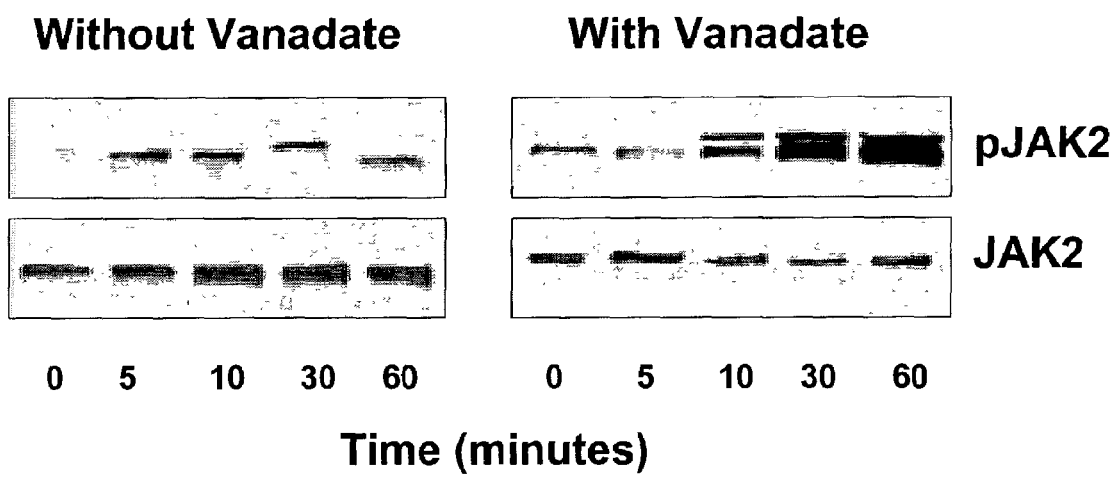
FIG. 15 shows the TC-1698-induced activation of JAK2 in PC12 cells, in the presence and absence of the SHP-1 inhibitor vanadate.

Co-immunoprecipitation of α7-nAChR with Aβ(1–42) amyloid and JAK2 phosphorylation. Recent studies have shown that Aβ(1–42) bind with high affinity to α7-nAChR and that this interaction can be inhibited by α7-nAChR antagonist. The studies leading to the present invention confirm the molecular association between Aβ(1–42) and α7-nAChR in cells treated with Aβ(1–42) (10 µM for 5 minutes) and immunoprecipitated with anti-Aβ(1–42) antibodies. Western analyses using anti-α7-nAChR antibodies identifies a 57 kDa protein reactive to anti-α7-nAChR which co-immunoprecipitates with endogenous Aβ(1–42) (FIG. 8). This effect is prevented by AG-490 pre-treatment of cells (FIG. 8). However, when cells were co-incubated with 10 µM nicotine, the complex formation between Aβ(1–42) and α7-nAChR was blocked even in the presence of AG-490 (FIG. 8). While not wishing to be bound by any particular theory, these results appear to suggest that the interaction between Aβ(1–42) and α7-nAChR can be inhibited by nicotine independently of JAK2. Pretreatment with Aβ(1–42) (0.1 µM to 1 µM) does not result in activation of JAK2 (FIGS. 9A and 9B) even at very high concentrations (e.g., at 10 µM and 100 µM, not shown in FIGS. 9A and 9B).

Figure 5:
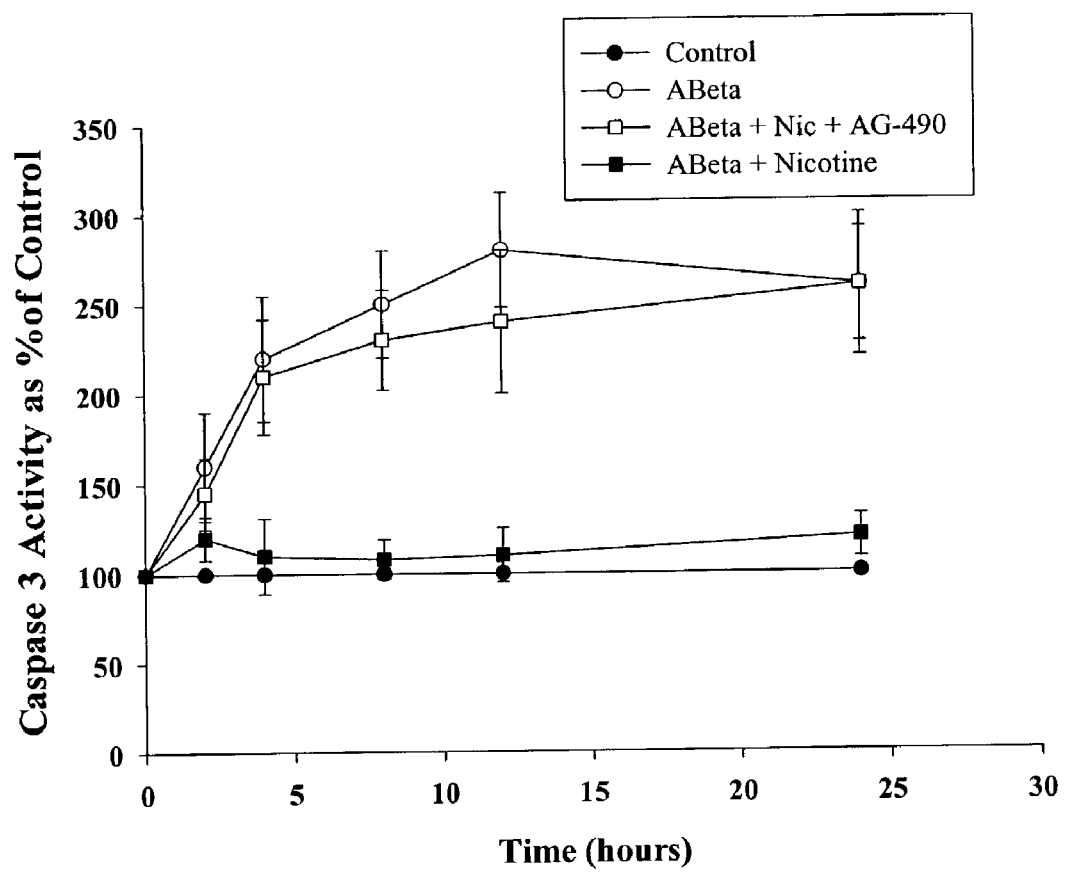
FIG. 5 is a graphic representation of the effects of JAK2 inhibitor AG-490 and nicotine on the Aβ(1–42) amyloid-induced activation of caspase 3 in PC 12 cells. PC 12 cells were incubated for 0, 2, 4, 8, 12, and 24 hours by Aβ(1–42) peptide at 100 nM in the presence or absence of nicotine at 10 μM and nicotine co-incubated with AG-490 (10 μM). Caspase 3 activities were determined as described in the Examples. Results represent the mean±SEM of three independent cultures. Aβ induced a significant increase in caspase 3 activity at 4, 8, 12 and 24 hours (*P<0.01) which was significantly inhibited by co-incubation with nicotine (** P<0.01). Nicotine, on the other hand, had no effect in the presence of AG-490.
Figure 6:
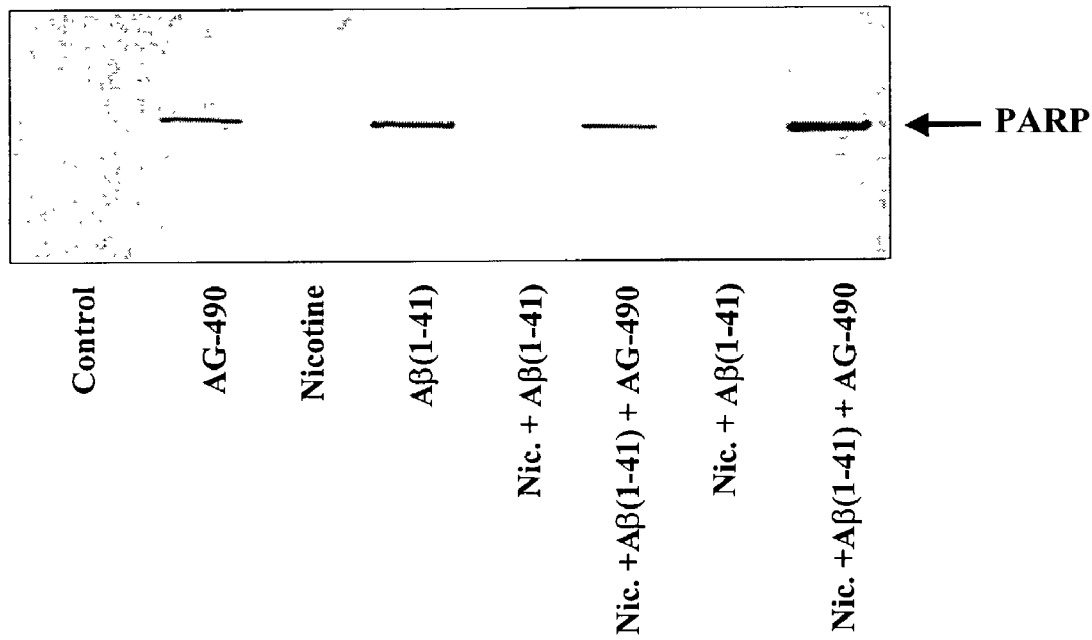
FIG. 6 shows Western blot analysis illustrating the effects of JAK2 inhibitor (AG-490) on nicotine protection against Aβ-induced apoptosis in PC12 cells. Poly-(ADP-ribose) polymerase (PARP) is marker of cells undergoing apoptosis. PARP expression was determined by Western analysis of PC12 cells nuclear extract treated for 8 hours by Aβ in the presence or absence of nicotine and/or AG-490.

Effects of nicotine on the Aβ(1–42)-induced apoptosis and the role of JAK2. Caspase 3 is expressed in PC12 cells and is known to be involved in apoptosis. Caspase 3 activity was examined following Aβ(1–42)-induced apoptosis. The fluorescent peptide substrate Ac-DEVD-7AMC was used to measure caspase 3-like activity in cell lysates. As shown in FIG. 5, the caspase 3 activity that resulted in the cleavage of the peptide substrate Ac-DEVD-7AMC is evident after 4 hours of Aβ(1–42) treatment and increased over time until it reached a peak after 8 hours of treatment. The Aβ(1–42)-induced activation of caspase 3 is blocked by nicotine (P<0.01), and this inhibition is prevented by AG-490 (FIG. 5).

Figure 7:
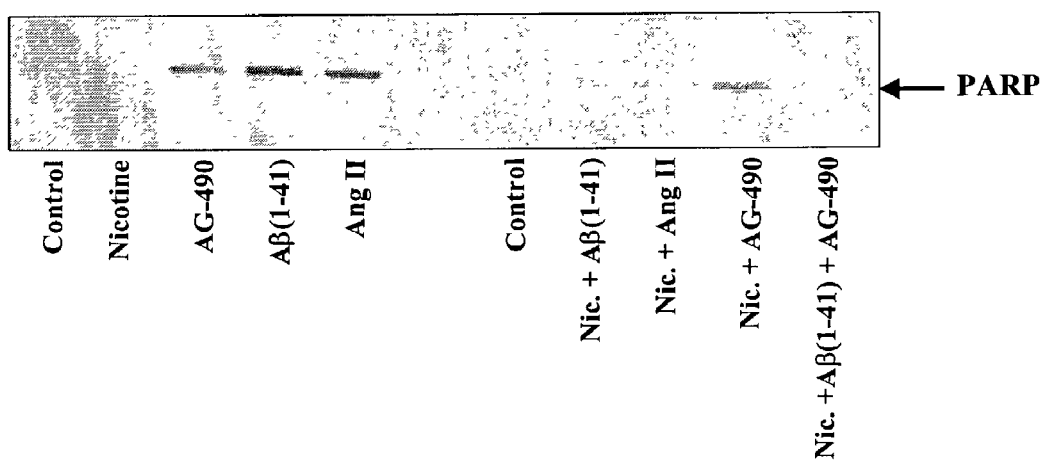
FIG. 7 shows Western blot analysis illustrating the effects of the JAK2 inhibitor (AG-490) on nicotine protection against Aβ- and Ang II-induced apoptosis in PC12 cells. PARP is marker of cells undergoing apoptosis. PARP expression was determined by Western analysis of PC12 cells lysate treated for 8 hours by Aβ(1–42) peptide at 100 nM or Ang II at 100 nM in the presence or absence of nicotine and/or AG-490.

The activation of caspase 3 following Aβ(1–42) treatment was further explored by measuring the cleavage of the DNA-repairing enzyme poly-(ADP-ribose)polymerase (PARP) using Western blot assay. PARP is an endogenous substrate for caspase 3 which is cleaved to a typical 85-kDa fragment during various forms of apoptosis. As shown in FIG. 7, PARP (116-kDa) was cleaved to its 85-kDa fragment following Aβ(1–42) treatment. This PARP cleavage further indicates that caspase 3 or caspase 3-like proteases are activated in Aβ(1–42)-induced cell death.

Figure 4:
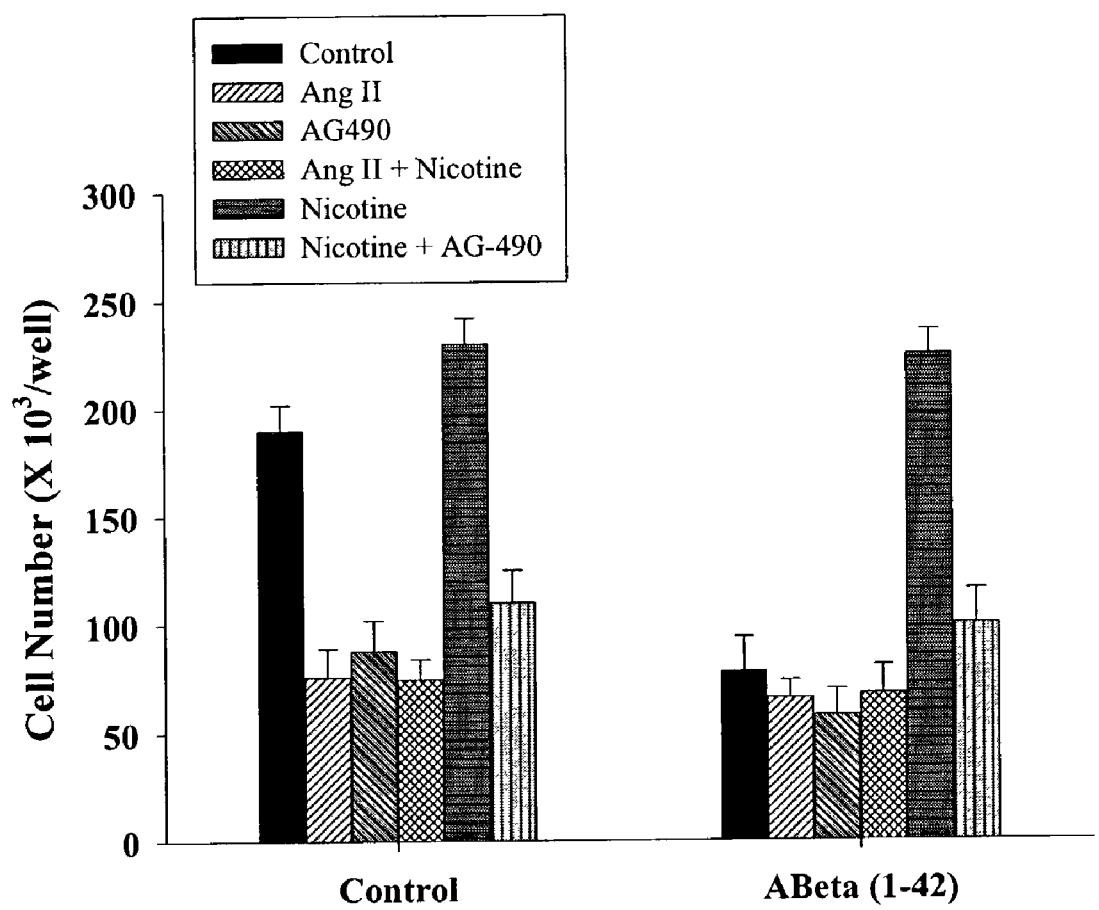
FIG. 4 is a graphic representation of the effects of the JAK2 inhibitor AG-490 on nicotine protection against Aβ- and Ang II-induced cell death in PC12 cells. PC12 cells were treated for 8 hours with either Aβ(1–42) peptide at 100 nM or Ang II at 100 nM in the presence or absence of nicotine and/or AG-490. PC12 cells cultures were processed as described in the Examples, and cell number was counted at the end of respective incubations. Results represent the mean±SEM of four independent cultures. Aβ induced a significant decrease in cell number (*P<0.01) which was significantly inhibited by co-incubation with nicotine (**P<0.01). Nicotine, on the other hand, had no effect in the presence of AG-490. Ang II also significantly reduced PC12 cell number (+P<0.01), a result not significantly affected by nicotine (#P>0.05).

The involvement of JAK2 in nicotine-induced neuroprotection in the presence or absence of Aβ(1–42) was tested. The decrease in PC12 cell number was measured using a COULTER counter (Model ZM, Coulter, Hialeah, Fla.) following Aβ(1–42) and Ang II treatments in the presence or absence of nicotine and AG-490. As shown in FIG. 4, cell death induced by Aβ(1–42) treatment is significantly reduced in the presence of nicotine (P<0.01). Nicotine had no effect on Aβ(1–42)-induced cell death when co-incubated with AG-490 (FIG. 4). These results demonstrate that JAK2 plays a role in the nicotine-induced neuroprotection against Aβ(1–42)-induced cell death. In contrast, Ang II-induced apoptosis was not affected by nicotine (FIG. 4).

α7-nAChR/JAK2 Neuroprotective Cascade. Direct linkages between α7-nAChR and the tyrosine-phosphorylated enzyme JAK2 result in subsequent activation of PI-3-K, Akt, and induction of Bcl-2. This complex formation and downstream neuroprotective cascade is prevented when Aβ(1–42) interacts with α7-nAChR. This is evidenced by the stimulation of pro-apoptotic events including induction of caspase 3, PARP induction, and decreased cell viability. Whereas nicotine interaction with α7-nAChR is "dominant" over Aβ(1–42) toxicity through JAK2 activation, nicotine neuroprotective effect can be neutralized through activation of AT2 receptor as evidenced by the reversal of JAK2 phosphorylation and inhibition of nicotine-induced neuroprotection.

Nicotinic neurotransmission is compromised in the brains of AD patients and selective loss of nAChR predominates in brain regions with β-amyloid deposition (Court, J., et al. *Biol. Psychiatry* 49: 175–184 (2001)). Accumulating evidence suggests that neuronal nicotinic receptor (NNR)-selective ligands can also offer neuroprotective effects in a number of cellular and animal models including neuronal death resulting from β-amyloid toxicity. A direct interaction of the β-amyloid peptide with the α7-nAChR is suggested by recent findings. β-amyloid peptide interacts with high affinity to the α7-nAChR and results in functional non-competitive blockade α7-nAChR in hippocampal neurons (Wang, H. Y., et al. *J. Biol. Chem.* 275: 5626–5632 (2000); Liu, Q., et al. *Proc Natl Acad Sci USA* 98(8):4734–9 (2001)). Neuroprotective mechanisms mediated by nicotine in clonal cells have implicated tyrosine phosphorylation of PI-3P kinase, an enzyme involved in phosphoinositide metabolism and linked to cell survival and apoptosis. Anti-apoptotic signals transduced via JAK2 have been reported from several studies. In hematopoietic cells, the kinase domain of JAK2 mediates the induction of Bcl-2 and inhibits cell death (Sakai, I. and A. S. Kraft, *J. Biol. Chem.* 272:12350–12358 (1997)). Treatment with the JAK2 inhibitor AG-490 reduced the phosphorylation of PI-3-K (Kumano, K., et al., *Biochem. Biophys. Res. Commun.* 270:209–214 (2000)), and that of STAT3 resulting in an increase in caspase-3 activity and Bax protein in acute myocardial infarction (Negoro, S., et al., *Cardiovasc. Res.* 47:797–805 (2000)). Activation of neuronal EPO receptors (EPORs) prevents apoptosis induced by NMDA (N-methyl-D-aspartate) or NO by triggering crosstalk between the signaling pathways of JAK2 and nuclear factor-kappaB (NF-kappaB) (Digicaylioglu, M. and S. A. Lipton. *Nature* 412:641–647 (2001)).

The present inventors have shown that α7-nAChR activation induces JAK2 phosphorylation and this initial event is followed by PI-3 kinase phosphorylation and Akt phosphorylation, as indicated by the inhibitory effect of AG-490 on the phosphorylation of both proteins. The JAK2 phosphorylation in the presence of nicotine is completely inhibited by α-bungarotoxin, an antagonist to α7-nAChR. Nicotine-stimulated α7-nAChR results in the formation of a complex between the α7 receptor protein and the tyrosine phosphorylated JAK2.

Because interaction between α7-nAChR and Aβ(1–42) has been reported based on ligand-binding and functional studies, the possibility that α-amyloid could also induce an a7-nAChR/JAK2 complex was tested. The association of β-amyloid and α7-nAChR was confirmed but no detectable levels of tyrosine-phosphorylated JAK2 were indicated in response to binding. In the presence of nicotine, no Aβ immunoreactivity was be detected in cell lysates, indicating that nicotine has "displaced" Aβ from α7-nAChR. This effect is independent of JAK2 phosphorylation, as shown by the lack of any reversal of this effect in the presence of AG-490.

The mechanism by which nicotine inhibits Aβ toxicity is unclear. The present inventions demonstrates a central role for tyrosine phosphorylation of JAK2 in α7-nAChR activation of key cellular enzymes involved in cell survival and in inhibition of pro-apoptotic pathways. Nicotine inhibits β-amyloid cytotoxicity and this effect is completely prevented by inhibition of tyrosine phosphorylation of JAK2. These effects can be shown by measuring markers of cytotoxicity (e.g., PARP), induction of pro-apoptotic enzymes (e.g., caspase 3), cell number, or induction of Bcl2.

AT2 receptors are expressed in PC12 and have been shown to inhibit the JAK/STAT signaling cascade (Kunioku, H., et al., *Neurosci. Lett.* 309: 13–16 (2001). In contrast to nicotine-induced neuroprotection against Aβ(1–42), pretreatment of cells with Ang II blocks the nicotine-induced activation of JAK2 via the AT2 receptor and completely prevents α7-nAChR-mediated neuroprotective effects further suggesting a pivotal role for JAK2 phosphorylation. The present invention demonstrates opposite roles on cell viability between α7-nAChR and AT2 receptor activity (activation of the latter overriding the potential benefit through the former). These results and the convergence of these pathways on phosphorylated JAK2 indicate that recruitment of α7-nAChR-mediated neuroprotection against Aβ(1–42) may be optimized under conditions where AT2-mediated inhibition of JAK2 phosphorylation is minimized. These findings identify novel molecular mechanisms that are fully consistent with the role attributed to AT2 and β-amyloid on the pathophysiology observed in the brain of Alzheimer's Disease patients.

High-throughput Screening (HTS). The screening methods of the invention may be readily adapted to facilitate high-throughput analysis. Assessment of the tyrosine phosphorylation state provides information regarding candidate substances that either stimulate or inhibit nicotine receptors such as the α7 receptor, or that either stimulate or inhibit the AT2 receptor.

The substance (compounds) can be present in combinatorial or other compound libraries, for example, lead generation and/or lead optimization libraries. For purposes of this invention, lead generation libraries are relatively large libraries that contain potential lead compounds, and lead optimization libraries are developed around compounds identified as potential leads by assaying lead generation libraries. Such libraries typically include a large number of compounds, include at least two compounds, and can include upwards of tens of thousands of compounds.

Logically arranged collections of potentially active compounds can be evaluated using the high throughput bioassays described herein, such that structure-reactivity relationships (SARs) can be obtained. Methods for arranging compounds to be assayed in logical arrangements are known to those of skill in the art, and described, for example, in U.S. Pat. No. 5,962,736 to Zambias et al., the contents of which are hereby incorporated by reference. In one embodiment, the compounds are added to multi-well plates in the form of an "array," which is defined herein as a logical positional ordering of compounds in Cartesian coordinates, where the array includes compounds with a similar core structure and varying substitutions. Additional guidance regarding HTS assays methods can be found in U.S. Pat. No. 6,468,736 to Brooker; and in U.S. Appln. Publication No. 2002/0039749A1 in the name of Wu.

By placing the compounds in a logical array in multi-tube arrays or multi-well plates, the effect of individual compounds can be evaluated, and compared to that of structurally similar compounds to generate SAR data.

In one embodiment, the identity and activity of the compounds are stored on a relational database. By evaluating the SAR data, lead compounds can be identified, and lead optimization libraries designed. The logically arranged arrays can be evaluated in a manner which automatically generates complete relational structural information such that a positive result provides: (1) information on a compound within any given spatial address on the multi-well plates and (2) the ability to extract relational structural information from negative results in the presence of positive results.

Any chemical compound can be used as a test substance (compound) in the assays of the invention. The assays can be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial library containing a large number of test compounds. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487–493 (1991) and Houghton et al., Nature 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al, J. Amer. Chem. Soc. 114:6568 (1992)), nonpeptidal peptidomimetics with $\beta$-D-glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Ausubel, Berger and Sambrook, all supra), peptide nucleic acid libraries (see, e.g. U.S. Pat. No. 5,539,083), antibody libraries (see, e.g., Vaughn et al., Nature Biotechnology, 14(3):309–314 (1996) and PCT/US96/10287), carbohydrate libraries (see, e.g. Liang et al., Science, 274: 1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

As noted, the invention provides in vitro assays for test substances that affect nicotine receptor activity as detected by JAK2 tyrosine phosphorylation in a high throughput format. Control reactions that measure the level of JAK2 phosphorylation in a reaction that does not include any test substance are optional, as the assays are highly uniform. Such optional control reactions are appropriate and increase the reliability of the assay. Accordingly, in one embodiment, the methods of the invention include such a control reaction. For each of the assay formats described, control reactions which do not include a test substance can provide a background level of JAK2 phosphorylation.

In some assays it will be desirable to use positive controls to ensure that the components of the assays are working properly. At least two types of positive controls are appropriate. First, a known stimulator of nAChR which increases JAK2 phosphorylation can be incubated with one sample of the assay, and the resulting increase in signal can be determined according to the methods herein. Second, a known inhibitor of the nAChR can be added, and the resulting decrease in activity similarly detected. It will be appreciated that test substances can also be combined with stimulatory substances or inhibitors to find test substances which inhibit activation or repression that is otherwise caused by the presence of the known stimulatory substance or inhibitor. Because the level of JAK2 phosphorylation resulting from stimulation of the nAChR is shown herein to be decreased by substances that stimulate the AT2 receptor, it will be understood that a coordinate protocol for testing substances mediating an effect through the AT2 receptor can be arranged for testing substances for effects mediated through AT2 or, indirectly, through effects on substances that are themselves modulators of AT2 activity (e.g., the effects of ACE inhibitors, preventing the formation of Ang II).

In the high throughput assays of the invention, it is possible to screen up to several thousand different test substances in a single day. In particular, each well of a microtiter plate can be used to run a separate assay against a selected test substance, or, if concentration or incubation time effects are to be observed, every 5–10 wells can test a single test substance. Thus, a single standard microtiter plate can assay about 100 (96) substances. If 1536 well plates are used, then a single plate can easily assay from about 100-about 1500 different compounds. It is possible to assay many different plates per day; assay screens for up to about 6,000–20,000, and even up to about 100,000–1,000,000 different compounds is possible using the integrated systems of the invention.

Animal Model Testing. Regarding compositions and methods of the invention directed toward treatment and/or prophylaxis of neurodegerative disorders, animal models based on the effects induced by 1-methyl-4-phenyl-1,2,3,6-tetrahydropyridine (MPTP) are relevant (Behmand, R. A. and S. I. Harik. Nicotine enhances 1-methyl-4-phenyl-1,2,3,6-tetrahydropyridine neurotoxicity. *J. Neurochem.*, 58:776–9 (1992); Ferger, B., et al., Effects of nicotine on hydroxyl free radical formation in vitro and on MPTP-induced neurotoxicity in vivo. *Naunyn Schmiedebergs Arch Pharmacol*, 358: 351–9 (1998); Fung, Y. K., et al., Chronic administration of nicotine fails to alter the MPTP-induced neurotoxicity in mice. *Gen Pharmacol* 22(4):669–72 (1991); Maggio, R., et al., Nicotine prevents experimental parkinsonism in rodents and induces striatal increase of neurotrophic factors. *J Neurochem*, 71:2439–46(1998); and Parain, K, et al., Nicotine, but not cotinine, partially protects dopaminergic neurons against MPTP-induced degeneration in mice. *Brain Res.* 890:347–350(2001), all incorporated fully herein by reference).

Models based on MPTP-induced effects include chronic hemi-Parkinsonian monkeys (Domino, E. F., et al., Nicotine alone and in combination with L-DOPA methyl ester or the D(2) agonist N-0923 in MPTP-induced chronic hemiparkinsonian monkeys. *Exp Neurol*, 158:414–21(1999), incorporated fully herein by reference), degeneration of nigrostriatal dopamine neurons in mice (Janson, A. M., et al., Differential effects of acute and chronic nicotine treatment on MPTP- (1-methyl-4-phenyl-1,2,3,6-tetrahydropyridine) induced degeneration of nigrostriatal dopamine neurons in the black mouse. *Clin Investig,* 70:232–8 (1992), incorporated fully herein by reference), evaluations of cognitive function in MPTP-treated animals (Schneider, J. S., et al., Nicotinic acetylcholine receptor agonist SIB-1508Y improves cognitive functioning in chronic low-dose MPTP-treated monkeys. *J Pharmacol Exp Ther,* 290:731–9 (1999), incorporated fully herein by reference), and measurement of striatal levels of 1-methyl-4-phenylpyridinium (MPP+) (Quik, M. and D. A. Di Monte, Nicotine administration reduces striatal MPP+ levels in mice. *Brain Res,* 917:219–24 (2001), incorporated fully herein by reference).

Other relevant animal models include kainic acid-induced effects (Borlongan, C. V., et al., (−)-nicotine protects against systemic kainic acid-induced excitotoxic effects. *Exp Neurol,* 136:261–5(1995), incorporated fully herein by reference), 6-hydroxydopamine (6-OHDA) lesion in rat (Costa, G., et al., Nicotine prevents striatal dopamine loss produced by 6-hydroxydopamine lesion in the substantia nigra. *Brain Res,* 888:336–342(2001); Ryan, R. E., et al., Dose-related neuroprotective effects of chronic nicotine in 6-hydroxydopamine treated rats, and loss of neuroprotection in α4 nicotinic receptor subunit knockout mice. *Br J. Pharmacol.* 132:1650–6(2001); and Soto-Otero, R. et al., Effects of (−)-nicotine and (−)-cotinine on 6-hydroxydopamine-induced oxidative stress and neurotoxicity: relevance for Parkinson's disease. *Biochem Pharmacol,* 64(1):125–35(2002), all incorporated fully herein by reference); quinolinic acid-induced hippocampal neurodegeneration (O'Neill, A. B., et al., Histological and behavioral protection by (−)-nicotine against quinolinic acid-induced neurodegeneration in the hippocampus. *Neurobiol Learn Mem,* 69:46–64 (1998), incorporated fully herein by reference); murine models of neonatal excitotoxic brain injury (Laudenbach, V., et al., Selective activation of central subtypes of nicotinic acetylcholine receptor has opposite effects on neonatal excitotoxic brain injuries. *FASEB J* 16:423–425(2002), incorporated fully herein by reference); and reserpine-induced striatal dopamine deficiency (Oishi, R., et al., Possible explanations for the antagonism by nicotine against reserpine-induced depletion of monoamines in mouse brain. *Naunyn Schmiedebergs Arch Pharmacol.* 348:154–7(1993)).

Effects on the age-associated loss of nigrostriatal dopaminergic neurons may also be evaluated to determine the potential for preventing or alleviating neurodegenerative disease (See, e.g., Prasad, C., et al., Chronic nicotine intake decelerates aging of nigrostriatal dopaminergic neurons. *Life Sci,* 54:1169–84 (1994); and see, generally, Picciotto, M. R. and M. Zoli, Nicotinic receptors in aging and dementia. *J Neurobiol.* 53:641–55(2002), all incorporated fully herein by reference).

Compositions. The methods of prophylaxis and/or treatment, as well as the pharmaceutical compositions, can include substances that stimulate nicotine receptors and substances that inhibit an AT2 receptor, either directly or indirectly.

Substances that stimulate nicotine receptors, either directly or indirectly, include α7 agonists, cholinergic ligands, nicotinic agonists, and/or acetylcholinesterase inhibitors. Nicotine receptor agonists of the invention can include those discussed in, e.g., U.S. Pat. No. 5,977,144; U.S. Pat. No. 6,218,383; U.S. Pat. No. 6,310,102; U.S. Pat. No. 6,232,316; Miller, et al., published international patent application No. WO0190109A1; Bencherif, et al., published international patent application No. WO0182978A2; Dull et al., published international patent application No. WO0071520A2; Bencherif, published international patent application No. WO007600A1; and Caldwell, et al., published international patent application No. WO9965876A1 (all fully incorporated herein by reference). Substances that can be used according to the methods of the present invention include those compounds as represented by the following formulae I–III:

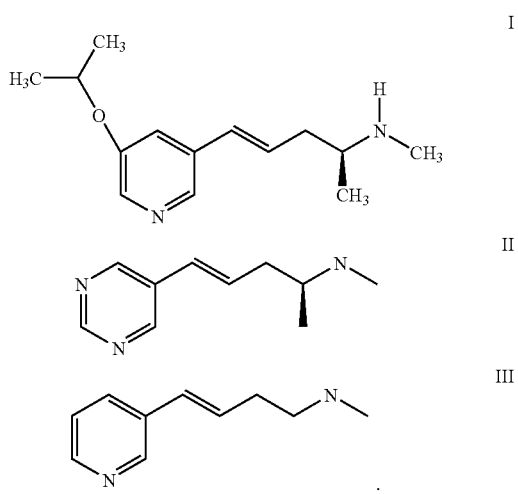

Substances that can be used also include compounds disclosed in U.S. Pat. Nos. 5,952,339; 5,986,100; 6,057,446; and 6,211,372 (all fully incorporated herein by reference). Substances that selectively stimulate particular receptors, e.g., α7-nAChR, can be used. Schmitt and Bencherif provide guidance regarding the selection of compounds that selectively interact with particular receptors, including the α7 subtype. (See Schmitt, J. and M. Bencherif, Chapter 5, "Nicotinic Acetylcholine Receptors," in *Ann. Rep. Med. Chem.* 35:41–51 (2000); and Schmitt, J., *Curr. Med. Chem.,* 7(8):749–800 (2000), both fully incorporated herein by reference).

Various compounds have been reported to interact with alpha 7 nicotinic receptors and have been proposed as therapies on that basis. See, for instance, PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens, et al., *Psychopharm.* 136:320 (1998), Dolle, et al., *J. Labelled Comp. Radiopharm.* 44: 785–795 (2001) and Macor, et al., *Bioorg. Med. Chem. Lett.* 11:319–321 (2001) and references therein. Among these compounds, a common structural theme is that of the substituted tertiary bicyclic amine (e.g., quinuclidine). Similar substituted quinuclidine compounds have also been reported to bind at muscarinic receptors. See, for instance, U.S. Pat. No. 5,712,270 to Sabb and PCTs WO 02/00652 and WO 02/051841.

Compounds of useful according to the present invention include azaadamantane compounds, e.g., as taught in U.S. Pat. Nos. 5,986,100 and 5,952,339, having the general formula I:

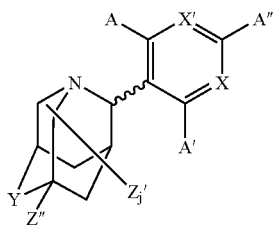

wherein each of X and X' are individually nitrogen or carbon bonded to a substituent species characterized as having a sigma m value greater than 0, often greater than 0.1, and generally greater than 0.2, and even greater than 0.3; less than 0, generally less than −0.1; or 0 (i.e., is hydrogen); as determined in accordance with Hansch, et al., Chem. Rev. 91:165 (1991); Z' is a substituent other than hydrogen (e.g., alkyl, aryl, aralkyl, halo, hydroxyl, alkoxyl, alkylhydroxy, cyano and mercapto); j is an integer from 0 to 5, preferably 0 or 1, and most preferably 0; and the wavy line in the structure indicates that certain compounds can exist in the form of enantiomers or diasteromers depending upon the placement of substituent groups on the 1-aza-tricyclo [3.3.1.1$^{3,7}$]decane portion of the compound. The identity of A, A' and A" can vary, and individually represent those species described as substituent species to the aromatic carbon atom previously described for X and X'; and each of those substituent species often has a sigma m value between about −0.3 and about 0.75, frequently between about −0.25 and about 0.6. More specifically, individual examples of the substituent species to X and X' (when X and X' are hcarbon atoms), Z', A, A' and A" include F, Cl, Br, I, R', NR'R", CF$_3$, OH, CN, NO$_2$, C$_2$R', SH, SCH$_3$, N$_3$, SO$_2$, CH$_3$, OR', SR', C(=O)NR'R", NR'C(=O)R', C(=O)R', C(=O)OR', (CH$_2$)$_q$OR', OC(=O)R', OC(=O)NR'R", and NR'C(=O) OR', where R' and R" are individually hydrogen or lower alkyl (e.g., C$_1$–C$_{10}$ alkyl, preferably C$_1$–C$_6$ alkyl, and more preferably cyclohexyl, methyl, ethyl, isopropyl or isobutyl), an aromatic group-containing species, and q is an integer from 1 to 6. In certain circumstances, it is preferred that when X' is carbon, the sigma m value of the substituent bonded to that carbon is not equal to 0. However, for certain compounds, the sigma m value of A" is equal to 0; that is, A" is H. For certain preferred compounds, X' is carbon bonded to a non-hydrogen substituent (i.e., such compounds are 5-substituted-3-pyridyl compounds). In addition, it is highly preferred that A is hydrogen, it is preferred that A' is hydrogen, and normally A" is hydrogen. Generally, A and A' both are hydrogen; sometimes A and A' are hydrogen, and A" is halo, OR', OH, NR'R", SH or SR'; and often A, A' and A" are all hydrogen. R' and R" can be straight chain or branched alkyl, or R' and R" can form a cycloalkyl functionality (e.g., cyclopropyl, cyclobutyl, cyclopentyl, cyclohexyl, cycloheptyl, adamantyl, quinuclidinyl). Representative aromatic group-containing species include pyridinyl, quinolinyl, pyrimidinyl, phenyl benzyl (where any of the foregoing can be suitably substituted with at least one substituent group, such as alkyl, halo, or amino substituents). Representative aromatic ring systems are set forth in Gibson, et al., J. Med. Chem. 39:4065 (1996). For NR'R", the nitrogen and R' and R" can form a ring structure, such as aziridinyl, azetidinyl, pyrrolidinyl, piperidinyl, piperazinyl or morpholinyl. Z" includes hydrogen or Z' (where Z' is as previously defined), preferably hydrogen. Preferably, Z' is attached to either of the carbon atoms alpha to Y. Y includes C=O, C(OH)R', or C—A (where A is as previously defined), but preferably Y is CH$_2$. The compounds represented in general formula I are optically active; and can be provided and used in the form of racemates and enantiomers.

In a particular embodiment, X' is nitrogen characterized as having a sigma m value greater than 0, less than 0 or 0; X is nitrogen or carbon bonded to a substituent species characterized as having a sigma m value equal to 0; A, A' and A" are individually substituent species characterized as having a sigma m value greater than 0, less than 0 or 0; Z' is a substituent other than hydrogen; j is an integer from 0 to 5; and the wavy line in the structure indicates that the compound can exist in the form of an enantiomer or a diasteromer; Z" is hydrogen or a substituent other than hydrogen; Y is C=O, C(OH)R' or C—A, where R' is hydrogen or lower alkyl.

A representative compound is 5-aza-1-(hydroxymethyl)-6-(3-pyridyl)tricyclo[3.3.1.1$^{3,7}$]-decan-2-one, where A, A' and A" each are hydrogen, X is CH, X' is nitrogen, Y is C=O, Z" is CH$_2$OH and j is 0. Another representative compound is 5-aza-6-(3-pyridyl)tricyclo[3.3.1.1$^{3,7}$]decan-2-one, where A, A' and A" each are hydrogen, X is CH, X' is nitrogen, j is 0, Z" is H and Y is C=O. Another representative compound is 5-aza-6-(3-pyridyl)tricyclo[3.3.1.1$^{3,7}$] decan-2-ol, where A, A' and A" each are hydrogen, X is CH, X' is nitrogen, Y is CH$_2$OH, j is 0 and Z" is H. These compounds are particularly useful as intermediates for the preparation of other compounds of the present invention.

A representative compound of the present invention is 1-aza-2-(3-pyridyl)tricyclo[3.3.1.1$^{3,7}$]decane, where A, A' and A" each are hydrogen, X is CH, X' is nitrogen, Y is CH$_2$, j is 0, Z" is H and X is CH. Another representative compound of the present invention is 1-aza-2-(5-bromo(3-pyridyl)) tricyclo[3.3.1.1$^{3,7}$]decane, where A, A' and A" each are hydrogen, X is CBr, X' is nitrogen, Y is CH$_2$, j is 0 and Z" is H. Another representative compound of the present invention is 1-aza-2-(5-amino-(3-pyridyl))tricyclo[3.3.1.1$^{3,7}$]decane, where A, A' and A" each are hydrogen, X is CNH$_2$, X' is nitrogen, Y is CH$_2$, j is 0 and Z" is H. Another reprsentative compound of the present invention is 1-aza-2-(5-ethoxy-(3-pyridyl))tricyclo[3.3.1.1$^{3,7}$]decane, where A, A' and A" each are hydrogen, Y is CH$_2$, j is 0, Z" is H, X is COCH$_2$, CH$_3$, and X' is nitrogen. Another representative compound of the present invention is 1-aza-2-(5-isopropoxy-(3-pyridyl))tricyclo[3.3.1.1$^{3,7}$]decane, where A, A' and A" each are hydrogen, Y is CH$_2$, j is 0, Z" is H, X is COC$_3$H$_7$, and X' is nitrogen. Another representative compound of the present invention is 5-aza-6-(5-bromo-(3-pyridyl))tricyclo[3.3.1.1$^{3,7}$]decan-2-ol, where A, A' and A" each are hydrogen, X is CBr, X' is nitrogen, Y is CH$_2$OH, j is 0 and Z" is H.

Particular embodiments according to the foregoing general formula include:

1-aza-2-(5-bromo(3-pyridyl))tricyclo[3.3.1.1$^{3,7}$]decane;

1-aza-2-(5-amino-(3-pyridyl))tricyclo[3.3.1.1$^{3,7}$]decane;

1-aza-2-(5-ethoxy-(3-pyridyl))tricyclo[3.3.1.1$^{3,7}$]decane;

1-aza-2-(5-isopropoxy-(3-pyridyl))tricyclo[3.3.1.1$^{3,7}$]decane;

2-(3-pyridyl)-1-azatricyclo[3.3.1.1$^{3,7}$]decane;

5-aza-6-(3-pyridyl)tricyclo[3.3.1.1$^{3,7}$]decan-2-ol; and 5-aza-1-(hydroxymethyl)-6-(3-pyridyl)tricyclo[3.3.1.1$^{3,7}$]-decan-2-one;

1-aza-2-(3-pyridyl)-1-azatricyclo[3.3.1.1$^{3,7}$]decane;

5-aza-6-(3-pyridyl)tricyclo[3.3.1.1$^{3,7}$]decan-2-ol;

5-aza-1-(hydroxymethyl)-6-(3-pyridyl)tricyclo[3.3.1.1$^{3,7}$]-decan-2-one;
5-aza-6-(3-pyridyl)tricyclo[3.3.1.1$^{3,7}$]decan-2-one; and
enantiomers and pharmaceutically acceptable salts thereof.

Compounds of useful according to the present invention also include diazabicyclic compounds, e.g., as taught in published international patent application WO 01/90109, having the following general formula:

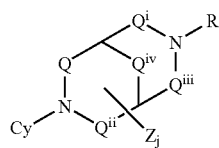

In the structure, Q is $(CH_2)_u$, $Q^i$ is $(CH_2)_v$, $Q^{ii}$ is $(CH_2)_w$, $Q^{iii}$ is $(CH_2)_x$, and $Q^{iv}$ is $(CH_2)_y$, where u, v, w and x are individually 0, 1, 2, 3 or 4, preferably 0 or 1, and y is 1 or 2. R is hydrogen or lower alkyl, preferably hydrogen. In addition, the values of u, v, w, x and y are selected such that the resulting diazabicyclic ring contains 7, 8 or 9 members, preferably 7 members. Z represents a suitable non-hydrogen substituent species; exemplary species are set forth hereinafter. In addition, j is an integer from 0 to 10, preferably 0, 1 or 2.

In the structure, preferably Cy represents a suitably substituted 6-membered aromatic ring, as represented by the formula:

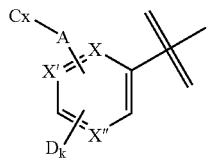

where each of X, X' and X" are individually nitrogen, nitrogen bonded to oxygen (e.g., an N-oxide or other N—O functionality) or carbon bonded to a substituent species (i.e., hydrogen or a non-hydrogen species); A is O (oxygen) or C=O; D is a suitable non-hydrogen substituent species, as set forth hereinafter; k is either 0, 1 or 2, preferably 0 or 1; and Cx is selected from a group consisting of aryl, substituted aryl, heteroaryl, substituted heteroaryl, non-aromatic heterocyclyl, substituted non-aromatic heterocyclyl, non-aromatic heterocyclylalkyl and substituted non-aromatic heterocyclylalkyl. A can also be a covalent bond, with the proviso that when A is so defined, the diazabicyclic ring is not 2,5-diazabicyclo[2.2.1]heptane and/or Cx is not phenyl or substituted phenyl. When A is a covalent bond, it is preferred that Cx is aryl or heteroaryl.

Non-hydrogen substituent species Z and D, as well as those substituent species attached to the various Cx groups, typically have a sigma m value between about −0.3 and about 0.75 and include alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —CF$_3$, —CN, —N$_3$, —NO$_2$, —C$_2$R', —SR', —SOR', —SO$_2$CH$_3$, —SO$_2$NR'R", —C(=O)NR'R", —NR'C(=O)R", —NR'SO$_2$R", —C(=O)R', —C(=O)OR', —(CH$_2$)$_q$OR', —OC(=O)R', —(CR'R")$_q$OCH$_2$C$_2$R', —(CR'R")$_q$C(=O)R', —O(CR'R")$_q$C(=O)R', —C$_2$(CR'R")$_q$OR', —(CR'R")$_q$NR'R", —OC(=O)NR'R" and —NR'C(=O)OR' where R' and R" are individually hydrogen or lower alkyl (e.g., straight chain or branched alkyl including $C_1$–$C_8$, preferably $C_1$–$C_5$, such as methyl, ethyl, or isopropyl), an aromatic group-containing species or a substituted aromatic group-containing species, and q is an integer from 1 to 6. R' and R" can form a cycloalkyl functionality. Representative aromatic groups include carbocyclic (phenyl, biphenyl, naphthyl, etc.) and heterocyclic (pyridinyl, pyrimidinyl, quinolinyl, indolyl, etc.) rings.

As used herein in reference to the diazabicyclic compounds useful according to the invention, "alkyl" refers to straight chain or branched alkyl radicals including $C_1$–$C_8$, preferably $C_1$–$C_5$, such as methyl, ethyl, or isopropyl, and cyclic alkyl radicals up to 8 carbons; "substituted alkyl" refers to alkyl radicals further bearing one or more substituent species such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent species as defined above; "aryl" refers to aromatic radicals having six to ten carbon atoms; "substituted aryl" refers to aryl radicals further bearing one or more substituent species as defined above; "alkylaryl" refers to alkyl-substituted aryl radicals; "substituted alkylaryl" refers to alkylaryl radicals further bearing one or more substituent species as defined above; "arylalkyl" refers to aryl-substituted alkyl radicals; "substituted arylalkyl" refers to arylalkyl radicals further bearing one or more substituent species as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent species as defined above.

As used herein in reference to the diazabicyclic compounds useful according to the invention, the term "heteroaryl" refers to heterocyclic aromatic radicals, such as pyridinyl, pyrimidinyl, pyrazinyl, pyridazinyl, quinolinyl, furanyl, thienyl, pyrrolyl, indolyl, benzoxazolyl, etc.; "non-aromatic heterocyclyl" refers to heterocyclic radicals, saturated or unsaturated, which are not aromatic, such as tetrahydrofuranyl, tetrahydropyranyl, tetrahydrothienyl, tetrahydrothiopyranyl, pyrrolidinyl, piperidinyl, etc.; "non-aromatic heterocyclylalkyl" refers to non-aromatic heterocyclyl radicals attached through an alkylene chain of up to four carbon atoms; in each case, "substituted" refers to the replacement of one or more of the hydrogens in the group with a non-hydrogen substituent species, as described above.

The preferred embodiments of the invention are those in which one or two of X, X' and X" are nitrogen, the most preferred being the case in which only X" is nitrogen. When only X" is nitrogen, it is preferred that A is attached at the C-5 position of the pyridine ring and that k is 0 or 1.

Cx is preferably:

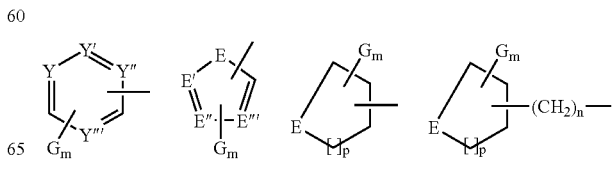

wherein Y, Y', Y" and Y'" are individually nitrogen, nitrogen bonded to oxygen, or carbon bonded to hydrogen or a substituent species, G; E is oxygen, sulfur or nitrogen bonded to hydrogen or a substituent species, G; E', E" and E'" are individually nitrogen or carbon bonded to hydrogen or a substituent species, G; m is 0, 1, 2, 3 or 4; p is 0, 1, 2 or 3; n is 0, 1, 2, 3 or 4; and G is selected from the group consisting of alkyl, substituted alkyl, alkenyl, substituted alkenyl, non-aromatic heterocyclyl, substituted non-aromatic heterocyclyl, aryl, substituted aryl, heteroaryl, substituted heteroaryl, alkylaryl, substituted alkylaryl, arylalkyl, substituted arylalkyl, —F, —Cl, —Br, —I, —OR', —NR'R", —CF$_3$, —CN, —N$_3$, —NO$_2$, —C$_2$R', —SR', —SOR', —SO$_2$CH$_3$, —SO$_2$NR'R", —C(=O)NR'R", —NR'C(=O)R", —NR'SO$_2$R", —C(=O)R', —C(=O)OR', —(CH$_2$)$_q$OR', —OC(=O)R', —(CR'R")$_q$OCH$_2$C$_2$R', —(CR'R")$_q$C(=O)R', —O(CR'R")$_q$C=O)R', —C$_2$(CR'R")$_q$OR', —(CR'R")$_q$NR'R", —OC(=O)NR'R" and —NR'C(=O)OR' where R' and R" are individually hydrogen, lower alkyl, an aromatic group-containing species or a substituted aromatic group-containing species, and q is an integer from 1 to 6. Preferably Y, Y', Y", Y'", E', E" and E'" are all carbon bonded to a substituent species. Alternatively one or two of Y, Y', Y", Y'", E', E"and E'" are nitrogen and the remaining are carbon bonded to a substituent species. R' and R" can form a cycloalkyl functionality. Representative aromatic groups include carbocyclic (phenyl, biphenyl, naphthyl, etc.) and heterocyclic (pyridinyl, pyrimidinyl, quinolinyl, indolyl, etc.) rings. Adjacent non-hydrogen substituent species, G, may combine to form one or more saturated or unsaturated, substituted or unsubstituted, carbocyclic or heterocyclic rings containing, but not limited to, ether, acetal, ketal, amine, ketone, lactone, lactam, carbamate and urea functionalities.

Representative diazabicyclic compounds useful according to the present invention include the following:

(1S,4S)-2-(5-phenoxy-3-pyridyl)-2,5-diazabicyclo[2.2.1]heptane;
(1R,4R)-2-(5-phenoxy-3-pyridyl)-2,5-diazabicyclo[2.2.1]heptane;
(1S,4S)-2-(5-(3-methoxyphenoxy)-3-pyridyl)-2,5-diazabicyclo[2.2.1]heptane;
(1R,4R)-2-(5-(3-methoxyphenoxy)-3-pyridyl)-2,5-diazabicyclo[2.2.1]heptane;
(1S,4S)-2-(5-(4-methoxyphenoxy)-3-pyridyl)-2,5-diazabicyclo[2.2.1]heptane;
(1R,4R)-2-(5-(4-methoxyphenoxy)-3-pyridyl)-2,5-diazabicyclo[2.2.1]heptane;
(1S,4S)-2-(5-(3,4-dimethoxyphenoxy)-3-pyridyl)-2,5-diazabicyclo[2.2.1]heptane;
(1R,4R)-2-(5-(3,4-dimethoxyphenoxy)-3-pyridyl)-2,5-diazabicyclo[2.2.1]heptane;
(1S,4S)-2-(5-(4-fluorophenoxy)-3-pyridyl)-2,5-diazabicyclo[2.2.1]heptane;
(1R,4R)-2-(5-(4-fluorophenoxy)-3-pyridyl)-2,5-diazabicyclo[2.2.1]heptane;
(1S,4S)-2-(5-benzoyl-3-pyridyl)-2,5-diazabicyclo[2.2.1]heptane;
(1R,4R)-2-(5-benzoyl-3-pyridyl)-2,5-diazabicyclo[2.2.1]heptane;
(1S,4S)-2-(5-(4-(N-phenylpiperidinyl)oxy)-3-pyridyl)-2,5-diazabicyclo[2.2.1]heptane;
(1R,4R)-2-(5-(4-(N-phenylpiperidinyl)oxy)-3-pyridyl)-2,5-diazabicyclo[2.2.1]heptane;
(1S,4S)-2-(5-(4-(N-trifluoroacetylpiperidinyl)oxy)-3-pyridyl)-2,5-diazabicyclo[2.2.1]heptane;
(1R,4R)-2-(5-(4-(N-trifluoroacetylpiperidinyl)oxy)-3-pyridyl)-2,5-diazabicyclo[2.2.1]heptane;
6-methyl-3-(5-phenyl-3-pyridyl)-3,6-diazabicyclo[3.2.1]octane;
6-methyl-3-(5-phenoxy-3-pyridyl)-3,6-diazabicyclo[3.2.1]octane;
6-methyl-3-(5-(3-methoxyphenoxy)-3-pyridyl)-3,6-diazabicyclo[3.2.1]octane;
6-methyl-3-(5-(4-methoxyphenoxy)-3-pyridyl)-3,6-diazabicyclo[3.2.1]octane;
6-methyl-3-(5-(3,4-dimethoxyphenoxy)-3-pyridyl)-3,6-diazabicyclo[3.2.1]octane;
6-methyl-3-(5-(4-fluorophenoxy)-3-pyridyl)-3,6-diazabicyclo[3.2.1]octane;
6-methyl-3-(5-benzoyl-3-pyridyl)-3,6-diazabicyclo[3.2.1]octane;
6-methyl-3-(5-(4-(N-phenylpiperidinyl)oxy)-3-pyridyl)-3,6-diazabicyclo[3.2.1]octane;
3-methyl-6-(5-phenyl-3-pyridyl)-3,6-diazabicyclo[3.2.1]octane;
3-methyl-6-(5-phenoxy-3-pyridyl)-3,6-diazabicyclo[3.2.1]octane;
3-methyl-6-(5-(3-methoxyphenoxy)-3-pyridyl)-3,6-diazabicyclo[3.2.1]octane;
3-methyl-6-(5-(4-methoxyphenoxy)-3-pyridyl)-3,6-diazabicyclo[3.2.1]octane;
3-methyl-6-(5-(3,4-dimethoxyphenoxy)-3-pyridyl)-3,6-diazabicyclo[3.2.1]octane;
3-methyl-6-(5-(4-fluorophenoxy)-3-pyridyl)-3,6-diazabicyclo[3.2.1]octane;
3-methyl-6-(5-benzoyl-3-pyridyl)-3,6-diazabicyclo[3.2.1]octane;
3-methyl-6-(5-(4-(N-phenylpiperidinyl)oxy)-3-pyridyl)-3,6-diazabicyclo[3.2.1]octane;
6-(5-phenyl-3-pyridyl)-3,6-diazabicyclo[3.2.2]nonane;
6-(5-phenoxy-3-pyridyl)-3,6-diazabicyclo[3.2.2]nonane;
6-(5-(3-methoxyphenoxy)-3-pyridyl)-3,6-diazabicyclo[3.2.2]nonane;
6-(5-(4-methoxyphenoxy)-3-pyridyl)-3,6-diazabicyclo[3.2.2]nonane;
6-(5-(3,4-dimethoxyphenoxy)-3-pyridyl)-3,6-diazabicyclo[3.2.2]nonane;
6-(5-(4-fluorophenoxy)-3-pyridyl)-3,6-diazabicyclo[3.2.2]nonane;
6-(5-benzoyl-3-pyridyl)-3,6-diazabicyclo[3.2.2]nonane;
6-(5-(4-(N-phenylpiperidinyl)oxy)-3-pyridyl)-3,6-diazabicyclo[3.2.2]nonane;
3-(5-phenyl-3-pyridyl)-3,6-diazabicyclo[3.2.2]nonane;
3-(5-phenoxy-3-pyridyl)-3,6-diazabicyclo[3.2.2]nonane;
3-(5-(3-methoxyphenoxy)-3-pyridyl)-3,6-diazabicyclo[3.2.2]nonane;
3-(5-(4-methoxyphenoxy)-3-pyridyl)-3,6-diazabicyclo[3.2.2]nonane;
3-(5-(3,4-dimethoxyphenoxy)-3-pyridyl)-3,6-diazabicyclo[3.2.2]nonane;
3-(5-(4-fluorophenoxy)-3-pyridyl)-3,6-diazabicyclo[3.2.2]nonane;
3-(5-benzoyl-3-pyridyl)-3,6-diazabicyclo[3.2.2]nonane;
3-(5-(4-(N-phenylpiperidinyl)oxy)-3-pyridyl)-3,6-diazabicyclo[3.2.2]nonane;
3-(5-phenyl-3-pyridyl)-3,7-diazabicyclo[3.1.1]nonane;
3-(5-phenoxy-3-pyridyl)-3,7-diazabicyclo[3.1.1]nonane;
3-(5-(3-methoxyphenoxy)-3-pyridyl)-3,7-diazabicyclo[3.3.1]nonane;
3-(5-(4-methoxyphenoxy)-3-pyridyl)-3,7-diazabicyclo[3.1.1]nonane;

3-(5-(3,4-dimethoxyphenoxy)-3-pyridyl)-3,7-diazabicyclo[3.1.1]nonane;
3-(5-(4-fluorophenoxy)-3-pyridyl)-3,7-diazabicyclo[3.1.1]nonane;
3-(5-benzoyl-3-pyridyl)-3,7-diazabicyclo[3.1.1]nonane; and
3-(5-(4-(N-phenylpiperidinyl)oxy)-3-pyridyl)-3,7-diazabicyclo[3.1.1]nonane,
or an enantiomer, or a pharmaceutically acceptable salt thereof.

Compounds useful according to the present invention also include cinnamamides of 3-aminoquinuclidine, e.g., as taught in published international patent application WO 01/36417, of the general formula:

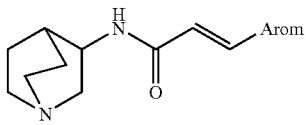

wherein Arom represents a 5- or 6-membered aromatic or heteroaromatic ring containing zero to three nitrogen atoms, zero to one oxygen atoms, and zero to one sulfur atoms, or an 8-, 9- or 10-membered fused aromatic or heteroaromatic ring system containing zero to four nitrogen atoms, zero to one oxygen atom, and zero to one sulfur atoms, which may be optionally substituted with one or more substituents selected from the following: hydrogen, halogen, $C_1$–$C_4$ alkyl, $C_2$–$C_4$ alkenyl, $C_2$–$C_4$ alkynyl, aryl, heteroaryl, —$CO_2R^1$, —CN, —$NO_2$, —$NR^2R^3$, —$CF_3$ or —$OR^4$;
$R^2$, $R^3$, and $R^4$ are independently hydrogen, $C_1$–$C_4$ alkyl, aryl, heteroaryl, —C(O)$R^5$, —C(O)NH$R^6$, —C(O)$R^7$ or —$SO_2R^8$, or $R^2$ and $R^3$ may together be $(CH_2)_jQ(CH_2)_k$ where Q is O, S, $NR^9$, or a bond;
j is 2 to 4;
k is 0 to 2; and
$R^1$, $R^4$, $R^5$, $R^6$, $R^7$, $R^8$ and $R^9$, are independently $C_1$–$C_4$ alkyl, aryl, or heteroaryl.

The compounds according to the foregoing general formula can include:
N-(1-Azabicyclo[2.2.2]oct-3-yl)(E-3-phenylpropenamide);
N-(1-Azabicyclo[2.2.2]oct-3-yl)(3-phenylpropenamide);
N-(1-Azabicyclo[2.2.2]oct-3-yl)[E-3-(2-nitrophenyl)propenamide];
N-(1-Azabicyclo[2.2.2]oct-3-yl)[E-3-(2-nitropheflyl)propenamide];
N-(1-Azabicyclo[2.2.2]oct-3-yl)[E-3-(2-aminophenyl)propenamide];
N-(1-Azabicyclo[2.2.2]oct-3-yl)[Z-3-(2-methoxyphenyl)propenamide];
N-(1-Azabicyclo[2.2.2]oct-3-yl)-N-methyl-(E-3-phenylpropenamide);
N-(1-Azabicyclo[2.2.2]oct-3-yl)[E-2-phenylcyclopropane-1-carboxamide];
N-(1-Azabicyclo[2.2.2]oct-3-yl)(Z-2-fluoro-3-phenylpropenamide);
N-(1-Azabicyclo[2.2.2]oct-3-yl)[E-3-(2-formamidophenyl)propenamide];
N-(1-Azabicyclo[2.2.2]oct-3-yl)[E-3-(4-nitrophenyl)propenamide];
N-(1-Azabicyclo[2.2.2]oct-3-yl)(E-3-(4-aminophenyl)propenamide;
N-(1-Azabicyclo[2.2.2]oct-3-yl)[E-3-(4-formamidophenyl)propenamide];
N-(1-Azabicyclo[2.2.2]oct-3-yl)(Z-3-methyl-3-phenylpropenamide);
N-(1-Azabicyclo[2.2.2]oct-3-yl)[E-3-(4-N-methylanilinophenyl)propenamide];
N-(1-Azabicyclo[2.2.2]oct-3-yl)[E-3-(4-N,N-dimethylaminophenyl)propenamide];
N-(1-Azabicyclo[2.2.2]oct-3-yl)(Z-3-phenylpropenamide);
N-(1-Azabicyclo[2.2.2]oct-3-yl)(E-methyl-3-phenylpropenamide);
N-(1-Azabicyclo[2.2.2]oct-3-yl)(E-2,3-diphenylpropenamide);
N-(1-Azabicyclo[2.2.2]oct-3-yl)[E-3-(4-methoxyphenyl)propenamide];
N-(1-Azabicyclo[2.2.2]oct-3-yl)(E methyl-3-phenylpropenamide);
N-(1-Azabicyclo[2.2.2]oct-3-yl)[E-3-(2-methylphenyl)propenamide];
N-(1-Azabicyclo[2.2.2]oct-3-yl)[E-3-(3-methoxyphenyl)propenamide];
N-(1-Azabicyclo[2.2.2]oct-3-yl)[E-3-(2-fluorophenyl)propenamide];
N-(1-Azabicyclo[2.2.2]oct-3-yl)[E-3-(4-fluorophenyl)propenamide];
N-(1-Azabicyclo[2.2.2]oct-3-yl)[E-(2-chlorophenyl)propenamide];
N-(1-Azabicyclo[2.2.2]oct-3-yl)[E-3-(3-chlorophenyl)propenamide];
N-(1-Azabicyclo[2.2.2]oct-3-yl)[E-3-(4-chlorophenyl)propenamide];
N-(1-Azabicyclo[2.2.2]oct-3-yl)[E-3-(3,4-dichlorophenyl)propenamide];
N-(1-Azabicyclo[2.2.2]oct-3-yl)-[E-3-(3-bromophenyl)propenamide];
N-(1-Azabicyclo[2.2.2]oct-3-yl)-[E-3-(4-bromophenyl)propenamide];
N-(1-Azabicyclo[2.2.2]oct-3-yl)[E-3-(3-iodophenyl)propenamide];
N-(1-Azabicyclo[2.2.2]oct-3-yl)[E-3-(4-iodophenyl)propenamide];
N-(1-Azabicyclo[2.2.2]oct-3-yl)[E-3-(2-trifluoromethylphenyl)propenamide];
N-(1-Azabicyclo[2.2.2]oct-3-yl)-[E-3-(3-trifluoromethylphenyl)propenamide];
N-(1-Azabicyclo[2.2.2]oct-3-yl)[E-3-(2-furyl)propenamide];
N-(1-Azabicyclo[2.2.2]oct-3-yl)[E-3-(3-furyl)propenamide];
N-(1-Azabicyclo[2.2.2]oct-3-yl)[E-3-(2-pyridyl)propenamide];
N-(1-Azabicyclo[2.2.2]oct-3-yl)[E-3-(3-pyridyl)propenamide];
N-(1-Azabicyclo[2.2.2]oct-3-yl)[E-3-(4-pyridyl)propenamide];
N-(1-Azabicyclo[2.2.2]oct-3-yl)[E-3-(2-thienyl)propenamide];
N-(1-Azabicyclo[2.2.2]oct-3-yl)[E-3-(3-thienyl)propenamide];
N-(1-Azabicyclo[2.2.2]oct-3-yl)[E-3-(5-nitro-2-furyl)propenamide];
N-(1-Azabicyclo[2.2.2]oct-3-yl)[E-3-(5-methoxy-3-pyridyl)propenamide];
N-(1-Azabicyclo[2.2.2]oct-3-yl)[E-3-(5-hydroxy-3-pyridyl)propenamide];
N-(1-Azabicyclo[2.2.2]oct-3-yl)[E-3-(4-imidazolyl)propenamide];
N-(endo-8-Aza-8-methylbicyclo[3.2.1]oct yl)(E-3-phenyipropenamide);

N-(exo-8-Aza-8-methylbicyclo[3.2.1]octyl)(E-3-phenylpropenamide;

or an enantiomer thereof, or a pharmaceutically acceptable salt thereof.

Compounds useful according to the present invention also include arylcarbamates of 3-quinuclidinol, e.g., as taught in published international patent application WO 97/30998, of the general formula:

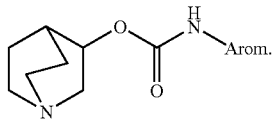

Particular embodiments of the foregoing general formula include:
N-phenylcarbamic acid 1-azabicyclo[2.2.2]octan-3-yl ester;
N-(4-bromophenyl)carbamic acid 1-azabicyclo[2.2.2]octan-3-yl ester;
N-(4-methylphenyl)carbamic acid 1-azabicyclo[2.2.2]octan-3-yl ester;
N-(4-methoxyphenyl)carbamic acid 1-azabicyclo[2.2.2]octan-3-yl ester;
N-(3,4-dichlorophenyl)carbamic acid 1-azabicyclo[2.2.2]octan-3-yl ester;
N-(4-cyanophenyl)carbamic acid 1-azabicyclo[2.2.2]octan-3-yl ester;
N-phenylcarbamic acid 1-azabicyclo[2.2.1]heptan-3-yl ester;
N-(3-methoxyphenyl)carbamic acid 1-azabicyclo[2.2.2]octan-3-yl ester;
N-phenylthiocarbamic acid 1-azabicyclo[2.2.2]octan-3-yl ester;
N-(2-pyridyl)carbamic acid 1-azabicyclo[2.2.2]octan-3-yl ester;
N-(1-naphthyl)carbamic acid 1-azabicyclo[2.2.2]octan-3-yl ester;
N-phenylcarbamic acid (3R)-1-azabicyclo[2.2.2]octan-3-yl ester;
N-phenylcarbamic acid (3S)-1-azabicyclo[2.2.2]octan-3-yl ester;
N-(4-pyridyl)carbamic acid 1-azabicyclo[2.2.2]octan-3-yl ester;
N-(m-biphenyl)carbamic acid 1-azabicyclo[2.2.2]octan-3-yl ester;
N-(3-quinolinyl)carbamic acid 1-azabicyclo[2.2.2]octan-3-yl ester;
or an enantiomer thereof, or a pharmaceutically acceptable salt thereof.

Compounds useful according to the present invention also include heteroaromatic amides of 3-aminoquinuclidine, e.g., as taught in published international patent application WO 02/15662, of the general formula:

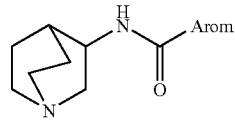

where Arom is a cyclic heteroaromatic moiety where the heteroatoms can be from 1–3 atoms selected from oxygen, sulfur, or nitrogen of the following structures:

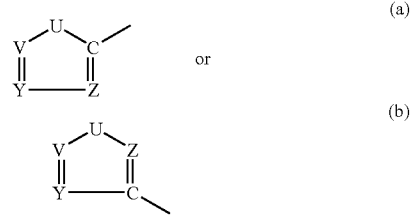

wherein U is —O—, —S—, or —N(R$_1$)—;
V and Y are independently selected from =N—, or =C(R$_2$)—;
Z is =N—, or =CH—, provided that when both V and Y are =C(R$_2$)— and Z is =CH—, only one =C(R$_2$)— can be =CH—, and further provided that when U is —O—, Y is =C(R$_2$)— and Z is =C(R$_2$)—, V cannot be =N—;
R$_1$ is —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, or aryl, and provided that when W is (b) and Z is =N— and U is N(R$_1$), R$_1$ cannot be phenyl or substituted phenyl;

Alkenyl is straight and branched-chain moieties having from 2–6 carbon atoms and having at least one carbon-carbon double bond;

Halogenated alkenyl is an unsaturated alkenyl moiety having from 2–6 carbon atoms and having 1 to (2n−1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —R$_3$, —R$_5$, —OR$_6$, —SR$_6$, —NR$_6$R$_6$, —C(O)R$_6$, —C(O)NR$_6$R$_6$, —CN, —NR$_6$C(O)R$_6$, —S(O)$_2$NR$_6$R$_6$, —NR$_6$S(O)$_2$R$_6$, phenyl, or substituted phenyl;

Alkynyl is straight and branched-chain moieties having from 2–6 carbon atoms and having at least one carbon-carbon triple bond;

Halogenated alkynyl is an unsaturated alkynyl moiety having from 3–6 carbon atoms and having 1 to (2n−3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —R$_3$, —R$_5$, —OR$_6$, —SR$_6$, —NR$_6$R$_6$, —C(O)R$_6$, —CN, —C(O)NR$_6$R$_6$—NR$_6$C(O)R$_6$, —S(O)$_2$NR$_6$R$_6$, —NR$_6$S(O)$_2$R$_6$, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —OR$_6$, —SR$_6$, —NR$_6$R$_6$, —C(O)R$_6$, —C(O)NR$_6$R$_6$, —CN, —NR$_6$C(O)R$_6$—S(O)$_2$NR$_6$R$_6$, —NR$_6$S(O)$_2$R$_6$, —NO$_2$, phenyl, or substituted phenyl;

Heterocycloalkyl is a cyclic moiety having 4–7 atoms with 1–2 atoms within the ring being —S—, —N(R$_1$)—, or —O—;

Halogenated heterocycloalkyl is a cyclic moiety having from 4–7 atoms with 1–2 atoms within the ring being —S—, —N(R$_1$)—, or —O—, and having 1–4 substituents independently selected from —F, or —Cl;

Substituted heterocycloalkyl is a cyclic moiety having from 4–7 atoms with 1–2 atoms within the ring being —S—, —N(R$_1$)—, or —O— and having 0–3 substituents independently selected from —F, or —Cl, and further having 1 substituent selected from —OR$_6$, —SR$_6$, —NR$_6$R$_6$, —C(O)R$_6$, —C(O)NR$_6$R$_6$, —CN, —NR$_6$C(O)R$_6$, —NO$_2$, —S(O)$_2$NR$_6$R$_6$, —NR$_6$S(O)$_2$R$_6$, phenyl, or substituted phenyl;

R$_2$ is independently selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —OR$_4$, —SR$_4$, —F, —Cl, —Br, —I, —NR$_4$R$_4$, —C(O)R$_4$, —C(O)NR$_4$R$_4$, —CN, —NR$_4$C(O)R$_7$, —S(O)$_2$NR$_4$R$_4$, —OS(O)$_2$R$_7$, —S(O)$_2$R$_4$, NR$_4$S(O)$_2$R$_4$, —N(H)C(O)N(H)R$_4$, —NO$_2$, —R$_3$, and —R$_5$;

R$_3$ is 5-membered heteroaromatic mono-cyclic moieties containing within the ring 1–3 heteroatoms independently selected from the group consisting of —O—, =N—, —N(R$_1$)—, and —S—, and having 0–1 substituent selected from —R$_8$ and 0–3 substituents independently selected from —F, —Cl, —Br, or —I, or R$_3$ is a 9-membered fused-ring moiety having a 6-membered ring fused to a 5-membered ring and having the formula

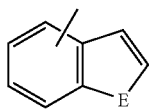

wherein E is O, S, or NR$_1$,

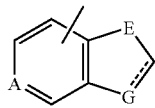

wherein E and G are independently selected from CR$_{10}$, O, S, or NR$_1$, and A is CR$_{10}$ or N, or

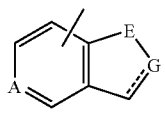

wherein E and G are independently selected from CR$_{10}$, O, S, or NR$_1$, and A is CR$_{10}$ or N, each 9-membered fused-ring moiety having 0–1 substituent selected from —R$_8$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each R$_4$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, —R$_3$, —R$_5$, phenyl, or substituted phenyl;

R$_5$ is 6-membered heteroaromatic mono-cyclic moieties containing within the ring 1–3 heteroatoms selected from =N— and having 0–1 substituent selected from —R$_8$ and 0–3 substituent(s) independently selected from —F, —Cl, —Br, or —I, or 10-membered heteroaromatic bi-cyclic moieties containing within one or both rings 1–3 heteroatoms selected from =N—, including quinolinyl or isoquinolinyl, each 10-membered fused-ring moiety having 0–1 substituent selected from —R$_8$ and 0–3 substituent(s) independently selected from —F, —Cl, —Br, or —I and having a bond directly or indirectly attached to the core molecule where valency allows;

Each R$_6$ is independently selected from —H, alkyl, cycloalkyl, heterocycloalkyl, alkyl substituted with 1 substituent selected from R$_9$, cycloalkyl substituted with 1 substituent selected from R$_9$, heterocycloalkyl substituted with 1 substituent selected from R$_9$ halogenatedalkyl, halogenated cycloalkyl, halogenated heterocycloalkyl, phenyl, substituted phenyl, —R$_3$, or —R$_5$;

Each R$_7$ is independently selected from —H, alkyl, cycloalkyl, heterocycloalkyl, halogenated alkyl, halogenated cycloalkyl, or halogenated heterocycloalkyl;

R$_8$ is selected from —OR$_7$, —SR$_7$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —NR$_7$R$_7$, —C(O)R$_7$, —NO$_2$, —C(O)NR$_7$R$_7$, —CN, —NR$_7$C(O)R$_7$, —S(O)$_2$NR$_7$R$_7$, or —NR$_7$S(O)$_2$R$_7$;

R$_9$ is selected from —OR$_7$, —SR$_7$, —NR$_7$R$_7$, —C(O)R$_7$, —C(O)NR$_7$R$_7$, —CN—NR$_7$C(O)R$_7$, —S(O)$_2$NR$_7$R$_7$, —NR$_7$S(O)$_2$R$_7$, —CF$_3$, or —NO$_2$;

Each R$_{10}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_7$, —SR$_7$, —NR$_7$R$_7$, —C(O)R$_7$, —NO$_2$, —C(O)NR$_7$R$_7$, —CN, —NR$_7$C(O)R$_7$, —S(O)$_2$NR$_7$R$_7$, or NR$_7$S(O)$_2$R$_7$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_7$, —SR$_7$, —NR$_7$R$_7$, —C(O)R$_7$, —NO$_2$, —C(O)NR$_7$R$_7$, —CN, —NR$_7$C(O)R$_7$, —S(O)$_2$NR$_7$R$_7$, or —NR$_7$S(O)$_2$R$_7$, and further provided that the fused-ring moiety has 0–3 substituent(s) selected from —F, —Cl, —Br, or —I.

Limited substituted alkyl is a substituted alkyl having from 1–6 carbon atoms and having 0–3 substituents independently selected from —F, —Cl, —Br, or —I, and further having 1 substituent on either only the ω carbon and selected from OR$_7$, —SR$_7$, —NR$_7$R$_7$, —C(O)R$_7$, —NO$_2$, —C(O)NR$_7$R$_7$, —CN, —NR$_6$C(O)R$_7$, —S(O)$_2$NR$_6$R$_6$, or —NR$_6$S(O)$_2$R$_6$, or on any carbon with sufficient valency but not on the ω carbon and selected from —R$^3$, —R$_5$, —OR$_6$, —SR$_6$, —NR$_6$R$_6$, —C(O)R$_6$, —NO$_2$, —C(O)NR$_6$R$_6$, —CN, —NR$_6$C(O)R$_6$, —S(O)$_2$NR$_6$R$_6$, —NR$_6$S(O)$_2$R$_6$, phenyl, or substituted phenyl;

Limited substituted alkenyl is a substituted alkenyl having from 1–6 carbon atoms and having 0–3 substituents independently selected from —F, —Cl, —Br, or —I, and further having 1 substituent on either only the ω carbon and selected from —OR₇, —SR₇, —NR₇R₇, —C(O)R₇, —NO₂, —C(O)NR₇R₇, —CN, —NR₆C(O)R₇, —S(O)₂NR₆R₆, or —NR₆S(O)₂R₆, or on any carbon with sufficient valency but not on the ω carbon and selected from —R₃, —R₅, —OR₆, —SR₆, —NR₆R₆, —C(O)R₆, —NO₂, —C(O)NR₆R₆, —CN, —NR₆C(O)R₆, —S(O)₂NR₆R₆, —NR₆S(O)₂R₆, phenyl, or substituted phenyl; and Limited substituted alkynyl is a substituted alkynyl having from 1–6 carbon atoms and having 0–3 substituents independently selected from —F, —Cl, —Br, or —I, and further having 1 substituent on either only the ω carbon and selected from —OR₇, —SR₇, —NR₇R₇, —C(O)R₇, —NO₂, —C(O)NR₇R₇, —CN, —NR₆C(O)R₇, —S(O)₂NR₆R₆, or —NR₆S(O)₂R₆, or on any carbon with sufficient valency but not on the ω carbon and selected from —R₃, —R₅, —OR₆, —SR₆, —NR₆R₆, —C(O)R₆, —NO₂, —C(O)NR₆R₆, —CN, —NR₆C(O)R₆, —S(O)₂NR₆R₆, —NR₆S(O)₂R₆, phenyl, or substituted phenyl Particular embodiments according to the foregoing general formula include;

N-((3R)-1-azabicyclo[2.2.2]oct-3-yl)-5-phenylthiophene-2-carboxamide; and

N-((3R)-1-azabicyclo[2.2.2]oct-3-yl)-5-phenyl-1,3,4-oxadiazole-2-carboxamide, or a pharmaceutically acceptable salt thereof.

Compounds useful according to the present invention also include heteroaromatic amides of 3-aminoquinuclidine, e.g., as taught in published international patent application WO 02/16356, of the general formula I:

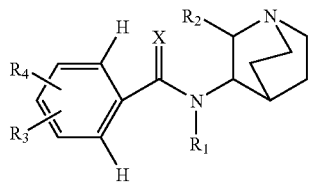

Formula I or pharmaceutically acceptable salts thereof, wherein X is O or S;

R₁ is independently selected from the group consisting of —H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —R₁₂ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —R₁₂ and 0–3 substituents independently selected from —F, —Cl, —Br, or —I, where the substitution can be independently on either only one ring or both rings of said naphthalene moiety;

R₂ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —OR₁₀, —SR₁₀, —NR₁₀R₁₀, —C(O)R₁₀, —C(O)NR₁₀R₁₀, —CN, —NR₁₀C(O)R₁₀, —S(O)₂NR₁₀R₁₀, —NR₁₀S(O)₂R₁₀, —NO₂, —R₇, —R₉, phenyl, or substituted phenyl;

Substituted benzyl is a benzyl either having 1–4 substituents independently selected from —F, —Cl, —Br, or —I, or having 1 substituent selected from —R₁₂ and 0–3 substituents independently selected from —F, —Cl, —Br, or —I, provided that all substitution is on the phenyl ring of the benzyl;

R₃ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —R₇, —R₉, —OR₈, —SR₈, —F, —Cl, —Br, —I, —NR₈R₈, —C(O)R₈, —CN, —C(O)NR₈R₈, —NR₈C(O)R₈, —S(O)R₈, —OS(O)₂R₈, —NR₈S(O)₂R₈, NO₂, and —N(H)C(O)N(H)R₈;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —R₇, —R₉, —OR₁₀, —SR₁₀, —NR₁₀R₁₀, —C(O)R₁₀, —C(O)NR₁₀R₁₀, —NR₁₀C(O)R₁₀, —S(O)₂NR₁₀R₁₀, —NR₁₀S(O)₂R₁₀, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —R₇, —R₉, —OR₁₀, —SR₁₀, —NR₁₀R₁₀, —C(O)R₁₀, —C(O)NR₁₀R₁₀, —NR₁₀C(O)R₁₀, —S(O)₂NR₁₀R₁₀, —NR₁₀S(O)₂R₁₀, —CN, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —OR₁₀, —SR₁₀, —NR₁₀R₁₀, —C(O)R₁₀, —CN, —C(O)NR₁₀R₁₀, —NR₁₀C(O)R₁₀, —S(O)₂NR₁₀R₁₀, —NR₁₀S(O)₂R₁₀, —NO₂, phenyl, or substituted phenyl;

Heterocycloalkyl is a cyclic moiety having 4–7 atoms with 1–2 atoms within the ring being —S—, —N(R$_3$)—, or —O—;

Halogenated heterocycloalkyl is a cyclic moiety having from 4–7 atoms with 1–2 atoms within the ring being —S—, —N(R$_3$)—, or —O—, and having 1–4 substituents independently selected from —F, or —Cl;

Substituted heterocycloalkyl is a cyclic moiety having from 4–7 atoms with 1–2 atoms within the ring being —S—, —N(R$_3$)—, or —O— and having 0–3 substituents independently selected from —F, or —Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —NO$_2$, —S(O)$_2$NR$_{10}$R$_{10}$, —NR$_{10}$S(O)$_2$R$_{10}$, phenyl, or substituent phenyl;

R$_4$ is selected from the group consisting of —O—R$_5$, —S—R$_5$, —S(O)—R$_5$, —C(O)—R$_5$, and alkyl substituted on the ω carbon with R$_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

R$_5$ is selected from aryl, R$_7$, or R$_9$;

R$_7$ is 5-membered heteroaromatic mono-cyclic moieties containing within the ring 1–3 heteroatoms independently selected from the group consisting of —O—, =N—, —N(R$_{14}$)—, and —S—, and having 0–1 substituent selected from —R$_{12}$ and 0–3 substituents independently selected from —F, —Cl, —Br, or —I, or R$_7$ is a 9-membered fused-ring moiety having a 6-membered ring fused to a 5-membered ring and having the formula

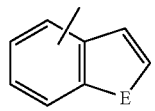

wherein E is O, S, or NR$_{14}$,

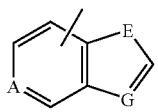

wherein E and G are independently selected from CR$_{18}$, O, S, or NR$_{14}$, and A is CR$_{18}$ or N, or

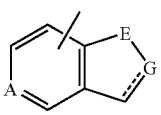

wherein E and G are independently selected from CR$_{18}$, O, S, or NR$_{14}$, and A is CR$_{18}$ or N, each 9-membered fused-ring moiety having 0–1 substituent selected from —R$_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each R$_8$ is independently selected from —H, alkyl, halogenated alkyl, substituted alkyl, cycloalkyl, halogenated cycloalkyl, substituted cycloatkyl, heterocycloalkyl, halogenated heterocycloalkyl, substituted heterocycloalkyl, R$_7$, R$_9$, phenyl, or substituted phenyl;

R$_9$ is 6-membered heteroaromatic mono-cyclic moieties containing within the ring 1–3 heteroatoms selected from =N— and having 0–1 substituent selected from —R$_{12}$ and 0–3 substituent(s) independently selected from —F, —Cl, —Br, or —I, or 10-membered heteroaromatic bi-cyclic moieties containing within one or both rings 1–3 heteroatoms selected from =N—, including quinolinyl or isoquinolinyl, each 10-membered fused-ring moiety having 0–1 substituent selected from —R$_{12}$ and 0–3 substituent(s) independently selected from —F, —Cl, —Br, or —I and having a bond directly or indirectly attached to the core molecule where valency allows;

Each R$_{10}$ is independently selected from —H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently selected from —H, alkyl, cycloalkyl, heterocycloalkyl, halogenated alkyl, halogenated cycloalkyl, or halogenated heterocycloalkyl;

R$_{12}$ is selected from —OR$_{11}$, —SR$_{11}$, alkyl, cycloalkyl, heterocycloalkyl, halogenated alkyl, halogenated cycloalkyl, halogenated heterocycloalkyl, substituted alkyl, substituted cycloallcyl, substituted heterocycloalkyl, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$;

R$_{13}$ is selected from —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

R$_{14}$ is selected from —H, alkyl, halogenated alkyl, substituted atkyl, cycloalkyl, halogenated cycloalkyl, substituted cycloalkyl, heterocycloalkyl, halogenated heterocycloalkyl, substituted heterocycloalkyl, phenyl, or substituted phenyl;

Each R$_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

Each R$_{16}$ is independently selected from cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

R$_{17}$ is selected from cycloalkyl, halogenated cycloalkyl, substituted cycloalkyl, heterocycloalkyl, halogenated heterocycloalkyl, or substituted heterocycloalkyl; and Each R$_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from —F, —Cl, —Br, or —I.

Particular embodiments according to the foregoing general formula include;

N-[(3R)-1-azabicyclo[2.2.2]oct-3-y-l]-4-(4-hydroxyphenoxy)benzamide;
N-[(3R)-1-azabicyclo[2.2.2]oct-3-yl]-4-(-4-acetamidophenoxy)benzamide;
N-[(3R)-1-azabicyclo[2.2.2]oct-3-yl]-4-phenoxybenzamide;
N-[(3R)-1-azabicyclo[2.2.2]oct-3-yl]-4-benzylbenzamide;
N-[(3R)-1-azabicyclo[2.2.2]oct-3-yl]-4-(phenylsulfanyl)benzamide;
N-[(3R)-1-azabicyclo[2.2.2]oct-3-yl]-3-phenoxybenzamide;
N-[(3R)-1-azabicyclo[2.2.2]oct-3-yl]-4-benzoylbenzamide;
N-[(3R)-1-azabicyclo[2.2.2]oct-3-yl]-4-(4-fluorophenoxy)benzamide;
N-[(3R)-1-azabicyclo[2.2.2]oct-3-yl]-4-(2-fluorophenoxy)benzamide;
N-[(3R)-1-azabicyclo[2.2.2]oct-3-yl]-4-(3-fluorophenoxy)benzamide;
N-[(3R)-1-azabicyclo[2.2.2]oct-3-yl]-4-(2-chlorophenoxy)benzamide;
N-[(3R)-1-azabicyclo[2.2.2]oct-3-yl]-4-(3-chlorophenoxy)benzamide;
N-[(3R)-1-azabicyclo[2.2.2]oct-3-yl]-4-(4-chlorophenoxy)benzamide;
N-[(3R)-1-azabicyclo[2.2.2]oct-3-yl]-4-(2-methoxyphenoxy)benzamide;
N-[(3R)-1-azabicyclo[2.2.2]oct-3-yl]-4-(3-methoxyphenoxy)benzamide;
N-[(3R)-1-azabicyclo[2.2.2]oct-3-yl]-4-(4-methoxyphenoxy)benzamide;
N-[(3R)-1-azabicyclo[2.2.2]oct-3-yl]-4-(3-chlorophenylsulfanyl)benzamide;
N-[(3R)-1-azabicyclo[2.2.2]oct-3-yl]-4-(4-methoxyphenoxy)benzamide;
N-[(3R)-1-azabicyclo[2.2.2]oct-3-yl]-4-(3-chlorophenylsulfanyl)benzamide;
N-[(3R)-1-azabicyclo[2.2.2]oct-3-yl]-4-(4-chlorophenylsulfanyl)benzamide;
N-[(3R)-1-azabicyclo[2.2.2]oct-3-yl]-4-(3-methoxyphenylsulfanyl)-benzamide;
N-[(3R)-1-azabicyclo[2.2.2]oct-3-yl]-4(2-methoxyphenylsulfanyl)-benzamide;
N-(2-methyl-1-azabicyclo[2.2.2]oct-3-yl)4-phenoxybenzamide; and pharmaceutically acceptable salts thereof.

Further, N-((3R)-1-azabicyclo[2.2.2]oct-3-yl)-4-(pyridin-3-yloxy)benzarnide and pharmaceutically acceptable salts thereof are also useful.

Compounds useful according to the present invention also include spiroquinuclidine compounds, e.g., as taught in published international patent application WO 99/03859, of the general formula:

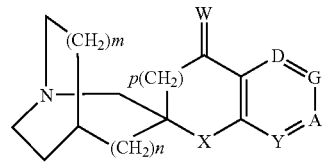

wherein n is 0 or 1; m is 0 or 1; p is 0 or 1; X is oxygen or sulfur; Y is CH, N or NO; W is oxygen, H$_2$ or F$_2$; A is N or C(R$^2$); G is N or C(R$^3$); D is N or C(R$^4$);

with the proviso that no more than one of A, G, and D is nitrogen but at least one of Y, A, G, and D is nitrogen or NO;

R$^1$ is hydrogen or C$_1$–C$_4$ alkyl;

R$^2$, R$^3$, and R$^4$ are independently hydrogen, halogen, C$_1$–C$_4$ alkyl, C$_2$–C$_4$ alkenyl, C$_2$–C$_4$ alkynyl, aryl, heteroaryl, OH, OC$_1$–C$_4$ alkyl, CO$_2$R$^1$, —CN, —NO$_2$, —NR$^5$R$^6$, —CF$_3$, —OSO$_2$CF$_3$, or R$^2$ and R$^3$, or R$^3$ and R$^4$, respectively, may together form another six membered aromatic or heteroaromatic ring sharing A and G, or G and D, respectively, containing between zero and two nitrogen atoms, and substituted with one to two of the following substituents: independently hydrogen, halogen, C$_1$–C$_4$ alkyl, C$_2$–C$_4$ alkenyl, C$_2$–C$_4$ alkynyl, aryl, heteroaryl, OH, OC$_1$–C$_4$ alkyl, CO$_2$R$^1$, —CN, —NO$_2$, —NR$^5$R$^6$, —CF$_3$, —OSO$_2$CF$_3$;

R$^5$ and R$^6$ are independently hydrogen, C$_1$–C$_4$ alkyl, C(O)R$^7$, C(O)NHR$^8$, C(O)OR$^9$, SO$_2$R$^{10}$ or may together be (CH$_2$)$_j$Q(CH$_2$)$_k$ where Q is O, S, NR$^{11}$, or a bond; j is 2 to 7; k is 0 to 2;

R$^7$, R$^8$, R$^9$, R$^{10}$, and R$^{11}$ are independently C$_1$–C$_4$ alkyl, aryl, or heteroaryl, or an enantiomer thereof, or a pharmaceutically acceptable salt thereof.

Particular embodiments according to the foregoing general formula include:

spiro[1-azabicyclo[2.2.2]octane-3,2'-(3'H)-furo[2,3-b]pyridine];
5'-bromospiro[1-azabicyclo[2.2.2]octane-3,2'-(3'H)-furo[2,3-b]pyridine];
5'-phenylspiro[1-azabicyclo[2.2.2]octane-3,2'-(3'H)-furo[2,3-b]pyridine];
5'-nitrospiro[1-azabicyclo[2.2.2]octane-3,2'-(3'H)-furo[2,3-b]pyridine];
1'-chlorospiror[1-azabicyclo[2.2.2]octane-3,2'-(3'H)-furo[2,3-b]isoquinoline];
5'-(phenylcarboxamido)spiro[1-azabicyclo[2.2.2]octane-3,2'-(3'H)-furo[2,3-b]pyridine];
5'-(phenylaminocarbonylamino)spiro[1-azabicyclo[2.2.2]octane-3,2'-(3'H)-furo[2,3-b]pyridine];
5'-(phenylsulfonylamido)spiro[1-azabicyclo[2.2.2]octane-3,2'-(3'H)-furo[2,3-b]pyridine];
5'-aminospiro[1-azabicyclo[2.2.2]octane-3,2'-(3'H)-furo[2,3-b]pyridine];
5'-N-methylaminospiro[1-azabicyclo[2.2.2]octane-3,2'-(3'H)-furo[2,3-b]pyridine];
5'-N,N-dimethylaminospiro[1-azabicyclo[2.2.2]octane-3,2'-(3'H)-furo[2,3-b]pyridine];
5'-N,N-diethylaminospiro[1-azabicyclo[2.2.2]octane-3,2'-(3'H)-furo[2,3-b]pyridine];
5'-N-ethylaminospiro[1-azabicyclo[2.2.2]octane-3,2'-(3'H)-furo[2,3-b]pyridine];
5'-N-benzylaminospiro[1-azabicyclo[2.2.2]octane-3,2'-(3'H)-furo[2,3-b]pyridine]

5'-N-formamidospiro[1-azabicyclo[2.2.2]octane-3,2'-(3'H)-furo[2,3-b]pyridine];
5'-N-acetamidospiro[1-azabicyclo[2.2.2]octane-3,2'-(3'H)-furo[2,3-b]pyridine];
spiro[1-azabicyclo[2.2.2]octane-3,2'-(3'H)-furo[2,3-b]isoquinoline];
spiro[1-azabicyclo[2.2.2]octane-3,2'-(3'H)-furo[2,3-b]quiniline];
5'-ethenylspiro[1-azabicyclo[2.2.2]octane-3,2'-(3'H)-furo[2,3-b]pyridine];
5'-(E)-(phenylethenyl)spiro[1-azabicyclo[2.2.2]octane-3,2'-(3'H)-furo[2,3-b]pyridine];
5'-(4-morpholino)spiro[1-azabicyclo[2.2.2]octane-3,2'-(3'H)-furo[2,3]-bipyridine];
5'-(1-azetidinyl)spiro[1-azabicyclo[2.2.2]octane-3,2'-(3'H)-furo[2,3-b]pyridine];
5'-(E)-(2-(4-pyridyl)ethenyl)spiro[1-azabicyclo[2.2.2]octane-3,2'-(3'H)-furo[2,3-b]pyridine];
5'-(E)-(2-(2-pyridyl)ethenyl)spiro[1-azabicyclo[2.2.2]octane-3,2'-(3'H)-furo[2,3-b]pyridine];
5'-(2-trimethylsilylethynyl(spiro[1-azabicyclo[2.2.2]octane-3,2'-(3'H)-furo[2,3-b]pyridine];
5'-ethynylspiro[1-azabicyclo[2.2.2]octane-3,2'-(3'H)-furo[2,3-b]pyridine];
5'-(2-furyl)spiro[1-azabicyclo[2.2.2]octane-3,2'-(3'H)-furo[2,3-b]pyridine];
5'-(3-pyridyl)spiro[1-azabicyclo[2.2.2]octane-3,2'-(3'H)-furo[2,3-b]pyridine];
5'-methylspiro[1-azabicyclo[2.2.2]octane-3,2'-(3'H)-furo[2,3-b]pyridine];
spiro[1-azabicyclo[2.2.2]octane-3,2'-3'H)-furo[2,3-b]pyridine-5'carbonitrile];
spiro[1-azabicyclo[2.2.2]octane-3,2'-(3'H)-furo[2,3-b]pyridine-5'carboxamide];
5'N'-(3chlorophenyl)ureidoaminospiro[1-azabicyclo[2.2.2]octane-3,2'-(3'H)-furo[2,3-b]pyridine];
5'-N'-(2-nitrophenyl)ureidoaminospiro[1-azabicyclo[2.2.2]octane-3,2'-(3'H)-furo[2,3-b]pyridine];
4'chlorospiro[1-azabicyclo[2.2.2]octane-3,2'-(3'H)-furo[2,3-b]pyridine];
4'-methoxyspiro[1-azabicyclo[2.2.2]octane-3,2'-(3'H)-furo[2,3-b]pyridine];
4'-phenylthiospiro[1-azabicyclo[2.2.2]octane-3,2'-(3'H)-furo[2,3-b]pyridine];
4'-(N-2-aminoethyl)aminospiro[1-azabicyclo[2.2.2]octane-3,2'-(3'H)-furo[2,3-b]pyridine];
4'-Phenylaminospiro[1-azabicyclo[2.2.2]octane-3,2'-(3'H)-furo[2,3-b]pyridine];
4'-methylaminospiro[1-azabicyclo[2.2.2]octane-3,2'-(3'H)-furo[2,3-b]pyridine];
4'-(4-N-methylpiperazin-1-yl)spiro[1-azabicyclo[2.2.2]octane-3,2'-(3'H)-furo[2,3-b]pyridine];
4'-chloro-spiro[1-azabicyclo[2.2.2]octane-3,2'-(3'H)-furo[3,2-c]pyridine];
spiro[1-azabicyclo[2.2.2]octane-3,2'-(3'H)-furo[3,2-c]pyridine];
6'-fluorospiro[1-azabicyclo[2.2.2]octane-3,2'(3'H)-furo[2,3-b]pyridine];
spiro[1-azabicyclo[2.2.2]octane-3,2'(3'H)-furo[2,3-b]pyridine-6'-carbonitrile];
6'-chlorospiro[1-azabicyclo[2.2.2]octane-3,2'(3'H)-furo[2,3-b]pyridine];
or an enantiomer, or pharmaceutically acceptable salt thereof.

Compounds useful according to the present invention also include anabaseine compounds, e.g., as taught in U.S. Pat. No. 5,977,144, of the general formula:

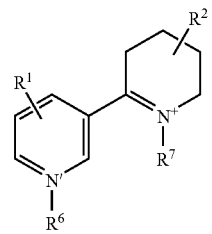

or a salt thereof, wherein $R_1$, $R_6$, and $R_7$ are hydrogen or $C_1$–$C_4$ alkyl; and $R_2$ is =CHCH=CHX, wherein X is

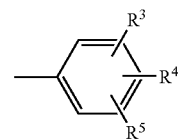

wherein $R^3$, $R^4$, and $R^5$ are selected from the group consisting of hydrogen, $C_1$–$C_4$ alkyl optionally substituted with N,N-diaikylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amino having 1 to 4 carbons in the acyl, cyano, N,N-dialkylamino having 1 to 4 carbons in each of the alkyls, halo, hydroxyl, and nitro.

Particular embodiments of compounds according to the foregoing general formula include benzylidene- or cinnamylidene-anabaseines including:
3-(2,4-dimethoxybenzylidene)anabaseine, 3-(4-hydroxybenzylidene)anabaseine;
3-(4-methoxybenzylidene)anabaseine, 3-(4-aminobenzylidene)anabaseine;
3-(4-hydroxy-2-methoxybenzylidene)anabaseine;
3-(2-hydroxy-4-methoxybenzylidene)anabaseine;
3-(4-isopropoxybenzylidene)anabaseine;
(7'-methyl-3-(2,4-dimethoxybenzylidene))anabaseine;
3-(4-acetylaminocinnamylidene)anabaseine;
3-(4-hydroxycinnamylidene)anabaseine;
3-(4-methoxycinnamylidene)anabaseine;
3-(4-hydroxy-2-methoxycinnamylidene)anabaseine;
3-(2,4-dimethoxycinnamylidene)anabaseine; and
3-(4-acetoxycinnamylidene)anabaseine;
and pharmaceutically acceptable salts thereof.

Substances that inhibit an AT2 receptor, either directly or indirectly, include ACE inhibitors that interfere with the action of AT2 stimulator angiotensin II converting enzyme or ACE (see Brown, N. J. and D. E. Vaughan, *Circulation.* 97:1411–1420 (1998), incorporated fully herein by reference). Such substances also include inhibitors of the AT2 receptor itself. (e.g. PD123177 and PD123319; see Fischer, J. W., et al., *Cardiovasc. Res.* 51(4):784–91 (2001); and Horiuchi, et al. *J. Clin. Invest.* 103(1):63–71(1999), both fully incorporated herein by reference).

ACE inhibitors useful according to the present invention include those taught in Brown, N. J. and D. E. Vaughan, *Circulation,* 97:1411–1420 (1998), e.g., captopril, enalapril, lisinopril, benazepril, quinapril, ramapril, trandolapril, moexipril, fosinopril, and zofenopril. Of course, this list is not intended to be limiting, and other compounds known in the art as ACE inhibitors can also be used.

Polypeptides, Antibodies and Related Methods. The compounds can be, for example, antibodies, antibody fragments, enzymes, proteins, peptides, nucleic acids such as oligonucleotides, or small molecules.

For the protein or polypeptide compounds of the invention, a mimic of one or more amino acids, otherwise known as a polypeptide mimetic or peptidominetic, can also be used. As used herein, the term "mimic" means an amino acid or an amino acid analog that has the same or similar functional characteristic of an amino acid. Thus, for example, a (D)arginine analog can be a mimic of (D)arginine if the analog contains a side chain having a positive charge at physiological pH, as is characteristic of the guinidinium side chain reactive group of arginine. A polypeptide mimetic or peptidomimetic is an organic molecule that retains similar polypeptide chain pharmacophore groups as are present in the corresponding polypeptide. The substitution of amino acids by non-naturally occurring amino acids and peptidomimetics as described above can enhance the overall activity or properties of an individual polypeptide based on the modifications to the side chain functionalities. For example, these types of alterations can be employed along with the oligomer components of the present invention to further enhance the polypeptide's resistance to enzymatic breakdown and/or to improve biological activity.

The antibodies can be, for example, monoclonal, humanized (chimeric) or polyclonal antibodies, and can be prepared using conventional techniques.

Antibodies can be generated that bind to nicotinic receptors, e.g., the α7-nAChR. Antibodies can also be generated that bind to the AT2 receptor. These antibodies can be selected such that they are effective in preventing activation of the receptors when bound to their target. Antibodies can also be produced that bind to substances that stimulate or inhibit receptors, in a manner that interferes with the expected function or activity of the substance. Antibodies can also be prepared that bind and affect the activity of enzyme such as ACE, which generate active ligands that stimulate or inhibit receptor activity. Herein, receptors, ligands, related enzymes, and other effectors used to prepare specific antibodies may be referred to simply as "antigens." The term "ligand" can refer to a specific binding partner of a receptor that is either stimulatory or inhibitory of a particular activity.

Polyclonal antibodies can be used, provided their overall effect is a desired effect (i.e., a stimulatory or inhibitory effect, as desired). Monoclonal antibodies can be used, as well as humanized (chimeric) antibodies. The antibodies may inhibit binding between binding partners such as receptors and their ligands by sterically interfering with and/or binding to all or part of the actual binding site(s), either on the receptor or on the ligand.

The term "antibody" refers to a polypeptide substantially encoded by an immunoglobulin gene or immunoglobulin genes, or fragments thereof, that specifically binds and recognizes an analyte or antigen, e.g. a receptor and/or a ligand (stimulatory or inhibitory substance) relevant to the methods of the invention). Immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit includes a tetramer. Each tetramer is composed of two identical pairs of polypeptide chains, each pair having one "light" (about 25 kD) and one "heavy" chain (about 50–70 kD). The N-terminus of each chain has a variable region of about 100 to 110 or more amino acids primarily responsible for antigen recognition. The terms "variable light chain" (or "VL") and "variable heavy chain" (or "VH") refer to these light and heavy chains, respectively.

Antibodies exist, for example, as intact immunoglobulins or as a number of well-characterized antigen-binding fragments produced by digestion with various peptidases. For example, pepsin digests an antibody below the disulfide linkages in the hinge region to produce an $F(ab')_2$ fragment, a dimer of Fab which itself is a light chain joined to VH-CH1 by a disulfide bond. The $F(ab')_2$ fragment can be reduced under mild conditions to break the disulfide linkage in the hinge region, thereby converting the $F(ab')_2$ dimer into an Fab' monomer. The Fab' monomer is essentially an Fab with part of the hinge region (see *Fundamental Immunology*, Third Edition, W. E. Paul (ed.), Raven Press, N.Y. (1993), the contents of which are hereby incorporated by reference). While various antibody fragments are defined in terms of the digestion of an intact antibody, one of ordinary skill in the art will appreciate that such fragments can be synthesized de novo either chemically or by using recombinant DNA methodology. Thus, the term antibody, as used herein, also includes antibody fragments, such as a single chain antibody, an antigen binding $F(ab')_2$ fragment, an antigen binding Fab' fragment, an antigen binding Fab fragment, an antigen binding Fv fragment, a single heavy chain or a chimeric (humanized) antibody. Such antibodies can be produced by modifying whole antibodies or synthesized de novo using recombinant DNA methodologies.

Receptors, ligands, or other species relevant to the methods of the invention ("antigens"—including fragments, derivatives, and analogs thereof) can be used as immunogens to generate antibodies which immunospecifically bind such immunogens. Such antibodies include, but are not limited to, polyclonal antibodies, monoclonal antibodies, chimeric antibodies, single-chain antibodies, antigen-binding antibody fragments (e.g., Fab, Fab', $F(ab')_2$, Fv, or hypervariable regions), and mAb or Fab expression libraries. In some embodiments, polyclonal and/or monoclonal antibodies to the antigens are produced. In yet other embodiments, fragments of the receptors or ligands that are identified as immunogenic are used as immunogens for antibody production.

Various procedures known in the art can be used to produce polyclonal antibodies. Various host animals (including, but not limited to, rabbits, mice, rats, sheep, goats, camels, and the like) can be immunized by injection with the antigen, fragment, derivative or analog. Various adjuvants can be used to increase the immunological response, depending on the host species. Such adjuvants include, for example, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and other adjuvants, such as BCG (bacille Calmette-Guerin) and *Corynebacterium parvum*.

Any technique that provides for the production of antibody molecules by continuous cell lines in culture can be used to prepare monoclonal antibodies directed toward the receptors or ligands (stimulatory or inhibitory substances) according to the methods of the invention. Such techniques include, for example, the hybridoma technique originally developed by Kohler and Milstein (see, e.g., *Nature* 256: 495–97 (1975)), the trioma technique (see, e.g., Hagiwara and Yuasa, *Hum. Antibodies Hybridomas* 4:15–19 (1993); Hering et al., *Biomed. Biochim. Acta* 47:211–16 (1988)), the human B-cell hybridoma technique (see, e.g., Kozbor et al. *Immunology Today* 4:72 (1983)), and the EBV-hybridoma technique to produce human monoclonal antibodies (see, e.g., Cole et al., In: *Monoclonal Antibodies and Cancer Therapy*, Alan R. Liss, Inc., pp. 77–96 (1985)). Human antibodies can be used and can be obtained by using human hybridomas (see, e.g., Cote et al., *Proc. Natl. Acad. Sci. USA* 80:2026–30 (1983)) or by transforming human B cells with EBV virus in vitro (see, e.g., Cole et al., supra).

"Chimeric" or "humanized" antibodies (see, e.g., Morrison et al., *Proc. Natl. Acad. Sci. USA* 81:6851–55 (1984); Neuberger et al., *Nature* 312:604–08 (1984); Takeda et al., *Nature* 314:452–54 (1985)) can also be prepared. Methods for producing such "chimeric" molecules are generally well known and described in, for example, U.S. Pat. Nos. 4,816,567; 4,816,397; 5,693,762; and 5,712,120; PCT Patent Publications WO 87/02671 and WO 90/00616; and European Patent Publication EP 239 400 (the disclosures of which are incorporated by reference herein). Alternatively, a human monoclonal antibody or portions thereof can be identified by first screening a cDNA library for nucleic acid molecules that encode antibodies that specifically bind to the receptors or ligands of the invention according to the method generally set forth by Huse et al., *Science* 246:1275–81 (1989), the contents of which are hereby incorporated by reference. The nucleic acid molecule can then be cloned and amplified to obtain sequences that encode the antibody (or antigen-binding domain) of the desired specificity. Phage display technology offers another technique for selecting antibodies that bind to the receptors, ligands, or enzymes relevant to the methods of the invention, fragments, derivatives or analogs thereof. (See, e.g., International Patent Publications WO 91/17271 and WO 92/01047; Huse et al., supra.)

Techniques for producing single chain antibodies (see, e.g., U.S. Pat. Nos. 4,946,778 and 5,969,108) can also be used. An additional aspect of the invention utilizes the techniques described for the construction of a Fab expression library (see, e.g., Huse et al., supra) to allow rapid and easy identification of monoclonal Fab fragments with the desired specificity for antigens, fragments, derivatives, or analogs thereof.

Antibodies that contain the idiotype of the molecule can be generated by known techniques. For example, such fragments include but are not limited to, the F(ab')$_2$ fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405 (the disclosure of which is incorporated by reference herein).

Antibody screening can be accomplished by techniques known in the art (e.g., ELISA (enzyme-linked immunosorbent assay)). In one example, antibodies that recognize a specific domain of an antigen can be used to assay generated hybridomas for a product which binds to polypeptides containing that domain. Small amounts of humanized antibody can be produced in a transient expression system in CHO cells to establish that they bind to HUVEC cells expressing antigens relevant to the methods of the invention. Stable cell lines can then be isolated to produce larger quantities of purified material. The binding affinity of murine and humanized antibodies can be determined using the procedure described by Krause et al., *Behring Inst. Mitt.*, 87:56–67 (1990).

Antibodies binding to antigens relevant to the methods of the invention (including fragments, derivatives and analogs) can be used for passive antibody treatment, according to methods known in the art. The antibodies can be produced as described above and can be polyclonal or monoclonal antibodies and administered intravenously, enterally (e.g., as an enteric coated tablet form), by aerosol, orally, transdermally, transmucosally, intrapleurally, intrathecally, or by other suitable routes.

The foregoing methods relating to antibodies allow production of antibodies which bind specifically to receptors, e.g. AT2 or α7nAChR, or to substances that modulate activity of receptors, e.g. substances which either stimulate or inhibit activation of receptors such as angiotensin II, nicotine, or β-amyloid. Further, specific antibodies may be produced that inhibit or affect the activity of enzymes, such as ACE, that indirectly affect stimulation of a relevant receptor via activation of a stimulatory substance.

Pharmaceutical Compositions. The present invention also relates to compositions that can be used for prophylaxis of a condition or disorder to a subject susceptible to such a condition or disorder, and for providing treatment to a subject suffering therefrom. For example, the compositions can be administered to a patient an amount of a compound effective for providing some degree of prevention of the progression of a CNS disorder (i.e., provide protective effects), amelioration of the symptoms of a CNS disorder, and amelioration of the reoccurrence of a CNS disorder. The compositions can include an effective amount of a compound that stimulates a nicotine receptor. The invention also involves the administration of effective amounts of compounds that inhibit the AT2 receptor, or that inhibit the effects of a stimulator of the AT2 receptor. Compounds that prevent Aβ-mediated interference with JAK2 phosphorylation can also be administered as pharmaceutical compositions according to the present invention.

The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, hemigalactarate, propionate, succinate, lactate, glycolate, malate, tartrate, citrate, maleate, fumarate, methanesulfonate, p-toluenesulfonate, ditoluyl tartrate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Compounds useful in the methods described herein can be those described, for example, in, Williams et al. *DN&P* 7(4):205–227 (1994), Arneric et al., *CNS Drug Rev.* 1(1): 1–26 (1995), Arneric et al., *Exp. Opin. Invest. Drugs* 5(1): 79–100 (1996), Bencherif et al., *JPET* 279:1413 (1996), Lippiello et al., JPET 279:1422 (1996), Damaj et al., *Neuroscience (*1997), Holladay et al., *J. Med. Chem* 40(28): 4169–4194 (1997), Bannon et al., *Science* 279: 77–80

(1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of which are incorporated herein by reference in their entirety. Compounds of the present invention can be used as analgesics, to prevent or treat a variety of neurodegenerative diseases, and to treat convulsions such as those that are symptomatic of epilepsy. CNS disorders which can be prevented or treated in accordance with the present invention include presenile dementia (early onset Alzheimer's disease), senile dementia (dementia of the Alzheimer's type), HIV-dementia, multiple cerebral infarcts, Parkinsonism including Parkinson's disease, Pick's disease, Huntington's chorea, progressive supra nuclear palsy, Lewy body dementia, and mild cognitive impairment. Compounds of the present invention also can be used to prevent or treat conditions such as syphilis and Creutzfeld-Jakob disease.

The pharmaceutical compositions also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, each compound can be presented in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available, for example, from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is administered to a human being. In addition, the time of day and the number of times per day that the pharmaceutical formulation is administered can vary. Administration can be such that the active ingredients of the pharmaceutical formulation interact with receptor sites within the body of the subject that effect the functioning of the CNS. More specifically, in prophylaxis and/or treatment of a CNS disorder administration can be such as to optimize the effect upon those relevant receptor subtypes that have an effect upon the functioning of the CNS, while minimizing the effects upon muscle-type receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount," "therapeutic amount," or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release, but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound orally in an amount of from about 1 µg/kg to about 20 mg/kg of patient weight. Often, the compounds of the present invention are administered in an amount from about 10 µg/kg to about 10 mg/kg of patient weight, frequently from about 10 µg to about 1 mg/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 1 to about 100 mg/24 hr/patient. For human patients, the effective dose of typical compounds requires administering the compound which generally does not exceed about 500, often does not exceed about 400, and frequently does not exceed about 300 mg/24 hr/patient. In addition, administration of the effective dose is such that the concentration of the compound within the plasma of the patient normally does not exceed 10 µg/ml, and frequently does not exceed 1 µg/ml.

The compounds according to the method of the present invention can have the ability to pass across the blood-brain barrier of the patient. Such compounds have the ability to enter the central nervous system of the patient. The log P values of typical compounds, which are useful in carrying out the present invention are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane. See, Hansch, et al., *J. Med. Chem.* 11:1 (1968).

The receptor binding constants of typical compounds useful in carrying out the present invention generally exceed about 0.1 nM, often exceed about 1 nM, and frequently exceed about 10 nM. The receptor binding constants of certain compounds are less than about 100 µM, often are less than about 10 µM and frequently are less than about 5 µM; and of other compounds generally are less than about 1 µM, often are less than about 100 µM, and frequently are less than about 50 nM. Certain compounds can possess receptor binding constants of less than 10 µM, and even less than 100 µM. Receptor binding constants provide a measure of the ability of the compound to bind to half of the relevant receptor sites of certain brain cells of the patient. See, Cheng, et al., *Biochem. Pharmacol.* 22:3099 (1973).

Certain compounds useful according to the method of the present invention can have the ability to demonstrate a nicotinic function by effectively binding to a nicotinic acetylcholine receptor. Such compounds have the ability to activate relevant neurons to release or secrete acetylcholine, dopamine, and other neurotransmitters. Generally, typical compounds useful in carrying out the present invention provide for the activation of nicotinic acetylcholine receptor in amounts of at least one third, typically at least about 10 times less, frequently at least about 100 times less, and sometimes at least about 1,000 times less, than those required for activation of muscle-type nicotinic receptors. Certain compounds of the present invention can provide secretion of dopamine in an amount which is comparable to that elicited by an equal molar amount of (S)-(−)-nicotine.

The compounds useful according to the methods of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder, is essentially ineffective in eliciting activation of certain muscle-type nicotinic receptors at concentration higher than 5 times, higher than 100 times, and higher than 1,000 times, than those required for activation of dopamine release. This selectivity of certain compounds of the present invention against those ganglia-type receptors responsible for cardiovascular side effects is demonstrated by a lack of the ability of those compounds to activate nicotinic function of adrenal chromaffin tissue at concentrations greater than those required for activation of dopamine release.

Certain compounds useful according to the methods of the present invention, when employed in effective amounts in accordance with the method of the present invention, can be effective towards prevention of the progression of CNS disorders, amelioration of the symptoms of CNS disorders, and amelioration of the reoccurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided and certain side effects are avoided. That is, an effective dose of a compound of the present invention is sufficient to provide the desired effects upon the CNS, but is insufficient (i.e., is not at a high enough level) to provide significant undesirable side effects.

The following detailed Examples are not limiting and are only illustrative of the methods and compositions of the invention.

EXAMPLES

The following examples utilized materials and methods as indicated:

Chemicals. Molecular weight standards, acrylamide, sodium dodecyl sulfate (SDS), N-N'-methylene-bisacrylamide, N,N,N',N'-tetramethylenediamine, protein assay reagents and nitrocellulose membranes were purchased from Bio-Rad Laboratories (Hercules, Calif., USA). Protein A/G-agarose was obtained from Santa-Cruz Biotechnology (Santa Cruz, Calif., USA) whereas Dulbecco's modified Eagle's medium (DMEM), fetal bovine serum, trypsin, and all medium additives were obtained from Mediatech Inc. (Herndon, Va., USA). Monoclonal antibody to phosphotyrosine (PY20), JAK2, Akt and PI3 Kinase were procured from Transduction Laboratories (Lexington, Ky., USA). Anti-phospho Akt and PARP antibodies were purchased from New England Biolabs (Beverly, Mass., USA). Anti-phosphotyrosine JAK2 antibody was obtained from Biosource International (Camarillo, Calif., USA). The Pierce SUPERSIGNAL substrate chemiluminescence detection kit was obtained from PIERCE (Rockford, Ill., USA). Goat anti-mouse IgG and anti-rabbit IgG were acquired from Amersham (Princeton, N.J., USA), and TWEEN-20, nicotine, $A\beta(1–42)$ peptide, anti-$A\beta(1–42)$ and anti-$\alpha7$-nAChR and all other chemicals were purchased from Sigma Chemical Corp. (St. Louis, Mo., USA).

Isolation and Culture of PC12 cells. PC12 (rat pheochromocytoma) cells were maintained in proliferative growth phase in DMEM (GIBCO/BRL, Gaithersburg, Md.) supplemented with 10% horse serum, 5% fetal calf serum (Atlanta Biologicals, Norcross, Ga.) and antibiotics (penicillin/streptomycin) according to routine protocols (Liu Q., et al. *Proc Natl Acad Sci USA* 98(8):4734–9 (2001)). For particular examples, the media was changed to fresh serum-free media containing either 10 µM AG-490, 10 µM $A\beta(1–42)$ prior to nicotine stimulation.

Data analysis. All statistical comparisons were made using Student's t test for paired data and analysis of variance (ANOVA). Significance was P<0.05.

Example 1

Immunoprecipitation and Phosphorylation Analysis of Pathway Proteins

PC12 cells were stimulated with nicotine for timed periods. The immunoprecipitation and Western blotting was performed as previously described (Liang, H., et al., *J. Biol. Chem.* 274: 19846–19851 (1999); Marrero, M. B., et al., *Nature* 375:247–250 (1995). Marrero, M. B., et al., *Am. J. Physiol.* 275:C1216–C1223 (1998)).

To immunoprecipitate proteins the following antibodies were used: anti-$\alpha7$ receptor, anti-PI-3 kinase (2 µg/ml), anti-JAK2 (2 µg/ml), or anti-phosphotyrosine (PY20 clone, 10 µg/ml). The recovered immunoprecipitated proteins was transferred to nitrocellulose membrane and blotted with the appropriate antibodies. For the phosphospecific JAK2 and Akt proteins, the nitrocellulose membrane was incubated overnight at 4° C. with affinity-purified anti-phosphospecific JAK2 and Akt antibodies. Finally, proteins were visualized using a horseradish-peroxidase conjugated to goat anti-mouse or donkey anti-rabbit IgG and an enhanced chemiluminescence kit.

Example 2

Western Blotting Studies of JAK2 and Akt

The phosphorylation of JAK2 and Akt proteins was determined in serum-starved PC12 cells stimulated with 10 µM nicotine for various times ranging from 0 min to 120 min in the presence or absence of 10 µM AG-490 (1 hour pre-incubation). At the end of stimulation, cells were washed twice with ice-cold PBS-V (phosphate-buffered saline with 1 mmol/L $Na_3VO_4$). Each dish was then treated for 60 min with ice-cold lysis buffer (20 mmol/L Tris-HCl, pH 7.4, 2.5 mmol/L EDTA, 1% Triton X-100, 10% glycerol, 1% deoxycholate, 0.1% SDS, 10 mmol/L $Na_4P_2O_7$, 50 mmol/L NaF, 1 mmol/L $Na_3VO_4$ and 1 mmol/L PMSF), and the supernatant fractions were obtained as cell lysate by centrifugation at 58 000 g for 25 min at 4° C. Samples were resolved by 7.5% SDS-PAGE gel electrophoresis, transferred to nitrocellulose membranes and blocked by 60 min incubation at room temperature (22° C.) in TTBS (TBS with 0.05% Tween-20, pH 7.4) plus 5% skimmed milk powder. The nitrocellulose membranes were incubated overnight at 4° C. with affinity-purified anti-phospho specific JAK2 and Akt antibodies. The nitrocellulose membranes were washed twice for 10 min each with TTBS and incubated for various times with goat anti-rabbit IgG horseradish peroxidase conjugate. After extensive washing, bound antibody was visualized on KODAK BIOMAX film, PIERCE SUPERSIGNAL substrate chemiluminescence detection kit. Molecular weight markers assessed specificity of the bands.

Example 3

Immunoprecipitation Studies of PI-3 Kinase

Serum-starved PC12 cells were stimulated with 10 µM nicotine for various times ranging from 0 min to 120 min, and washed twice with ice-cold PBS-V (phosphate-buffered saline with 1 mmol/L $Na_3VO_4$). Each dish was treated for 60 min with ice-cold lysis buffer (20 mmol/L Tris-HCl, pH 7.4, 2.5 mmol/L EDTA, 1% Triton X-100, 10% glycerol, 1% deoxycholate, 0.1% SDS, 10 mmol/L $Na_4P_2O_7$, 50 mmol/L NaF, 1 mmol/L $Na_3VO_4$ and 1 mmol/L PMSF), and the supernatant fraction obtained as cell lysate by centrifugation at 58 000 g for 20 min at 4° C. The cell lysate was incubated with 10 µg/ml of anti-PI3 kinase monoclonal antibodies at 4° C. for 2 hours and precipitated by addition of 50 µl of protein A/G agarose at 4° C. overnight. The immunoprecipitates were recovered by centrifugation and washed three times with ice-cold wash buffer (TBS, 0.1% Triton X-100, 1 mmol/L PMSF, and 1 mmol/L $Na_3VO_4$). Immunoprecipitated proteins were dissolved in 100 ml of Laemmli sample buffer and 80 ml of each sample was resolved by SDS-PAGE gel electrophoresis. Samples were transferred to nitrocellulose membranes and blocked by 60 min incubation at room temperature (22° C.) in TTBS (TBS with 0.05% Tween-20, pH 7.4) plus 5% skimmed milk powder. Nitrocellulose membranes were then incubated overnight at 4° C. with 10 µg/ml of affinity-purified, anti-phosphotyrosine antibodies, and the bound antibodies were visualized using a PIERCE SUPERSIGNAL chemiluminescence detection kit.

Example 4

Assessment of PC12 cell apoptosis

Apoptosis was determined by assessing the cleavage of the DNA-repairing enzyme poly-(ADP-ribose)polymerase (PARP) using a Western blot assay. PARP (116-kDa) is an endogenous substrate for caspase-3, which is cleaved to a typical 85-kDa fragment during various forms of apoptosis. PC12 cells were treated with 100 nM AP for 8 hours in the presence or absence of nicotine and/or AG-490. The cells were collected, washed with PBS, and lysed in 120 ul of SDS-PAGE sample buffer boiled for 10 min. Total cell lysates (30 µg of protein) were separated by SDS-PAGE and transferred to nitrocellulose membranes. The membranes were blocked for 1 hr at 25° C. with 5% nonfat dry milk in TBST (25 mM Tris-HCl, pH 7.5, 0.5 M NaCl, 0.05% Tween-20). Membranes were incubated with primary PARP antibody specific for the 85-kDa fragment for 2–3 hr at 25° C., rinsed with TBST, and incubated with secondary antibody for 1 hr at 25° C. Immunodetection was performed with appropriate antibody using an enhanced chemiluminescence (ECL) system (Amersham).

Caspase 3 enzyme activity was determined with a fluorogenic substrate for caspase-3 in crude PC12 cell extracts. The caspase-3 fluorogenic peptide Ac-DEVD-AMC (Promega, Madison, Wis.) contains the specific caspase-3 cleavage sequence (DEVD) coupled at the C-terminal to the fluorochrome 7-amino-4-methyl coumarin. The substrate emits a blue fluorescence when excited at a wavelength of 360 nm. When cleaved from the peptide by the caspase 3 enzyme activity in the cell lysate, free 7-amino-4-methyl coumarin is released and can be detected by its yellow/green emission at 460 nm. Appropriate controls included a reversible aldehyde inhibitor of caspase-3 to assess the specific contribution of the caspase 3 enzyme activity. Fluorescence units were normalized relative to total protein concentration of the cell extract. The assays were performed in triplicate, and the experiments were repeated three times. In addition, the decrease in PC12 cell number was measured using a COULTER counter (model ZM, Coulter, Hialeah, Fla.).

Example 5

Animal Models for Assessing Neuroprotective Effects

Animals models that are used to evaluate the neuroprotective effects of compositions and methods according to the present invention are provided below, along with an appropriate endpoint (based on nicotine, as indicated) with citations which provide guidance regarding use of each model (all incorporated fully herein by reference):

6-OHDA (Partial Lesion)—Rats

Nicotine (NIC) (1.0 mg/kg; s.c.) attenuates dopaminergic neurotoxicity (i.e., loss of striatal dopamine loss) induced by 6-OHDA (6 µg) into the substantia nigra (Costa, G., et al., *Brain Res*, 888:336–342(2001); Soto-Otero, R. et al., *Biochem Pharmacol*, 64(1):125–35(2002)).

Reserpine-Induced Dopamine Depletion—Mice

NIC (3 mg/kg; s.c.) blocked the reserpine (0.5 mg/kg; i.v.)-induced dopamine depletion and this effect of NIC was blocked by mecamylamine but not by hexamethonium (Oishi, R., et al., *Naunyn Schmiedebergs Arch Pharmacol.* 348:154–7(1993)).

Methamphetamine Toxicity—Mice and Rats

NIC (1.0 mg/kg) prevents methamphetamine (5 mg/kg)-toxicity (brain levels) in mice similar to MK-801 (Maggio, R., et al., *J Neurochem,* 71:2439–46(1998); and Parain, K, et al., *Brain Res.* 890:347–350(2001).

MPTP effects

Mice NIC (0.75 mg/kg) reduces striatal MPP+levels induced by MPTP (30 mg/kg; s.c.) similar to MK-801 (Quik, M. and D. A. Di Monte, *Brain Res,* 917:219–24 (2001)).

Non-Human Primates

SIB-1508Y (1.8 mg/kg) was more effective than nicotine in enhancing the effects of L-dopa on motor and cognitive function in the primate MPTP model (Domino, E. F., et al., *Exp Neurol,* 158:414–21(1999); Schneider, J. S. et al., *J Pharmacol Exp Ther.* 290(2):731–739(1999)).

Example 6

TC-1698 Mediated Increase in JAK2 Phosphorylation

In PC12 cells, similarly to nicotine, TC-1698 (2-Pyridin-3-yl-1-aza-bicyclo[3.2.2]nonane) induces phosphorylation of Jak-2 and potently activates this pathway. See FIGS. 11–15, and the preceding descriptions thereof.

TC-1698 is a potent and selective α7 agonist. Functional assays indicate that TC-1698 does not activate the ganglionic subtype α3β4, the muscle subtype α1β1γδ, the neuronal subtypes α3β2 and α4β2. In contrast TC-1698 binds to the α7 with high affinity (Ki=0.8 nM) and is 50-fold more potent than the endogenous neurotransmitter acetylcholine in activating α7 nAChR.

What this claimed is:

1. A composition, comprising,
   a) a substance that binds α7 nicotinic acetylcholine receptors (α7-nAChR); and
   b) at least one angiotensin-converting enzyme (ACE) inhibitor; and
   c) a pharmaceutically acceptable carrier.

2. The composition of claim 1, wherein the substance that binds α7-nAChR is selected from the group consisting of 2-(3-pyridyl)azaadamantanes, diazabicyclic compounds, pyridylazabicyclic compounds, cinnamamides of 3-aminoquinuclidine, arylcarbamates of 3-quinuclidinol, aromatic amides of 3-aminoquinuclidine, spiroquinuclidines, and benzylideneanabaseines.

3. The composition of claim 1, wherein the angiotensin-converting enzyme (ACE) inhibitor is selected from the group consisting of captopril, enalapril, lisinopril, benazepril, quinapril, ramipril, trandolapril, moexipril, fosinopril, and zofenopril.

4. The composition of claim 1, wherein the substance that binds α7 nAChR is a 2-(3-pyridyl)azaadamantane compound selected from the group consisting of
   1-aza-2-(5-bromo(3-pyridyl))tricyclo[3.3.1.1$^{3,7}$]decane;
   1-aza-2-(5-amino-(3-pyridyl))tricyclo[3.3.1.1$^{3,7}$]decane;
   1-aza-2-(5-ethoxy-(3-pyridyl))tricyclo[3.3.1.1$^{3,7}$]decane;
   1-aza-2-(5-isopropoxy-(3-pyridyl))tricyclo[3.3.1.1$^{3,7}$]decane;
   2-(3-pyridyl)-1-azatricyclo[3.3.1.1$^{3,7}$]decane;
   5-aza-6-(3-pyridyl)tricyclo[3.3.1.1$^{3,7}$]decan-2-ol;
   5-aza-1-(hydroxymethyl)-6-(3-pyridyl)tricyclo[3.3.1.1$^{3,7}$]-decan-2-one;
   1-aza-2-(3-pyridyl)-1-azatricyclo[3.3.1.1$^{3,7}$]decane;
   5-aza-6-(3-pyridyl)tricyclo[3.3.1.1$^{3,7}$]decan-2-ol;
   5-aza-1-(hydroxymethyl)-6-(3-pyridyl)tricyclo[3.3.1.1$^{3,7}$]-decan-2-one;
   5-aza-6-(3-pyridyl)tricyclo[3.3.1.1$^{3,7}$]decan-2-one;
   enantiomers thereof; and
   pharmaceutically acceptable salts thereof.

5. The composition of claim 1, where the substance that binds α7 nAChR is a diazabicyclic compound selected from the group consisting of
   (1S,4S)-2-(5-phenoxy-3-pyridyl)-2,5-diazabicyclo[2.2.1]heptane;
   (1R,4R)-2-(5-phenoxy-3-pyridyl)-2,5-diazabicyclo[2.2.1]heptane;
   (1S,4S)-2-(5-(3-methoxyphenoxy)-3-pyridyl)-2,5-diazabicyclo[2.2.1]heptane;
   (1R,4R)-2-(5-(3-methoxyphenoxy)-3-pyridyl)-2,5-diazabicyclo[2.2.1]heptane;
   (1S,4S)-2-(5-(4-methoxyphenoxy)-3-pyridyl)-2,5-diazabicyclo[2.2.1]heptane;
   (1R,4R)-2-(5-(4-methoxyphenoxy)-3-pyridyl)-2,5-diazabicyclo[2.2.1]heptane;
   (1S,4S)-2-(5-(3,4-dimethoxyphenoxy)-3-pyridyl)-2,5-diazabicyclo[2.2.1]heptane;
   (1R,4R)-2-(5-(3,4-dimethoxyphenoxy)-3-pyridyl)-2,5-diazabicyclo[2.2.1]heptane;
   (1S,4S)-2-(5-(4-fluorophenoxy)-3-pyridyl)-2,5-diazabicyclo[2.2.1]heptane;
   (1R,4R)-2-(5-(4-fluorophenoxy)-3-pyridyl)-2,5-diazabicyclo[2.2.1]heptane;
   (1S,4S)-2(5-benzoyl-3-pyridyl)-2,5-diazabicyclo[2.2.1]heptane;
   (1R,4R)-2-(5-benzoyl-3-pyridyl)-2,5-diazabicyclo[2.2.1]heptane;
   (1S,4S)-2-(5-(4-(N-phenylpiperidinyl)oxy)-3-pyridyl)-2,5-diazabicyclo[2.2.1]heptane;
   (1R,4R)-2-(5-(4-(N-phenylpiperidinyl)oxy)-3-pyridyl)-2,5-diazabicyclo[2.2.1]heptane;
   (1S,4S)-2-(5-(4-(N-trifluoroacetylpiperidinyl)oxy)-3-pyridyl)-2,5-diazabicyclo[2.2.1]heptane;
   (1R,4R)-2-(5-(4-(N-trifluoroacetylpiperidinyl)oxy)-3-pyridyl)-2,5-diazabicyclo[2.2.1]heptane;
   6-methyl-3-(5-phenyl-3-pyridyl)-3,6-diazabicyclo[3.2.1]octane;
   6-methyl-3-(5-phenoxy-3-pyridyl)-3,6-diazabicyclo[3.2.1]octane;
   6-methyl-3-(5-(3-methoxyphenoxy)-3-pyridyl)-3,6-diazabicyclo[3.2.1]octane;
   6-methyl-3-(5-(4-methoxyphenoxy)-3-pyridyl)-3,6-diazabicyclo[3.2.1]octane;
   6-methyl-3-(5-(3,4-dimethoxyphenoxy)-3-pyridyl)-3,6-diazabicyclo[3.2.1]octane;
   6-methyl-3-(5-(4-fluorophenoxy)-3-pyridyl)-3,6-diazabicyclo[3.2.1]octane;
   6-methyl-3-(5-benzoyl-3-pyridyl)-3,6-diazabicyclo[3.2.1]octane;
   6-methyl-3-(5-(4-(N-phenylpiperidinyl)oxy)-3-pyridyl)-3,6-diazabicyclo[3.2.1]octane;
   3-methyl-6-(5-phenyl-3-pyridyl)-3,6-diazabicyclo[3.2.1]octane;
   3-methyl-6-(5-phenoxy-3-pyridyl)-3,6-diazabicyclo[3.2.1]octane;
   3-methyl-6-(5-(3-methoxyphenoxy)-3-pyridyl)-3,6-diazabicyclo[3.2.1]octane;
   3-methyl-6-(5-(4-methoxyphenoxy)-3-pyridyl)-3,6-diazabicyclo[3.2.1]octane;
   3-methyl-6-(5-(3,4-dimethoxyphenoxy)-3-pyridyl)-3,6-diazabicyclo[3.2.1]octane;
   3-methyl-6-(5-(4-fluorophenoxy)-3-pyridyl)-3,6-diazabicyclo[3.2.1]octane;

3-methyl-6-(5-benzoyl-3-pyridyl)-3,6-diazabicyclo [3.2.1]octane;
3-methyl-6-(5-(4-(N-phenylpiperidinyl)oxy)-3-pyridyl)-3,6-diazabicyclo[3.2.1]octane;
6-(5-phenyl-3-pyridyl)-3,6-diazabicyclo[3.2.2]nonane;
6-(5-phenoxy-3-pyridyl)-3,6-diazabicyclo[3.2.2]nonane;
6-(5-(3-methoxyphenoxy)-3-pyridyl)-3,6-diazabicyclo [3.2.2]nonane;
6-(5-(4-methoxyphenoxy)-3-pyridyl)-3,6-diazabicyclo [3.2.2]nonane;
6-(5-(3,4-dimethoxyphenoxy)-3-pyridyl)-3,6-diazabicyclo[3.2.2]nonane;
6-(5-(4-fluorophenoxy)-3-pyridyl)-3,6-diazabicyclo [3.2.2]nonane;
6-(5-benzoyl-3-pyridyl)-3,6-diazabicyclo[3.2.2]nonane;
6-(5-(4-(N-phenylpiperidinyl)oxy)-3-pyridyl)-3,6-diazabicyclo[3.2.2]nonane;
3-(5-phenyl-3-pyridyl)-3,6-diazabicyclo[3.2.2]nonane;
3-(5-phenoxy-3-pyridyl)-3,6-diazabicyclo[3.2.2]nonane;
3-(5-(3-methoxyphenoxy)-3-pyridyl)-3,6-diazabicyclo [3.2.2]nonane;
3-(5-(4-methoxyphenoxy)-3-pyridyl)-3,6-diazabicyclo [3.2.2]nonane;
3-(5-(3,4-dimethoxyphenoxy)-3-pyridyl)-3,6-diazabicyclo[3.2.2]nonane;
3-(5-(4-fluorophenoxy)-3-pyridyl)-3,6-diazabicyclo [3.2.2]nonane;
3-(5-benzoyl-3-pyridyl)-3,6-diazabicyclo[3.2.2]nonane;
3-(5-(4-(N-phenylpiperidinyl)oxy)-3-pyridyl)-3,6-diazabicyclo[3.2.2]nonane;
3-(5-phenyl-3-pyridyl)-3,7-diazabicyclo[3.1.1]nonane;
3-(5-phenoxy-3-pyridyl)-3,7-diazabicyclo[3.1.1]nonane;
3-(5-(3-methoxyphenoxy)-3-pyridyl)-3,7-diazabicyclo [3.1.1]nonane;
3-(5-(4-methoxyphenoxy)-3-pyridyl)-3,7-diazabicyclo [3.1.1]nonane;
3-(5-(3,4-dimethoxyphenoxy)-3-pyridyl)-3,7-diazabicyclo[3.1.1]nonane;
3-(5-(4-fluorophenoxy)-3-pyridyl)-3,7-diazabicyclo [3.1.1]nonane;
3-(5-benzoyl-3-pyridyl)-3,7-diazabicyclo[3.3.1]nonane;
3-(5-(4-(N-phenylpiperidinyl)oxy)-3-pyridyl)-3,7-diazabicyclo[3.1.1]nonane;
enantiomers thereof; and
a pharmaceutically acceptable salt thereof.

6. The composition of claim 1, wherein the substance that binds α7 nAChR is a cinnamamide of 3-aminoquinuclidine selected from the group consisting of
N-(1-Azabicyclo[2.2.2]oct-3-yl)(E-3-phenylpropenamide);
N-(1-Azabicyclo[2.2.2]oct-3-yl)(3-phenylpropenamide);
N-(1-Azabicyclo[2.2.2]oct-3-yl)[E-3-(2-nitrophenyl)propenamide];
N-(1-Azabicyclo[2.2.2]oct-3-yl)[E-3-(2-nitrophenyl)propenamide];
N-(1-Azabicyclo[2.2.2]oct-3-yl)[E-3-(2-aminophenyl)propenamide];
N-(1-Azabicyclo[2.2.2]oct-3-yl)[Z-3-(2-methoxyphenyl)propenamide];
N-(1-Azabicyclo[2.2.2]oct-3-yl)-N-methyl-(E-3-phenylpropenamide);
N-(1-Azabicyclo[2.2.2]oct-3-yl)[E-2-phenylcyclopropane-1-carboxamide];.
N-(1-Azabicyclo[2.2.2]oct-3-yl)(Z-2-fluoro-3-phenylpropenamide);
N-(1-Azabicyclo[2.2.2]oct-3-yl)[E-3-(2-formamidophenyl)propenamide];
N-(1-Azabicyclo[2.2.2]oct-3-yl)[E-3-(4-nitrophenyl)propenamide];
N-(1-Azabicyclo[2.2.2]oct-3-yl)(E-3-(4-aminophenyl)propenamide;
N-(1-Azabicyclo[2.2.2]oct-3-yl)[E-3-(4-formamidophenyl)propenamide];
N-(1-Azabicyclo[2.2.2]oct-3-yl)(Z-3-methyl-3-phenylpropenamide);
N-(1-Azabicyclo[2.2.2]oct-3-yl)[E-3-(4-N-methylanilinophenyl)propenamide];
N-(1-Azabicyclo[2.2.2]oct-3-yl)[E-3-(4-N,N-dimethylaminophenyl)propenamide];
N-(1-Azabicyclo[2.2.2]oct-3-yl)(Z-3-phenylpropenamide);
N-(1-Azabicyclo[2.2.2]oct-3-yl)(E-3-methyl-3-phenylpropenamide);
N-(1-Azabicyclo[2.2.2]oct-3-yl)(E-2,3-diphenylpropenamide);
N-(1-Azabicyclo[2.2.2]oct-3-yl)[E-3-(4-methoxyphenyl)propenamide];
N-(1-Azabicyclo[2.2.2]oct-3-yl)(E methyl-3-phenylpropenamide);
N-(1-Azabicyclo[2.2.2]oct-3-yl)[E-3-(2-methylphenyl)propenamide];
N-(1-Azabicyclo[2.2.2]oct-3-yl)[E-3-(3-methoxyphenyl)propenamide];
N-(1-Azabicyclo[2.2.2]oct-3-yl)[E-3-(2-fluorophenyl)propenamide];
N-(1-Azabicyclo[2.2.2]oct-3-yl)[E-3-(4-fluorophenyl)propenamide];
N-(1-Azabicyclo[2.2.2]oct-3-yl)[E-(2-chlorophenyl)propenamide];
N-(1-Azabicyclo[2.2.2]oct-3-yl)[E-3-(3-chlorophenyl)propenamide];
N-(1-Azabicyclo[2.2.2]oct-3-yl)[E-3-(4-chlorophenyl)propenamide];
N-(1-Azabicyclo[2.2.2]oct-3-yl)[E-3-(3,4-dichlorophenyl)propenamide];
N-(1-Azabicyclo[2.2.2]oct-3-yl)-[E-3-(3-bromophenyl)propenamide];
N-(1-Azabicyclo[2.2.2]oct-3-yl)-[E-3-(4-bromophenyl)propenamide];
N-(1-Azabicyclo[2.2.2]oct-3-yl)[E-3-(3-iodophenyl)propenamide];
N-(1-Azabicyclo[2.2.2]oct-3-yl)[E-3-(4-iodophenyl)propenamide];
N-(1-Azabicyclo[2.2.2]oct-3-yl)[E-3-(2-trifluoromethylphenyl)propenamide];
N-(1-Azabicyclo[2.2.2]oct-3-yl)-[E-3-(3-trifluoromethylphenyl)propenamide];
N-(1-Azabicyclo[2.2.2]oct-3-yl)[E-3-(2-furyl)propenamide];
N-(1-Azabicyclo[2.2.2]oct-3-yl)[E-3-(3-furyl)propenamide];
N-(1-Azabicyclo[2.2.2]oct-3-yl)[E-3-(2-pyridyl)propenamide];
N-(1-Azabicyclo[2.2.2]oct-3-yl)[E-3-(3-pyridyl)propenamide];
N-(1-Azabicyclo[2.2.2]oct-3-yl)[E-3-(4-pyridyl)propenamide];
N-(1-Azabicyclo[2.2.2]oct-3-yl)[E-3-(2-thienyl)propenamide];
N-(1-Azabicyclo[2.2.2]oct-3-yl)[E-3-(3-thienyl)propenamide];
N-(1-Azabicyclo[2.2.2]oct-3-yl)[E-3-(5-nitro-2-furyl)propenamide];

N-(1-Azabicyclo[2.2.2]oct-3-yl)[E-3-(5-methoxy-3-pyridyl)propenamide];

N-(1-Azabicyclo[2.2.2]oct-3-yl)[E-3-(5-hydroxy-3-pyridyl)propenamide];

N-(1-Azabicyclo[2.2.2]oct-3-yl)[E-3-(4-imidazolyl)propenamide];

N-(endo-8-Aza-8-methylbicyclo[3.2.1]octyl)(E-3-phenylpropenamide);

N-(exo-8-Aza-8-methylbicyclo[3.2.1]octyl)(E-3-phenylpropenamide);

enantiomers thereof; and a pharmaceutically acceptable salt thereof.

7. The composition of claim 1, wherein the substance that binds α7 nAChR is an arylcarbamate of 3-quinuclidinol selected from the group consisting of N-phenylcarbamic acid 1-azabicyclo[2.2.2]octan-3-yl ester;

N-(4-bromophenyl)carbamic acid 1-azabicyclo[2.2.2]octan-3-yl ester;

N-(4-methylphenyl)carbamic acid 1-azabicyclo[2.2.2]octan-3-yl ester;

N-(4-methoxyphenyl)carbamic acid 1-azabicyclo[2.2.2]octan-3-yl ester;

N-(3,4-dichlorophenyl)carbamic acid 1-azabicyclo[2.2.2]octan-3-yl ester;

N-(4-cyanophenyl)carbamic acid 1-azabicyclo[2.2.2]octan-3-yl ester;

N-phenylcarbamic acid 1-azabicyclo[2.2.1]heptan-3-yl ester;

N-(3-methoxyphenyl)carbamic acid 1-azabicyclo[2.2.2]octan-3-yl ester;

N-phenylthiocarbamic acid 1-azabicyclo[2.2.2]octan-3-yl ester;

N-(2-pyridyl)carbamic acid 1-azabicyclo[2.2.2]octan-3-yl ester;

N-(1-naphthyl)carbamic acid 1-azabicyclo[2.2.2]octan-3-yl ester;

N-phenylcarbamic acid (3R)-1-azabicyclo[2.2.2]octan-3-yl ester;

N-phenylcarbamic acid (3S)-1-azabicyclo[2.2.2]octan-3-yl ester;

N-(4-pyridyl)carbamic acid 1-azabicyclo[2.2.2]octan-3-yl ester;

N-(m-biphenyl)carbamic acid 1-azabicyclo[2.2.2]octan-3-yl ester;

N-(3-quinolinyl)carbamic acid 1-azabicyclo[2.2.2]octan-3-yl ester;

enantiomers thereof; and pharmaceutically acceptable salts thereof.

8. The composition of claim 1, wherein the substance that binds α7 nAChR is an aromatic amide of 3-aminoquinuclidine selected from the group consisting of N-((3R)-1-azabicyclo[2.2.2]oct-3-yl)-5-phenylthiophene-2-carboxamide;

N-((3R)-1-azabicyclo[2.2.2]oct-3-yl)-5-phenyl-1,3,4-oxadiazole-2-carboxamide;

N-[(3R)-1-azabicyclo[2.2.2]oct-3-y-1]-4-(4-hydroxyphenoxy)benzamide;

N-[(3R)-1-azabicyclo[2.2.2]oct-3-yl]-4-(-4-acetamidophenoxy)benzamide;

N-[(3R)-1-azabicyclo[2.2.2]oct-3-yl]-4-phenoxybenzamide;

N-[(3R)-1-azabicyclo[2.2.2]oct-3-yl]-4-benzylbenzamide;

N-[(3R)-1-azabicyclo[2.2.2]oct-3-yl]-4-(phenylsulfanyl)benzamide;

N-[(3R)-1-azabicyclo[2.2.2]oct-3-yl]-3-phenoxybenzamide;

N-[(3R)-1-azabicyclo[2.2.2]oct-3-yl]-4-benzoylbenzamide;

N-[(3R)-1-azabicyclo[2.2.2]oct-3-yl]-4-(4-fluorophenoxy)benzamide;

N-[(3R)-1-azabicyclo[2.2.2]oct-3-yl]-4-(2-fluorophenoxy)benzamide;

N-[(3R)-1-azabicyclo[2.2.2]oct-3-yl]-4-(3-fluorophenoxy)benzamide;

N-[(3R)-1-azabicyclo[2.2.2]oct-3-yl]-4-(2-chlorophenoxy)benzamide;

N-[(3R)-1-azabicyclo[2.2.2]oct-3-yl]-4-(3-chlorophenoxy)benzamide;

N-[(3R)-1-azabicyclo[2.2.2]oct-3-yl]-4-(4-chlorophenoxy)benzamide;

N-[(3R)-1-azabicyclo[2.2.2]oct-3-yl]-4-(2-methoxyphenoxy)benzamide;

N-[(3R)-1-azabicyclo[2.2.2]oct-3-yl]-4-(3-methoxyphenoxy)benzamide;

N-[(3R)-1-azabicyclo[2.2.2]oct-3-yl]-4-(4-methoxyphenoxy)benzamide;

N-[(3R)-1-azabicyclo[2.2.2]oct-3-yl]-4-(3-chlorophenylsulfanyl)benzamide;

N-[(3R)-1-azabicyclo[2.2.2]oct-3-yl]-4-(4-methoxyphenoxy)benzamide;

N-[(3R)-1-azabicyclo[2.2.2]oct-3-yl]-4-(3-chlorophenylsulfanyl)benzamide;

N-[(3R)-1-azabicyclo[2.2.2]oct-3-yl]-4-(4-chlorophenylsulfanyl)benzamide;

N-[(3R)-1-azabicyclo[2.2.2]oct-3-yl]-4-(3-methoxyphenylsulfanyl)-benzamide;

N-[(3R)-1-azabicyclo[2.2.2]oct-3-yl]-4(2-methoxyphenylsulfanyl)-benzamide;

N-(2-methyl-1-azabicyclo[2.2.2]oct-3-yl)-4-phenoxybenzamide;

enantiomers thereof; and pharmaceutically acceptable salts thereof.

9. The composition of claim 1, wherein the substance that binds α7 nAChR is a spiroquinuclidines selected from the group consisting of spiro[1-azabicyclo[2.2.2]octane-3,2'-(3'H)-furo[2,3-b]pyridine];

5'-bromospiro[1-azabicyclo[2.2.2]octane-3,2'-(3'H)-furo[2,3-b]pyridine];

5'-phenylspiro[1-azabicyclo[2.2.2]octane-3,2'-(3'H)-furo[2,3-b]pyridine];

5'-nitrospiro[1-azabicyclo[2.2.2]octane-3,2'-(3'H)-furo[2,3-b]pyridine];

1'-chlorospiro[1-azabicyclo[2.2.2]octane-3,2'-(3'H)-furo[2,3-b]isoquiniline];

5'-(phenylcarboxamido)spiro[1-azabicyclo[2.2.2]octane-3,2'-(3'H)-furo[2,3-b]pyridine];

5'-(phenylaminocarbonylamino)spiro[1-azabicyclo[2.2.2]octane-3,2'-(3'H)-furo[2,3-b]pyridine];

5'-(phenylsulfonylamido)spiro[1-azabicyclo[2.2.2]octane-3,2'-(3'H)-furo[2,3-b]pyridine];

5'-aminospiro[1-azabicyclo[2.2.2]octane-3,2'-(3'H)-furo[2,3-b]pyridine];

5'-N-methylaminospiro[1-azabicyclo[2.2.2]octane-3,2'-(3'H)-furo[2,3-b]pyridine];

5'-N,N-dimethylaminospiro[1-azabicyclo[2.2.2]octane-3,2'-(3'H)-furo[2,3-b]pyridine];

5'-N,N-diethylaminospiro[1-azabicyclo[2.2.2]octane-3,2'-(3'H)-furo[2,3-b]pyridine];

5'-N-ethylaminospiro[1-azabicyclo[2.2.2]octane-3,2'-(3'H)-furo[2,3-b]pyridine];

5'-N-benzylaminospiro[1-azabicyclo[2.2.2]octane-3,2'-(3'H)-furo[2,3-b]pyridine]
5'-N-formamidospiro[1-azabicyclo[2.2.2]octane-3,2'-(3'H)-furo[2,3-b]pyridine];
5'-N-acetamidospiro[1-azabicyclo[2.2.2]octane-3,2'-(3'H)-furo[2,3-b]pyridine];
spiro[1-azabicyclo[2.2.2]octane-3,2'-(3'H)-furo[2,3-b]isoquinoline];
Spiro[1-azabicyclo[2.2.2]octane-3,2'-(3'H)-furo[2,3-b]quiniline];
5'-ethenylspiro[1-azabicyclo[2.2.2]octane-3,2'-(3'H)-furo[2,3-b]pyridine];
5'-(E)-(phenylethenyl)spiro[1-azabicyclo[2.2.2]octane-3,2'-(3'H)-furo[2,3-b]pyridine];
5'-(4-morpholino)spiro[1-azabicyclo[2.2.2]octane-3,2'-(3'H)-furo[2,3-b]pyridine];
5'-(1-azetidinyl)spiro[1-azabicyclo[2.2.2]octane-3,2'-(3'H)-furo[2,3-b]pyridine];
5'-(E)-(2-(4-pyridyl)ethenyl)spiro[1-azabicyclo[2.2.2]octane-3,2'-(3'H)-furo[2,3-b]pyridine];
5'-(E)-(2-(2-pyridyl)ethenyl)spiro[1-azabicyclo[2.2.2]octane-3,2'-(3'H)-furo[2,3-b]pyridine];
5'-(2-trimethylsilylethynyl(spiro[1-azabicyclo[2.2.2]octane-3,2'-(3'H)-furo[2,3-b]pyridine];
5'-ethynylspiro[1-azabicyclo[2.2.2]octane-3,2'-(3'H)-furo[2,3-b]pyridine];
5'-(2-furyl)spiro[1-azabicyclo[2.2.2]octane-3,2'-(3'H)-furo[2,3-b]pyridine];
5'-(3-pyridyl)spiro[1-azabicyclo[2.2.2]octane-3,2'-(3'H)-furo[2,3-b]pyridine];
5'-methylspiro[1-azabicyclo[2.2.2]octane-3,2'-(3'H)-furo[2,3-b]pyridine];
spiro[1-azabicyclo[2.2.2]octane-3,2'-3'H)-furo[2,3-b]pyridine-5'carbonitrile];
spiro[1-azabicyclo[2.2.2]octane-3,2'-(3'H)-furo[2,3-b]pyridine-5'carboxamide];
5'-N'-(3-chlorophenyl)ureidoaminospiro[1-azabicyclo[2.2.2]octane-3,2'-(3'H)-furo[2,3-b]pyridine];
5'-N'-(2-nitrophenyl)ureidoaminospiro[1-azabicyclo[2.2.2]octane-3,2'-(3'H)-furo[2,3-b]pyridine];
4'chlorospiro[1-azabicyclo[2.2.2]octane-3,2'-(3'H)-furo[2,3-b]pyridine];
4'-methoxyspiro[1-azabicyclo[2.2.2]octane-3,2'-(3'H)-furo[2,3-b]pyridine];
4'-phenylthiospiro[1-azabicyclo[2.2.2]octane-3,2'-(3'H)-furo[2,3-b]pyridine];
4'-(N-2-aminoethyl)aminospiro[1-azabicyclo[2.2.2]octane-3,2'-(3'H)-furo[2,3-b]pyridine];
4'-phenylaminospiro[1-azabicyclo[2.2.2]octane-3,2'-(3'H)-furo[2,3-b]pyridine];
4'-methylaminospiro[1-azabicyclo[2.2.2]octane-3,2'-(3'H)-furo[2,3-b]pyridine];
4'-(4-N-methylpiperazin-1-yl)spiro[1-azabicyclo[2.2.2]octane-3,2'-(3'H)-furo[2,3-b]pyridine];
4'-chloro-spiro[1-azabicyclo[2.2.2]octane-3,2'-(3'H)-furo[3,2-c]pyridine];
spiro[1-azabicyclo[2.2.2]octane-3,2'-(3'H)-furo[3,2-c]pyridine];
6'-fluorospiro[1-azabicyclo[2.2.2]octane-3,2'(3'H)-furo[2,3-b]pyridine];
Spiro[1-azabicyclo[2.2.2]octane-3,2'(3'H)-furo[2,3-b]pyridine-6'-carbonitrile];
6'-chlorospiro[1-azabicyclo[2.2.2]octane-3,2'(3'H)-furo[2,3-b]pyridine];
enantiomers thereof; and
pharmaceutically acceptable salts thereof.

10. The composition of claim 1, wherein the substance that binds α7 nAChR is a benzylideneanabaseine selected from the group consisting of
3-(2,4-dimethoxybenzylidene)anabaseine, 3-(4-hydroxybenzylidene)anabaseine;
3-(4-methoxybenzylidene)anabaseine, 3-(4-aminobenzylidene)anabaseine;
3-(4-hydroxy-2-methoxybenzylidene)anabaseine;
3-(2-hydroxy-4-methoxybenzylidene)anabaseine;
3-(4-isopropoxybenzylidene)anabaseine;
(7'-methyl-3-(2,4-dimethoxybenzylidene))anabaseine;
3-(4-acetylaminocinnamylidene)anabaseine;
3-(4-hydroxycinnamylidene)anabaseine;
3-(4-methoxycinnamylidene)anabaseine;
3-(4-hydroxy-2-methoxycinnamylidene)anabaseine;
3-(2,4-dimethoxycinnamylidene)anabaseine; and
3-(4-acetoxycinnamylidene)anabaseine;
enantiomers thereof; and
pharmaceutically acceptable salts thereof.

11. A composition for reducing apoptosis mediated by a β-amyloid polypeptide in mammalian neurons, comprising,
a) a substance that binds α7-nAChR; and
b) at least one ACE inhibitor; and
c) a pharmaceutically acceptable carrier.

* * * * *